US007420100B2

(12) United States Patent
Olson et al.

(10) Patent No.: US 7,420,100 B2
(45) Date of Patent: Sep. 2, 2008

(54) METHODS AND COMPOSITIONS RELATING TO HDAC 4 AND 5 REGULATION OF CARDIAC GENE EXPRESSION

(75) Inventors: Eric N. Olson, Dallas, TX (US); Jianrong Lu, Quincy, MA (US); Timothy McKinsey, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 586 days.

(21) Appl. No.: 10/637,403

(22) Filed: Aug. 8, 2003

(65) Prior Publication Data
US 2005/0106654 A1 May 19, 2005

Related U.S. Application Data

(63) Continuation of application No. 09/643,206, filed on Aug. 21, 2000, now Pat. No. 6,632,628.

(60) Provisional application No. 60/150,048, filed on Aug. 20, 1999.

(51) Int. Cl.
*A01K 67/027* (2006.01)
*G01N 33/00* (2006.01)
(52) U.S. Cl. .................... 800/18; 800/3; 800/8; 800/9; 800/13
(58) Field of Classification Search .................. None
See application file for complete search history.

(56) References Cited

U.S. PATENT DOCUMENTS

| 4,367,110 | A |   | 1/1983  | Yoshikawa |
|-----------|---|---|---------|-----------|
| 4,452,901 | A |   | 6/1984  | Gordon et al. |
| 4,668,621 | A |   | 5/1987  | Doellgast |
| 4,873,191 | A |   | 10/1989 | Wagner et al. |
| 5,252,479 | A |   | 10/1993 | Srivastava |
| 5,359,046 | A |   | 10/1994 | Capon et al. |
| 5,672,344 | A |   | 9/1997  | Kelley et al. |
| 5,708,158 | A |   | 1/1998  | Hoey |
| 5,942,435 | A | * | 8/1999  | Wheeler ...................... 435/325 |

FOREIGN PATENT DOCUMENTS

| WO | WO 84/03564   |   | 9/1984 |
|----|---------------|---|--------|
| WO | WO 94/05776   |   | 3/1994 |
| WO | WO 99/19471   |   | 4/1999 |
| WO | WO 01/14581 A2| * | 3/2001 |

OTHER PUBLICATIONS

Swiss-Prot Online Database entry Q9Z2V6, downloaded Aug. 18, 2005.*
Campbell and Wilmut (1997) Totipotency or Multipotentiality of Cultured Cells: Applications and Progress. Teratology 47:63-72.*
Wall (1996) Transgenic Livestock: Progress adn Prospects for teh Future. Theriogenology 45:57-68.*
Chang et al. Histone deacetylases 5 and 9 govern responsiveness of the heart to a subset of stress signals and play redundant roles in heart development. Mol Cell Biol. Oct. 2004;24(19):8467-76.*
Gerlai R. Gene-targeting studies of mammalian behavior: is it the mutation or the background genotype? Trends Neurosci. May 1996;19(5):177-81.*
Le Mouellic et al. Targeted replacement of the homeobox gene Hox-3.1 by the *Escherichia coli* lacZ in mouse chimeric embryos. Proc Natl Acad Sci U S A. Jun. 1990;87(12):4712-6.*
Doetschman T. Interpretation of phenotype in genetically engineered mice. Lab Anim Sci. Apr. 1999;49(2):137-43.*
Sigmund CD. Viewpoint: are studies in genetically altered mice out of control? Arterioscler Thromb Vasc Biol. Jun. 2000;20(6):1425-9.*
Verdel et al. Identification of a new family of higher eukaryotic histone deacetylases. Coordinate expression of differentiation-dependent chromatin modifiers.J Biol Chem. Jan. 22, 1999;274(4):2440-5.*
Vega et al. Histone deacetylase 4 controls chondrocyte hypertrophy during skeletogenesis. Cell. Nov. 12, 2004;119(4):555-66.*
Backs et al. (2006) J. Clin. Invest. 116:1853-1864.*
Swiss-Prot entry P12813, http://ca.expasy.org/uniprot/Q9UBM7, downloaded Aug. 28, 2007.*
Bour et al., "Drosophila MEF2, a transcription factor that is essential for myogenesis," *Genes and Dev.*, 9:730-741, 1995.
Brand, "Myocyte enhancer factor 2 (MEF2)," *Int. J. Biochem. Cell Biol.*, 29(12):1467-1470; 1997.
Bustamante et al., "Stretch-activated channels in heart cells: relevance to cardiac hypertrophy," *J. Cardiovasc. Pharmacol*, 17 (Supp 2):S110-113, 1991.
Chien et al., "Transcriptional regulation during cardiac growth and development," *Ann. Rev. Physiol.* 55, 77-95, 1993.
Clarke et al., "Epidermal Growth Factor Induction of the c-jun Promoter by a Rac Pathway," *Mol. Cell Biol.*, 18(2):1065-1073, 1998.
Coso et al., "Signaling from G Protein-coupled Receptors to the c-jun promoter Involves the MEF2 Transcription Factor," *J. Biol. Chem.*, 272(33):20691-20697, 1997.
Dubensky et al., "Direct transfection of viral and plasmid DNA into the liver or spleen of mice," *Proc. Nat'l Acad. Sci. USA*, 81:7529-7533, 1984.
Edmondson et al., "MEF2 gene expression marks the cardiac and skeletal muscle lineages during mouse embryogenesis," *Development*, 120:1251-1263, 1994.
Fischele et al., "A new family of human histone deacetylases related to *Saccharomyces cerevisiae* HDA1p," *J. Biol. Chem.*, 274(17):11713-11720, 1999.
Grozinger et al., "Three proteins define a class of human histone deacetylases related to yeast Hda1p," *Proc. Nat'l. Acad. Sci.*, 96:4868-4873, 1999.

(Continued)

*Primary Examiner*—Daniel M Sullivan
(74) *Attorney, Agent, or Firm*—Fulbright & Jaworski

(57) ABSTRACT

The present invention relates to cardiac hypertrophy. More particularly, the present invention defines the molecular events linking calcium stimulation to cardiac hypertrophy. More specifically, the present invention shows that $Ca^{2+}$ stimulation of the hypertrophic response is mediated through an HDAC 4 and 5 interaction with MEF2, and that phosphorylation of HDACs results in loss of HDAC-mediated repression of MEF2 hypertrophic action. Thus, the present invention provides methods and compositions of treating cardiac hypertrophy, as well as methods and compositions for identifying subjects at risk for cardiac hypertrophy. Further provided are methods for the detection of compounds having therapeutic activity toward cardiac hypertrophy.

5 Claims, 22 Drawing Sheets

OTHER PUBLICATIONS

Gruver et al., "Targeted developmental overexpression of calmodulin induces proliferative and hypertrophic growth of cardiomyocytes in transgenic mice," *Endocrinology*, 133(1):376-388, 1993.

Han et al., "Activation of the transcription factor MEF2C by the MAP kinase p38 in inflammation," *Nature*, 386:296-299, 1997.

Hasegawa et al., "*Cis*-acting sequences that mediate induction of the -myosin heavy chain gene expression during left ventricular hypertrophy due to aortic constriction," *Circulation*, 96(11):3943-3953, 1997.

Herzig et al., "Angiotensin II type 1a receptor gene expression in the heart: AP-1 and GATA-4 mediate the response to pressure overload," *Proc. Nat'l Acad. Sci. USA*, 94:7543-7548, 1997.

Hoch et al., "Identification and expression of δ-Isoforms of the multifunctional $Ca^{2+}$/Calmodulin-dependent protein kinase in failing and nonfailing human myocardium," *Circulation Res.*, 84:713-721, 1999.

Hongo et al., "Effect of stretch on contraction and the $Ca^{2+}$ transient in ferret ventricular muscles during hypoxia and acidosis," *Am. J. Physiol.*, 269:C690-C697, 1995.

Kao et al., "Isolation of a novel histone deacetylase reveals that class I and class II deacetylases promote SMRT-mediated repression," *Genes Dev.*, 14:55-66, 2000.

Kariya et al., "An enhancer core element mediates stimulation of the rat-myosin heavy chain promoter by an $\alpha_1$-adrenergic agonist and activated β-protein kinase C in hypertrophy of cardiac myocytes," *J. Biol. Chem.*, 269(5):3775-3782, 1994.

Karliner et al., "Effects of pertussis toxin on α1-agonist-mediated phosphatidylinositide turnover and myocardial cell hypertrophy in neonatal rat ventricular myocytes," *Experientia.*, 46:81-84, 1990.

Kato et al., "BMK1/ERK5 regulates serum-induced early gene expression through transcription factor MEF2C," *EMBO J.*, 16(23):7054-7066, 1997.

Komuro and Yazaky, "Control of cardiac gene expression of mechanical stress," *Annu. Rev. Physiol.*, 55:55-75, 1993.

Kovacic-Milivojevic et al., "Selective regulation of the atrial natriuretic peptide gene by individual components of the activator protein-1 complex," *Endocrin*, 137(3):1108-1117, 1996.

Le Guennec et al., "Stretch induced increase of resting intracellular calcium concentration in single guinea-pig ventricular myocytes," *Exp. Physiol.*, 76:975-978, 1991.

Lee et al., "Myocyte-Specific Enhancer Factor 2 and Thyroid Hormone Receptor Associate and Synergistically Activate the α-Cardiac Myosin Heavy-Chain Gene," *Mol. Cell Biol.*, 17(5):2745-2755, 1997.

Lemercier et al., "mHDA1/HDAC5 histone deacetylase interacts with and represses MEF2A transcriptional activity," *J. Biol. Chem.*, 275(20):15594-15599, 2000.

Lilly et al., "Requirement of MADS domain transcription factor D-MEF2 for muscle formation in *Drosophila*," *Science*, 267:688-693, 1995.

Lin et al., "Control of cardiac morphogenesis and myogenesis by transcription factor MEF2C," *Science*, 276:1404-1407, 1997.

Liu et al., "Cyclosporin A-sensitive induction of the Epstein-Barr virus lytic switch is mediated via a novel pathway involving a MEF2 family member," *EMBO J.*, 16(1):143-153, 1997.

Lu et al., "Regulation of skeletal myogenesis by association of the MEF2 transcriptional factor with class II histone deacetylases," *Mol Cell*, 6:233-244, 2000.

Lu et al., "Signal-dependent activation of the MEF2 transcription factor by dissociation from histone deacetylases," *PNAS*, 97(8):4070-4075, 2000.

Marban et al., "Intracellular free calcium concentration measured with $^{19}F$ NMR spectroscopy in intact ferret hearts," *Proc. Nat'l Acad. Sci. USA*, 84:6005-6009, 1987.

Martin et al., "Myocyte enhancer factor (MEF) 2C: A tissue-restricted member of the MEF-2 family of transcription factors," *Proc. Nat'l Acad. Sci. USA*, 90:5282-5286, 1993.

McDonough and Glembotski, "Induction of atrial natriuretic factor and myosin light chain-2 gene expression in cultured ventricular myocytes by electrical stimulation of contraction," *J. Biological Chem.*, 267(17):11665-11668, 1992.

McKinsey et al., "Signal-dependent nuclear export of a histone deacetylase regulates muscle differentiation," *Nature*, 408:106-111, 2000.

Miska et al., "HDAC4 deacetylase associates with and represses the MEF2 transcription factor," *EMBO J.*, 18(18):5099-5107, 1999.

Molkentin and Olson, "Combinational Control of Muscle Development by basic helix-loop-helix and MADS-box transcription factors," *Proc. Nat'l Acad. Sci. USA*, 93:9366-9373, 1996.

Molkentin and Olson, "GATA4: a novel transcriptional regulator of cardiac hypertrophy," *Circulation*, 96:3833-3835, 1997.

Molkentin et al., "MEF2B is a potent transactivator expressed in early myogenic lineages," *Mol. Cell. Biol.*, 16(7):3814-3824, 1996.

Molkentin et al., "Mutational analysis of the DNA binding, dimerization, and transcriptional activation of MEF2C," *Mol. Cell. Biol.*, 16(6):2627-2636, 1996.

Molkentin et al., "Phosphorylation of the MADS-box transcription factor MEF2C enhances its DNA binding activity," *J. Biol. Chem.*, 271(29):17199-17204, 1996.

Molkentin, et al., "Cooperative activation of muscle gene expression by MEF2 and myogenic bHLH proteins," *Cell*, 83:1125-1136, 1995.

Olson et al., "Regulation of muscle differentiation by the MEF2 family of MADS box transcription factors," *Developmental Biology*, 172:2-14, 1995.

Perreault et al., "Excitation-contraction coupling in isolated myocardium from dogs with compensated left ventricular hypertrophy," *Am. J. Physiol.*, 266:H2436-H2442, 1994.

Ramirez et al., "The Nuclear δb isoform of Ca2+/Calmodulin-dependent Protein Kinase Ii Regulates Atrial Natriuretic Factor Gene Expression in Ventricular Myocytes," *J. Biol. Chem.*, 272(49):31203-31208, 1997.

Sadoshima and Izumo, "Signal transduction pathways of angiotensin II-induced c-fos gene expression in cardiac myocytes in vitro," *Circ. Res.*, 73:424-438, 1993.

Sadoshima and Izumo, "The cellular and molecular response of cardiac myocytes to mechanical stress," *Ann. Rev. Physiol.*, 59:551-571, 1997.

Sadoshima et al., "Autocrine release of angiotensin II mediates stretch-induced hypertrophy of cardiac myocytes in vitro," *Cell*, 75:977-984, 1993.

Saeki et al., "Tension and intracellular calcium transients of activated ferret ventricular muscle in response to step length changes," *Adv. Exp. Med. Biol.*, 332:639-648, 1993.

Schwartz et al., "α-skeletal muscle actin mRNA's accumulate in hypertrophied adult rat hearts," *Circ. Res.* 59:551-555, 1986.

Sei et al., "The α-adrenergic stimulation of atrial natriuretic factor expression in cardiac myocytes requires calcium influx, protein kinase C, and calmodulin-regulated pathways," *J. Biological Chem.*, 266(24):15910-15916, 1991.

Sodering, "The $Ca^{2+}$—calmodulin-dependent protein kinase cascade," *TIBS*, 24:232-236, 1999.

Stemmer and Klee, "Dual calcium ion regulation of calcineurin by calmodulin and calcineurin B," *Biochemistry*, 33:6859-6866, 1994.

Su et al., "Distribution and activity of calcineurin in rat tissues. Evidence for post-transcriptional regulation of testis-specific calcineurin B," *Eur. J. Biochem.* 230:469-474, 1995.

Van Lint et al., "The expression of a small fraction of cellular genes is changed in response to histone hyperacetylation," *Gene Exp.*, 5:245-253, 1996.

Verdel and Khochbin, "Identification of a new family of higher eukaryotic histone deacetylases," *J. Biol Chem.*, 274(4):2440-2445, 1999.

Woronicz et al., "Regulation of the Nur77 Orphan Steroid Receptor in Activation-Induced Apoptosis," *Mol. Cell. Biol.*, 15(11):6364-6376, 1995.

Youn et al., "Calcium regulates transcriptional repression of myocyte enhancer factor 2 by histone deacetylase 4," *J. Biol. Chem.*, 275(29):22563-22567, 2000.

International Search Report, dated Feb. 7, 2001.

* cited by examiner nontransgenic
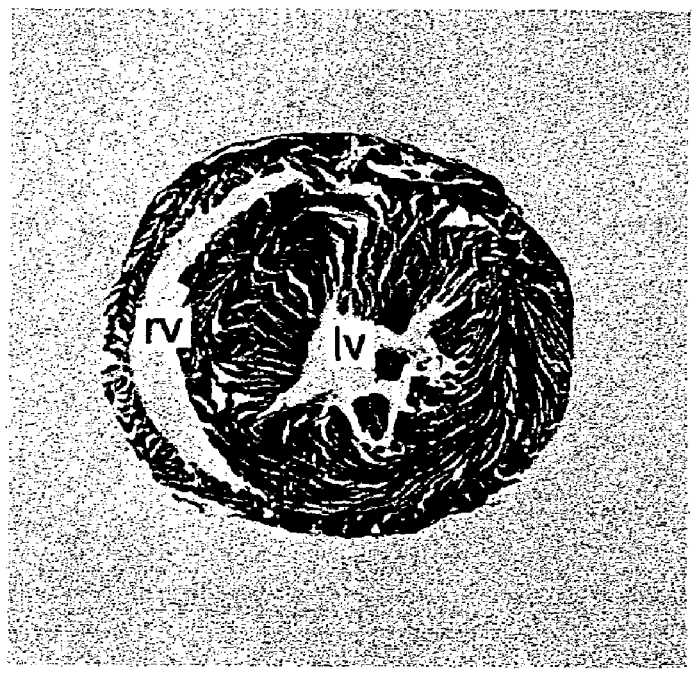
CaMKIV transgenic
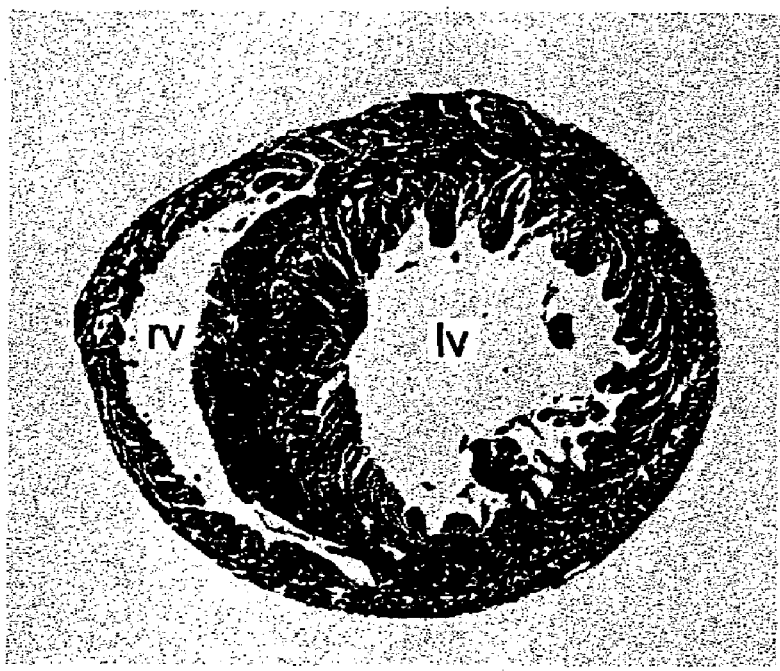
FIG. 7

Control
CaMKIV Transgenic
FIG.8

BAITS 
FIG. 9A
PREY 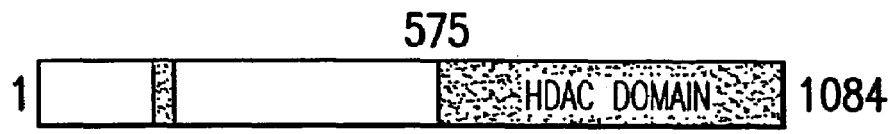
HDAC4 163– E S A V A S T E V K M K L Q E F V L –180
HDAC5 175– E S A T A S T E V K L R L Q E F L L –192
FIG. 9B

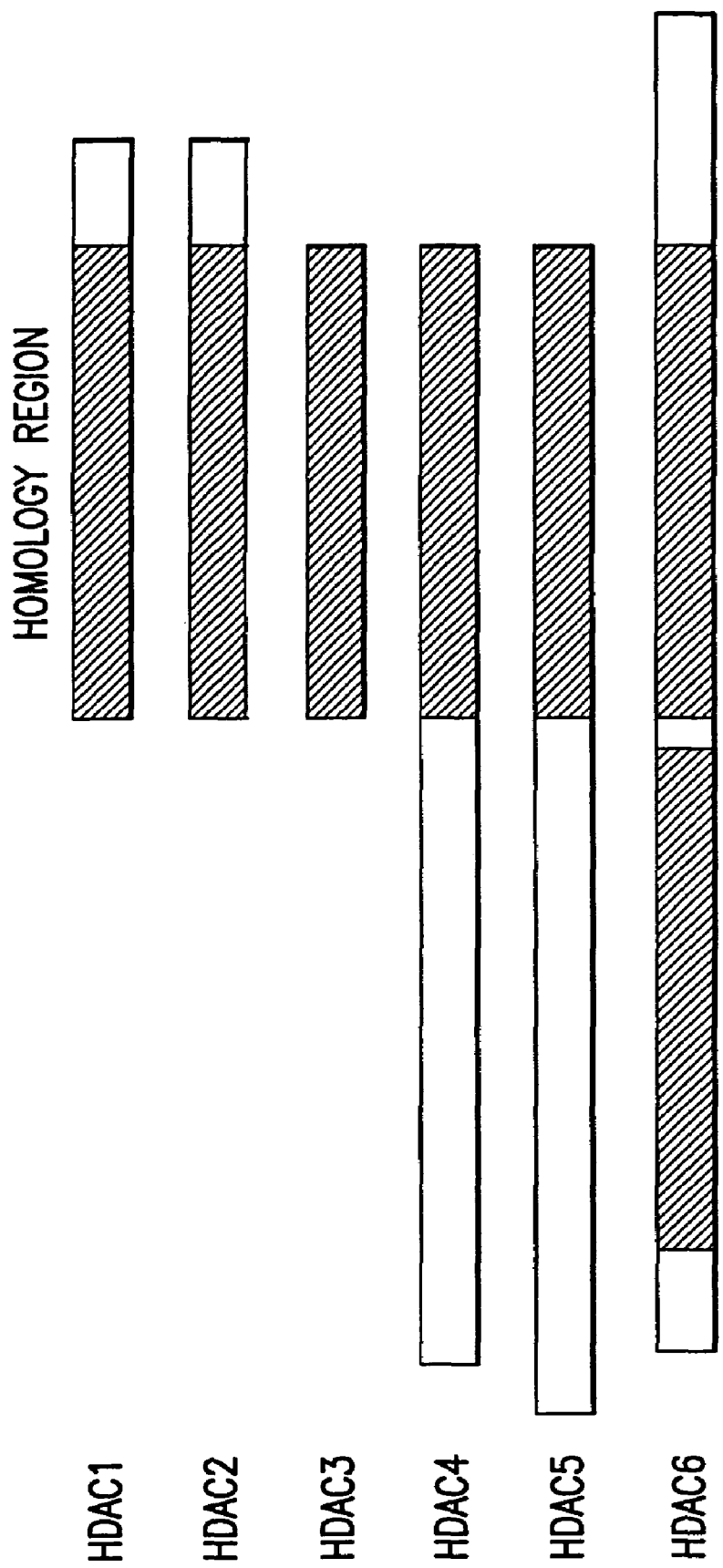

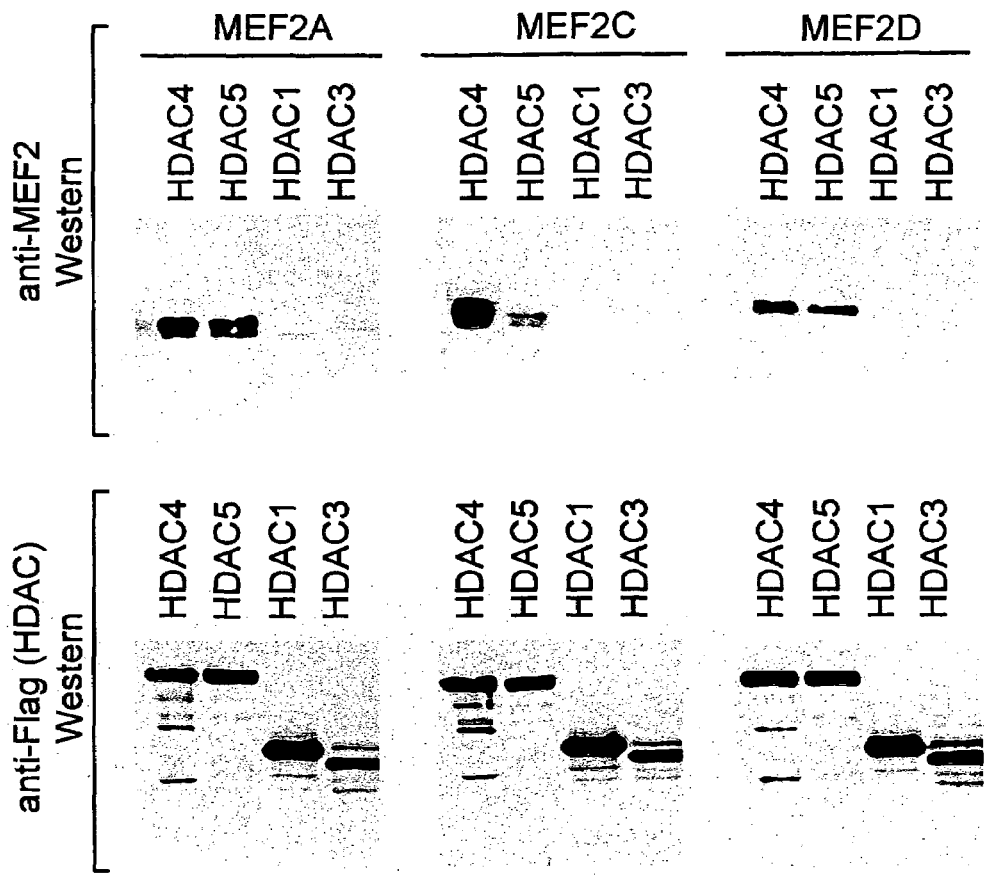
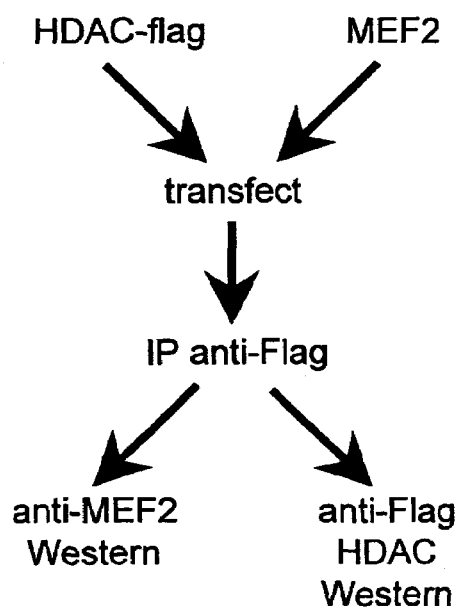
FIG. 12

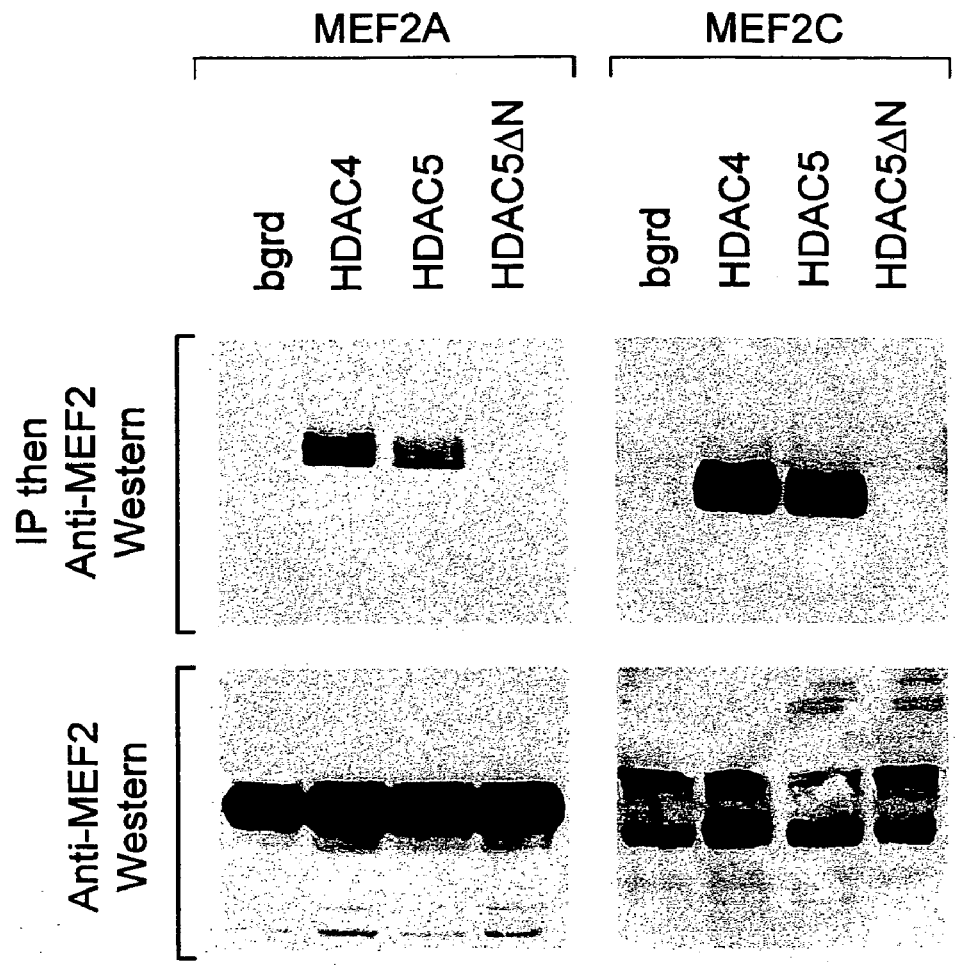
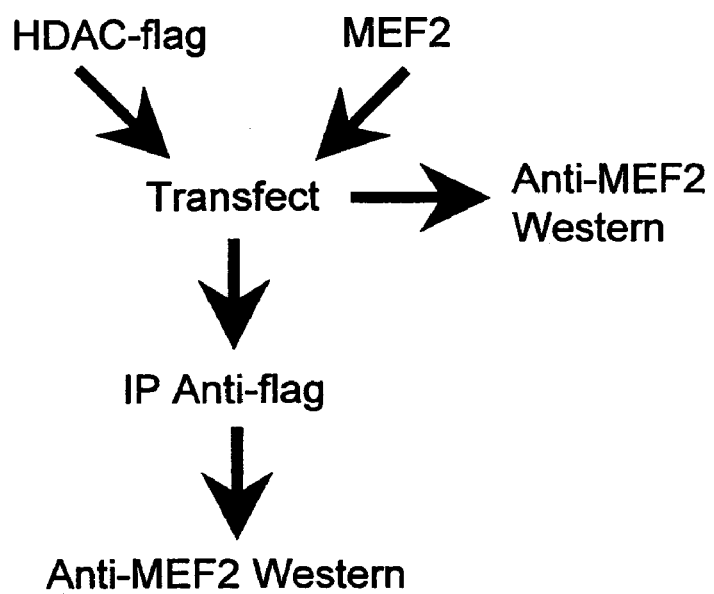
FIG. 13

METHODS AND COMPOSITIONS RELATING TO HDAC 4 AND 5 REGULATION OF CARDIAC GENE EXPRESSION

BACKGROUND OF THE INVENTION

This application is a continuation of U.S. patent application Ser. No. 09/643,206 filed on Aug. 21, 2000, now U.S. Pat. No. 6,632,628, which claims priority to U.S. Provisional Application No. 60/150,048 filed on Aug. 20, 1999, the entire contents of each which are incorporated herein by reference. Additionally, all patents, published patent applications, and other references cited throughout this specification are hereby incorporated by reference in their entireties.

1. Field of the Invention

The present invention relates generally to the field of molecular biology. More particularly, it concerns the discovery of a central mediator of cardiac hypertrophy.

2. Description of Related Art

Cardiac hypertrophy is an adaptive response of the heart to virtually all forms of cardiac disease, including those arising from hypertension, mechanical load, myocardial infarction, cardiac arrythmias, endocrine disorders and genetic mutations in cardiac contractile protein genes. While the hypertrophic response is initially a compensatory mechanism that augments cardiac output, sustained hypertrophy can lead to dilated cardiomyopathy, heart failure, and sudden death. In the United States, approximately half a million individuals are diagnosed with heart failure each year, with a mortality rate approaching 50%.

Despite the diverse stimuli that lead to cardiac hypertrophy, there is a prototypical molecular response of cardiomyocytes to hypertrophic signals that involves an increase in cell size and protein synthesis, enhanced sarcomeric organization, upregulation of fetal cardiac genes, and induction of genes such as c-fos and c-myc (reviewed in Chien et al., 1993; Sadoshima and Izumo, 1997). The causes and effects of cardiac hypertrophy have been documented extensively, but the underlying molecular mechanisms that couple hypertrophic signals, initiated at the cell membrane to reprogram cardiomyocyte gene expression remain poorly understood. Elucidation of these mechanisms is a central issue in cardiovascular biology and is critical in the design of new strategies for prevention or treatment of cardiac hypertrophy and heart failure.

Numerous studies have implicated intracellular $Ca^{2+}$ as a signal for cardiac hypertrophy. In response to myocyte stretch or increased loads on working heart preparations, intracellular $Ca^{2+}$ concentrations increase (Marban et al., 1987; Bustamante et al., 1991; Hongo et al., 1995). This is consistent with a role of $Ca^{2+}$ in coordinating physiologic responses with enhanced cardiac output. A variety of humoral factors, including angiotensin II (AngII), phenylephrine (PE) and endothelin-1 (ET-1), which induce the hypertrophic response in cardiomyocytes (Karliner et al., 1990; Sadoshima and Izumo, 1993a, 1993b; Leite et al., 1994), also share the ability to elevate intracellular $Ca^{2+}$ concentrations.

Hypertrophic stimuli result in reprogramming of gene expression in the adult myocardium such that genes encoding fetal protein isoforms like β-myosin heavy chain (MHC) and α-skeletal actin are upregulated, whereas the corresponding adult isoforms, α-MHC and α-cardiac actin, are downregulated. The natriuretic peptides, atrial natriuretic factor (ANF) and β-type natriuretic peptide (BNP), which decrease blood pressure by vasodilation and natriuresis, also are rapidly upregulated in the heart in response to hypertrophic signals (reviewed in Komuro and Yazaki, 1993). The mechanisms involved in coordinately regulating these cardiac genes during hypertrophy are unknown, although binding sites for several transcription factors, including serum response factor (SRF), TEF-1, AP-1, and SpI are important for activation of fetal cardiac genes in response to hypertrophy (Sadoshima and Izumo, 1993a; 1993b; Kariya et al., 1994; Karns et al., 1995; Kovacic-Milivojevic et al., 1996). Most recently, the cardiac-restricted zinc finger transcription factor GATA4 also has been shown to be required for transcriptional activation of the genes for Ang II type 1α receptor and β-MHC during hypertrophy (Herzig et al., 1997; Hasegawa et al., 1997; reviewed in Molkentin and Olson, 1997).

The potential roles of the myocyte enhancer factor-2 (MEF2) family of transcription factors in cardiac development and hypertrophy are also considered. There are four members of the MEF2 family, referred to as MEF2A, -B, -C, and -D, in vertebrates (reviewed in Olson et al., 1995). These transcription factors share homology in an N-terminal MADS-box and an adjacent motif known as the MEF2 domain. Together, these regions mediate DNA binding, homo- and heterodimerization, and interaction with various cofactors, such as the myogenic bHLH proteins in skeletal muscle. MEF2 binding sites, $CT(A/T)_4TAG/A$, are found in the control regions of the majority of skeletal, cardiac, and smooth muscle genes. The C-termini of the MEF2 factors function as transcription activation domains and are subject to complex patterns of alternative splicing.

During mouse embryogenesis, the MEF2 genes are expressed in precursors of cardiac, skeletal and smooth muscle lineages and their expression is maintained in differentiated muscle cells (Edmondson et al. 1994). The MEF2 factors also are expressed at lower levels in a variety of nonmuscle cell types. Targeted inactivation of MEF2C has been shown to result in embryonic death at about E9.5 due to heart failure (Lin et al., 1997). In the heart tubes of MEF2C mutant mice, several cardiac genes fail to be expressed, including α-MHC, ANF, and α-cardiac actin, whereas several other cardiac contractile protein genes are expressed normally, despite the fact that they contain essential MEF2 binding sites in their control regions. These results have demonstrated the essential role of MEF2C for cardiac development and suggest that other members of the MEF2 family may have overlapping functions that can support the expression of a subset of muscle genes in the absence of MEF2C. In Drosophila, there is only a single MEF2 gene, called D-MEF2. In embryos lacking D-MEF2, no muscle structural genes are activated in any myogenic lineage, demonstrating that MEF2 is an essential component of the differentiation programs of all muscle cell types (Lilly et al., 1995; Bour et al., 1995).

Although MEF2 factors are required for activation of muscle structural genes, they are not sufficient to activate these genes alone. Instead, biochemical and genetic studies have shown that MEF2 factors act combinatorially with other transcription factors to activate specific programs of gene expression. In skeletal muscle, MEF2 establishes a combinatorial code through interaction with members of the MyoD family to activate muscle gene transcription (Molkentin et al., 1995; Molkentin and Olson, 1996). The specific partners for MEF2 in cardiac and smooth muscle cells or in nonmuscle cells in which MEF2 proteins have been shown to regulate a variety of genes, remain to be defined.

As discussed below, there are four lines of evidence that suggest an important role for MEF2 in the control of cardiac hypertrophy. 1) MEF2 regulates many of the fetal cardiac genes that are up-regulated during hypertrophy. 2) MEF2 transcriptional activity is induced by the same signal transduction pathways that control hypertrophy. 3) MEF2C is upregulated in the hearts of human patients with congestive heart failure. 4) MEF2 synergizes with the thyroid hormone receptor to regulate transcription of the α-MHC gene (Lee et al., 1997) and thyroid hormone is a potent inducer of hypertrophy.

Transcriptional activation of the orphan steroid receptor Nur77 gene (NGFI-B) in T cells in response to T cell receptor activation is mediated by a CsA-sensitive, calcium-dependent signaling pathway (Woronicz et al., 1995). This signaling pathway is directed at two MEF2 binding sites in the NGFI-B promoter. There is no change in DNA binding activity of MEF2 in the presence or absence of calcium signals in that system, whereas transcriptional activity of MEF2 is dramatically increased by calcium signaling. This implies that calcium signals must enhance MEF2 activity by inducing a cofactor or a posttranslational modification of MEF2 that stimulates transcriptional activity.

In addition, transcription of the calcium-dependent lytic cycle switch gene BZLF1, which is required for induction of the lyric cycle of Epstein-Barr virus (EBV), is inhibited by CsA and FK506, indicating that a calcineurin-dependent pathway mediates activation of this gene (Liu et al, 1997). CsA-sensitivity of BZLF1 transcription maps to three MEF2 sites in the BZLF1 promoter. CsA-sensitive inducibility was shown to be reconstituted using an artificial promoter containing multiple copies of the MEF2 site in conjunction with a CREB/AP-1 site. NFAT did not bind the BZLF1 promoter, but CsA-sensitive induction of this promoter was shown to be calcineurin- and NFAT-dependent. CaMKIV was also shown to be a potent inducer of MEF2 activity (Liu et al., 1997). The mechanism whereby MEF2 confers responsiveness to the calcineurin/NFAT signaling system remains to be elucidated, however.

The MAP kinase signaling pathway also has been shown to lead to enhanced transcriptional activity of MEF2 factors in a variety of cell types (Han et al., 1997; Coso et al., 1997; Kato et al., 1997; Clarke et al., 1998). This enhancement has been shown for MEF2C to be mediated by phosphorylation of three amino acids, Thr293, Thr300, and Ser387, in the C-terminal activation domain by the MAP kinase family member p38. Whether these same residues are phosphorylated by hypertrophic signaling in the heart remains to be determined.

It is clear that the cardiac hypertrophic response is somehow initiated through a $Ca^{2+}$ dependent pathway. However, the precise identification of the gene(s) which mediate(s) the hypertrophic response remains elusive. The present invention is directed toward the elucidation of the exact point in the hypertrophic pathway which may be manipulated to achieve beneficial effects on cardiac hypertrophy. In order to develop pharmacologic strategies for treatment of cardiac hypertrophy in humans, it will be important to establish experimental models which accurately reflect the pathological profile of the disease and to identify compositions which regulate or inhibit hypertrophic growth.

SUMMARY OF THE INVENTION

Cardiac hypertrophy is an adaptive response of the heart to virtually all forms of cardiac disease. While the hypertrophic response is initially a compensatory mechanism that augments cardiac output, sustained hypertrophy can lead to dilated cardiomyopathy, heart failure, and sudden death. In the United States, approximately half a million individuals are diagnosed with heart failure each year, with a mortality rate approaching 50%. Thus, the need exists for methods and compositions that prevent or even reverse the effects of cardiac hypertrophy.

The present invention is directed toward the elucidation of the exact point in the hypertrophic pathway which may be manipulated to achieve beneficial effects on cardiac hypertrophy. Thus, in certain embodiments, the invention provides a method for identifying an inhibitor of cardiac hypertrophy, comprising providing a source of HDAC 4 or HDAC 5 enzyme, contacting the enzyme with a candidate substance, determining the enzyme function in the presence of the candidate substance and comparing the enzyme function in the absence of the candidate substance, wherein increased enzyme function in the presence of the candidate substance, as compared to enzyme function in the absence of the candidate substance, identifies the candidate substance as an inhibitor of cardiac hypertrophy. In certain embodiments, the enzyme is purified a HDAC 4, a purified HDAC 5 or a mixture of HDAC 4 and HDAC 5. In other embodiments, the HDAC enzyme is a mixture of HDAC 4 and HDAC 5, wherein the mixture is in a cardiac cell. In yet other embodiments, the HDAC 4 and HDAC 5 enzyme mixture in a cardiac cell is in an experimental animal.

In particular embodiments, the enzyme function of purified HDAC 4 or HDAC 5 is determined by an in vitro deacetylation reaction. In other embodiments, the enzyme function of an HDAC 4 and HDAC 5 mixture is determined by the histone acetylation state in a cardiac cell or a cardiac cell in an experimental animal. Also provided are methods of producing such an inhibitor, as well as inhibitors produced according to such methods.

In another embodiment of the invention, a method for identifying a modulator of gene expression in cardiac cells is contemplated. This method comprises providing a MEF2 HDAC binding region, contacting the MEF2 HDAC binding region with an HDAC 4 or 5 MEF2 binding region and a candidate substance and determine the binding of the MEF2 HDAC binding region in the presence and absence of the candidate substance, wherein a difference between binding in the presence and absence of the candidate substance identifies the candidate substances as a modulator of cardiac gene expression. In certain embodiments, the MEF2 HDAC binding region comprises residues 1-86. In other embodiments, the MEF2 HDAC binding region comprises residues 1-117. In another embodiment, the MEF2 HDAC binding region comprises full length MEF2. In other embodiments, the HDAC 4 or 5 MEF2 binding region comprises residues 163-180 of HDAC 4 or residues 175-192 of HDAC 5. In yet other embodiments, the HDAC 4 or 5 MEF2 binding region comprises full length HDAC.

In certain embodiments, the MEF2 HDAC binding region and HDAC 4 or 5 MEF2 binding regions contain, individually, a quenchable marker and a quenching agent. In other embodiments, the HDAC 4 or 5 MEF2 binding region is fused to a transcription factor, and the binding is measured by transcriptional activation of a reporter expression cassette. In still other embodiments, the reporter cassette encodes a detectable marker selected from the group consisting of β-galactosidase, lacZ and GFP luciferase.

The present invention provides further, a method for treating cardiac hypertrophy in an animal comprising providing at least one of HDAC 4 or 5 to cardiac tissue in the animal. The animal may be a human. In other embodiments both HDAC 4 and 5 are provided to cardiac tissue in the animal. In certain embodiments, at least one of HDAC 4 or 5 is provided by transferring an expression cassette encoding HDAC 4 or HDAC 5, under the control of a promoter active in cardiac tissue, into the cardiac tissue. In another embodiment, the expression cassette is a viral expression vector and transferring is achieved by infection of the cardiac tissue with a viral particle containing the viral expression vector. In particular embodiments, the viral expression vector is derived from adenovirus, retrovirus, adeno-associated virus, herpesvirus or vaccinia virus. In other embodiments of the invention, methods for treating cardiac hypertrophy further comprise the step of administering a traditional coronary heart disease drug formulation to the animal, such as for example, "beta blockers", anti-hypertensives, cardiotonics, anti-thrombotics, vasodilators, hormone antagonists, endothelin antagonists, cytokine inhibitors/blockers, calcium channel blockers, phosphodiesterase inhibitors and angiotensin type 2 antagonists.

In certain embodiments, a method for treating cardiac hypertrophy in an animal comprising providing a HDAC 4 or 5 agonist to said animal. In particular embodiments, the agonist increases HDAC 4 or 5 synthesis or the agonist increases HDAC 4 or 5 stability or the agonist increase HDAC 4 or 5 activity or any combination of therefor. In another embodiment, a method for treating cardiac hypertrophy in an animal further comprises the step of administering a traditional coronary heart disease drug formulation to the animal.

The present invention provides in certain embodiments, a method for identifying a subject at risk of developing cardiac hypertrophy comprising obtaining a biological sample from said subject and assessing an HDAC 4 or 5 genotype in cells of the sample. In particular embodiments, assessing comprises determining an HDAC 4 or 5 polynucleotide sequence, wherein the polynucleotide sequence is a coding sequence. In another embodiment, assessing comprises determining an HDAC 4 or 5 RFLP pattern. In yet another embodiment, assessing comprises determining the size of an HDAC 4 or 5 transcript or gene, wherein assessing may further comprises amplifying an HDAC 4 or 5 transcript or gene. In preferred embodiments, the biological sample is cardiac tissue.

In other embodiments of the invention, an inhibitor of cardiac hypertrophy is identified according to a method comprising providing a source of HDAC 4 or 5 enzyme, contacting the enzyme with a candidate substance, determining the enzyme function in the presence of the candidate substance, comparing the enzyme function in the absence of the candidate substance, wherein reduced enzyme function in the presence of the candidate substance, as compared to enzyme function in the absence of the candidate substance identifies the candidate substance as an inhibitor of cardiac hypertrophy and producing the inhibitor so identified.

The present invention provides in another embodiment, a method for identifying a modulator of gene expression in cardiac cells comprising providing a MEF2 HDAC binding region, contacting the MEF2 HDAC binding region with an HDAC 4 or 5 MEF2 binding region and a candidate substance, determining the binding in step of the HDAC 4 or 5 MEF2 binding region and a candidate substance, comparing the binding in the absence of the candidate substance, wherein a difference between binding in the presence and absence of the candidate substance identifies the candidate substances as a modulator of cardiac gene expression and producing the modulator so identified.

In other embodiments, a non-human transgenic animal is provided lacking one or more functional alleles of HDAC 4 or 5. In particular embodiments, the non-human transgenic animal lacks all functional alleles of HDAC 4 and 5. In yet other embodiments, the non-human transgenic animal is selected from the group consisting of mouse, rat, rabbit, sheep, goat and cow and may further comprise a detectable marker gene under the control of MEF2 regulated promoter. In certain embodiments, the MEF2 regulated promoter is a NGFI-B promoter and the detectable marker gene is β-galactosidase, GFP or luciferase.

In still further embodiments, there is provided a method of identifying a modulator of HDAC phosphorylation comprising (a) providing a source of an HDAC under conditions supporting phosphorylation of said HDAC; (b) contacting said HDAC with a candidate substance; (c) determining the phosphorylation state of one or more serine residues in said HDAC; and (d) comparing the phosphorylation state of the HDAC of step (c) with an HDAC in the presence of a candidate substance, wherein a change in the phosphorylation state of said HDAC in the presence of said candidate substance, as compared to enzyme function in the absence of said candidate substance, identifies said candidate substance as a modulator of HDAC phosphorylation.

The HDAC may be HDAC 4 or 5. Where HDAC 5, the serine residues may be selected from the group consisting of 259, 498 and 661. The phosphorylation state may be determined by said HDAC binding to 14-3-3, for example, wherein HDAC binding to 14-3-3 is determined by the ability of a GAL4 fusion of HDAC and a GAL4 fusion of 14-3-3 to initate transcription of a marker gene. The marker gene may be β-galactosidase, green fluorescent protein or luciferase. The HDAC may be located in a host cell, for example, a yeast cell. Alternatively, the phosphorylation state may be determined by determining subcellular localization of HDAC. Also provided are methods of preparing such modulators and modulators prepared by such methods.

Also provided is a method for treating cardiac hypertrophy in an animal comprising providing an inhibitor of HDAC phosphorylation to an animal. The is may be a human. The inhibitor may be an inhibitor of Cam kinase, such as KN62. The method may further comprise providing a second pharmaceutical composition to said animal, for example, "beta blockers", anti-hypertensives, cardiotonics, anti-thrombotics, vasodilators, hormone antagonists, endothelin antagonists, cytokine inhibitors/blockers, calcium channel blockers, phosphodiesterase inhibitors and angiotensin type 2 antagonists. The HDAC may be HDAC 4 or HDAC 5.

In another embodiment, there is provided a method of identifying a HDAC kinase comprising (a) providing an HDAC-GAL4 fusion and a 14-3-3-GAL4 fusion in host cells that do not phosphorylate serine residues of HDAC, wherein said host cell further comprises a marker gene under the control of a promoter that is induced by GAL4; (b) transforming the host cells of step (a) with a cDNA library; and (c) determining expression of said marker gene, wherein expression of said marker gene by a cell identifies that cell as containing a cDNA that encodes an HDAC kinase. The HDAC may be HDAC 4 or HDAC 5.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 7. Histological cross-sections of hearts of wild-type and aMHC-CaMKIV mice. Nontransgenic and aMHC-CaMKIV transgenic mice were sacrificed at 8 weeks of age and hearts were sectioned and stained with H&E. There is at least a 2-fold enlargement of the heart in the aMHC-CaMKIV line. lv, left ventricle; rv, right ventricle.

FIG. 8. Hearts from MEF2 indicator mice stained for lacZ. The heart on the left is from a normal mouse and on the right from a mouse bearing an activated CaMKIV transgene expressed specifically in the heart under control of the α-myosin heavy chain promoter. LacZ expression is activated specifically in the CaMKIV transgenic heart, demonstrating that MEF2 activation is a downstream step in the CaMKIV signaling pathway in vivo.

FIG. 9A and FIG. 9B. Localization of the MEF2-interaction region of HDACs 4 and 5 with the yeast two-hybrid system. A) Schematic diagrams of the MEF2 baits used in two-hybrid screens; GAL4-MEF2(1-86) and MEF2(1-117)-GAL4. (B) Schematic diagrams of HDACs 4 and 5 and the different regions of the proteins encoded by cDNAs rescued as "prey" in two-hybrid screens. The rescued HDAC cDNAs overlap in an 18 amino acid region in their amino-terminal variable regions (residues 163-180 and 175-192 of HDAC 4 and 5, respectively), shown in black. The HDAC catalytic domain is located at the extreme C-termini of the proteins.

FIG. 10. Schematic diagram of HDAC proteins. Six different HDACs have been cloned from vertebrate organisms. All share homology in a the catalytic region. HDACs 4 and 5 have a unique amino-terminal extension not found in other HDACs. This amino-terminal region contains the MEF2-binding domain.

FIG. 12. Coimmunoprecipitation of HDACs 4 and 5 with MEF2 factors in vivo. Cos cells were transiently transfected with expression vectors encoding HDACs with a Flag epitope, as indicated, and MEF2 A, C, or D. Cells were then lysed and extracts immunoprecipitated with anti-Flag antibody, followed by anti-MEF2 or anti-Flag western blot. The top panel shows the results of anti-MEF2 western blots. HDACs 4 and 5, but not HDACs 1 or 3, interact with each MEF2 factor. The bottom panel shows the results of anti-Flag western blots and demonstrates the presence of comparable amounts of exogenous HDAC protein in each extract. A schematic diagram of the experiment is shown at the bottom.

FIG. 13. Coimmunoprecipitation of HDAC 5 with MEF2C requires the N-terminus of HDAC 5. Cos cells were transiently transfected with expression vectors encoding HDAC 4, HDAC 5 or a deletion mutant lacking the N-terminus (HDAC 5-ΔN) with a Flag epitope and MEF2C. Cells were then lysed and extracts immunoprecipitated with anti-Flag antibody, followed by anti-MEF2 western blot. The top panel shows the results of anti-Flag immunoprecipitation followed by anti-MEF2 western blot. The bottom panel shows the results of anti-MEF2 western blot without an immunoprecipitation reaction and demonstrates the presence of comparable amounts of exogenous HDAC protein in each extract. A schematic diagram of the experiment is shown at the bottom.

Once phosphorylated, HDAC 5 engages 14-3-3 in the nucleus which then results in nuclear export to the cytoplasm. An HDAC 5 phosphatase presumably removes phosphate groups from key residues on HDAC 5 in the cytoplasm, resulting in reentry of the protein to the nucleus. This pathway identifies multiple regulatory points for the control of MEF2 activation via HDAC phosphorylation and 14-3-3 interactions.

Figure 22:
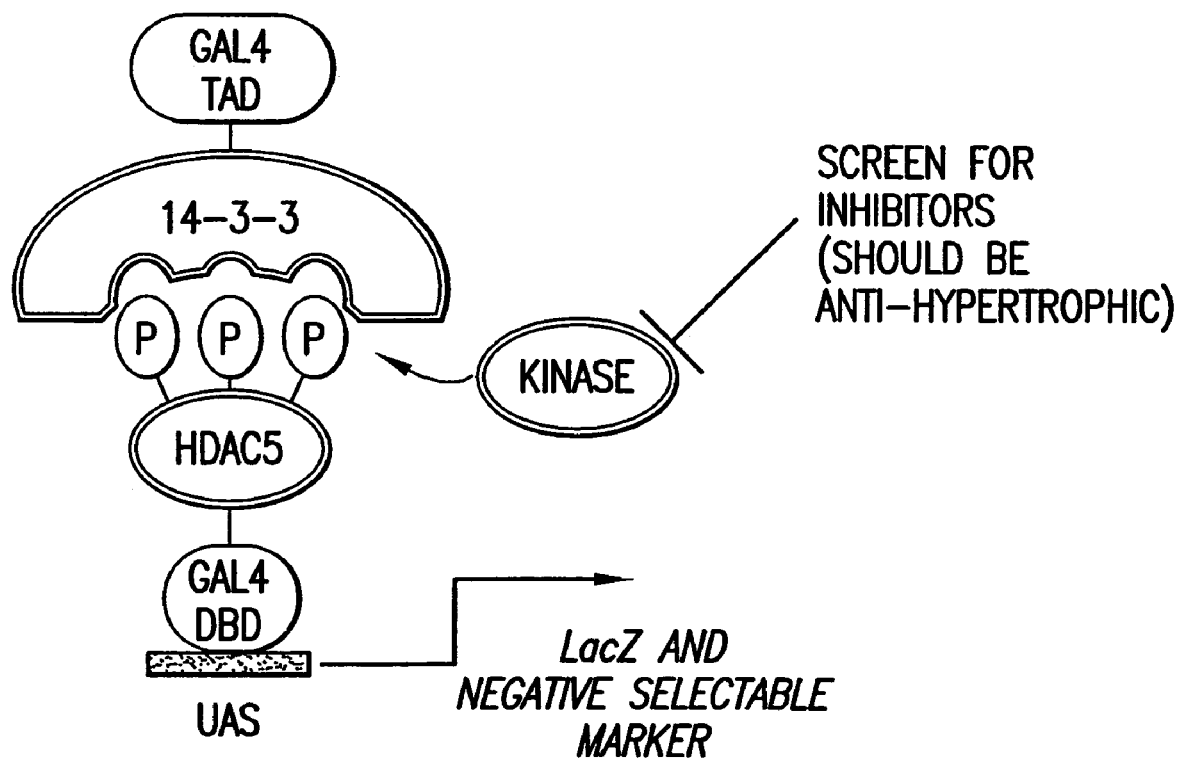

FIG. 22. Schematic diagram of an assay to detect inhibitors of hypertrophic signaling and MEF2 activation. According to this assay, HDAC 5 is fused to the DNA binding domain of GAL4. This construct is expressed in yeast that harbor integrated reporter genes for LacZ and other positive or negative selectable markers. A second construct is created in which 14-3-3 is fused to the activation domain of GAL4. Expression of this construct in yeast fails to activate the integrated marker genes because it cannot engage unphosphorylated HDAC 5-GAL4. This yeast strain is then used to screen for HDAC kinases which, upon phosphorylation of HDAC 5, will enable it to engage 14-3-3, resulting in activation of selectable markers. Such kinases can then be screened for chemical inhibitors which would prevent protein-protein interaction between 14-3-3 and HDAC 5 as a consequence of inhibition of phosphorylation. Such inhibitors would be predicted to act as inhibitors of cardiac hypertrophy.

DESCRIPTION OF ILLUSTRATIVE EMBODIMENTS

Cardiac hypertrophy, which results in heart failure, is a major cause of morbidity in the United States, but the underlying molecular mechanisms are not understood. Hypertrophic cardiomyopathy occurs in both familial and sporadic forms. This type of cardiomyopathy is characterized by hypertrophy of the left ventricle. Hypertrophic cardiomyopathy is characterized by enhanced systolic function, a prolonged and abnormally powerful isometric contraction phase followed by impaired relaxation and increased chamber stiffness during diastole.

Cardiac hypertrophy in response to an increased workload imposed on the heart is a fundamental adaptive mechanism. It is a specialized process reflecting a quantitative increase in cell size and mass (rather than cell number) as the result of any or a combination of neural, endocrine or mechanical stimuli. Hypertension, another factor involved in cardiac hypertrophy, is a frequent precursor of congestive heart failure. When heart failure occurs, the left ventricle usually is hypertrophied and dilated and indices of systolic function, such as ejection fraction, are reduced. Clearly, the cardiac hypertrophic response is a complex syndrome and the elucidation of the pathways leading to cardiac hypertrophy will be beneficial in the treatment of heart disease resulting from a various stimuli.

A family of transcription factors, the monocyte enhancer factor-2 family (MEF2), are involved in cardiac hypertrophy. For example, a variety of stimuli can elevate intracellular calcium, resulting in a cascade of intracellular signalling systems or pathways, including calcineurin, CAM kinases, PKC and MAP kinases. All of these signals activate MEF2 and result in cardiac hypertrophy. However, it is still not completely understood how the various signal systems exert their effects on MEF2 and modulate its hypertrophic signaling. The present invention has identified two histone deacetylase proteins, HDAC 4 and HDAC 5, involved in modulating MEF2 activity.

Six different HDACs have been cloned from vertebrate organisms. All share homology in a the catalytic region. HDACs 4 and 5 however, have a unique amino-terminal extension not found in other HDACs. This amino-terminal region contains the MEF2-binding domain. Histone acetylases and deacetylases play a major role in the control of gene expression. The balance between activities of histone acetylases (HA) and deacetylases (HDAC) determines the level of histone acetylation. Consequently, acetylated histones cause relaxation of chromatin and activation of gene transcription, whereas deacetylated chromatin is generally transcriptionally inactive. The inventors have demonstrated in the present invention, that HDAC 4 and 5 dimerize with MEF2 and repress the transcriptional activity of MEF2. Further, this interaction requires the presence of the N-terminus of the HDAC 4 and 5 proteins.

Thus, in certain embodiments, the present invention provides methods and compositions to identify inhibitors of cardiac hypertrophy, using HDAC 4 and 5 proteins. In particular embodiments, the invention provides methods and compositions to identify modulators of cardiac cell gene expression. In other embodiments, the invention provides methods of identifying a subject at risk of developing cardiac hypertrophy and provides a non-human transgenic animal lacking one or more functional alleles of HDAC 4 or 5.

A. A Transcriptional Pathway for Cardiac Hypertrophy

It is well established that elevation in intracellular $Ca^{2+}$ is associated with the initiation of mechanical or agonist-induced cardiac hypertrophy (Marban et al, 1987; Bustamante et al., 1991; Hongo et al., 1995; Le Guennec et al., 1991; Perreault et al., 1994; Saeki et al., 1993). Further, it is known that cardiac hypertrophy results from the up-regulation of certain genes, which leads to an increase in the protein content of cardiomyocytes with little or no increase in the number of cells. Activation of this hypertrophic pathway results in molecular and pathophysiologic changes.

As stated above, it is known that $Ca^{2+}$ activation is involved in cardiac hypertrophy. The present invention describes a pathway for cardiac hypertrophy, in which MEF2 transcriptional activity is modulated by histone deacetylase proteins HDAC 4 and 5. The individual components of this pathway as they relate to cardiac hypertrophy are discussed in further detail herein below.

1. Calcineurin

Calcineurin is a ubiquitously expressed serine/threonine phosphatase that exists as a heterodimer, comprised of a 59 kD calmodulin-binding catalytic A subunit and a 19 kD $Ca^{2+}$-binding regulatory B subunit (Stemmer and Klee, 1994; Su et al., 1995). Calcineurin is uniquely suited to mediate the prolonged hypertrophic response of a cardiomyocyte to $Ca^{2+}$ signaling because the enzyme is activated by a sustained $Ca^{2+}$ plateau and is insensitive to transient $Ca^{2+}$ fluxes as occur in response to cardiomyocyte contraction (Dolmetsch et al., 1997).

Activation of calcineurin is mediated by binding of $Ca^{2+}$ and calmodulin to the regulatory and catalytic subunits, respectively. Previous studies showed that over-expression of calmodulin in the heart also results in hypertrophy, but the mechanism involved was not determined (Gruver et al., 1993). Given the observations presented herein, it is now clear that calmodulin acts through the calcineurin pathway to induce the hypertrophic response.

2. CAMK

There is substantial evidence suggesting that the intracellular $Ca^{2+}$-binding protein, calmodulin, may be a key regulator of cardiac hypertrophy. For example, overexpression of calmodulin in the hearts of transgenic mice induces hypertrophy (Gruver et al., 1993), and treatment of cultured cardiomyocytes with the calmodulin antagonist W-7 prevents hypertrophy in response to α-adrenergic stimulation and Ca$^{2+}$ channel agonists (Sei et al., 1991). Calcineurin and the multifunctional Ca$^{2+}$/calmodulin-dependent protein kinase (CaMK) are well characterized downstream targets of calmodulin regulation. Indeed, activated CaMKII has been shown to induce the hypertrophic-responsive gene atrial natriuretic factor (ANF) in primary cardiomyocytes in vitro and the CaMK inhibitor KN-93 can block the hypertrophic response to endothelin-1 in vitro (Ramirez et al., 1997; Sei et al., 1991; McDonough and Glembotski, 1992). However, the dB isoform of CaMKII, which is the predominant isoform of CaMKII expressed in the heart, does not activate the complete hypertrophic response in vitro and the potential involvement of this signaling pathway in hypertrophic growth vivo has not been investigated. Recently, CaM kinase activity was also reported to be elevated in human failing hearts (Hoch et al., 1999).

Because of the suggested importance of Ca$^{2+}$/calmodulin in cardiac hypertrophy, and the evidence for calcineurin-independent mechanisms for hypertrophy, the relationship of calcineurin and CaM kinase signaling in cardiomyocytes was investigated. The inventors have shown that activated CaMKI and CaMKIV can induce the hypertrophic response in primary neonatal cardiomyocytes, whereas CaMKII inhibits this response. CaMKI and IV also synergize with calcineurin-NFAT to stimulate hypertrophy in vivo and in vitro. These results reveal specificity in CaM kinase signaling in the heart and suggest that the Ca$^{2+}$/calmodulin-dependent signaling pathways controlled by CaMKIV and calcineurin act cooperatively and likely converge on distinct sets of downstream transcription factors to evoke the hypertrophic response.

There are six types of known CaM kinases, CaM kinase I, II, III, and IV, myosin light chain kinase, and phosphorylase kinase. The CaM kinases share a common structural organization, with an amino-terminal catalytic domain and a central calmodulin-binding regulatory domain (reviewed in Soderling, 1999). CaMKI and CaMKIV share similar catalytic and structural properties. Both isoforms are localized to the nucleus and exist as monomers and both activate the hypertrophic response in primary neonatal cardiomyocytes. CaMKI is expressed in a wide range of tissues, including the heart, whereas CaMKIV is expressed predominantly in brain, testis, spleen and thymus. Present results show that CaMKIV is also expressed in heart, although at lower levels than in these other tissues.

3. MEF2

A family of transcription factors, the monocyte enhancer factor-2 family (MEF2), are known to play an important role in morphogenesis and myogenesis of skeletal, cardiac, and smooth muscle cells (Olson et al., 1995). MEF2 factors are expressed in all developing muscle cell types, binding a conserved DNA sequence in the control regions of the majority of muscle-specific genes. Of the four mammalian MEF2 genes, three (MEF2A, MEF2B and MEF2C) can be alternatively spliced, which have significant functional differences (Brand, 1997; Olson et al., 1995). These transcription factors share homology in an N-terminal MADS-box and an adjacent motif known as the MEF2 domain. Together, these regions of MEF2 mediate DNA binding, homo- and heterodimerization, and interaction with various cofactors, such as the myogenic bHLH proteins in skeletal muscle. Additionally, biochemical and genetic studies in vertebrate and invertebrate organisms have demonstrated that MEF2 factors regulate myogenesis through combinatorial interactions with other transcription factors.

Loss-of-function studies indicate that MEF2 factors are essential for activation of muscle gene expression during embryogenesis. The expression and functions of MEF2 proteins are subject to multiple forms of positive and negative regulation, serving to fine-tune the diverse transcriptional circuits in which the MEF2 factors participate. The present invention describes methods for determining the role(s) of MEF2 in the development of cardiac hypertrophy.

4. HDAC 4 and HDAC 5

Nucleosomes, the primary scaffold of chromatin folding, are dynamic macromolecular structures, influencing chromatin solution conformations (Workman and Kingston, 1998). The nucleosome core is made up of histone proteins, H2A, HB, H3 and H4. Histone acetylation causes nucleosomes and nucleosomal arrangements to behave with altered biophysical properties. The balance between activities of histone acetylases (HA) and deacetylases (HDAC) determines the level of histone acetylation. Acetylated histones cause relaxation of chromatin and activation of gene transcription, whereas deacetylated chromatin generally is transcriptionally inactive.

Six different HDACs have been cloned from vertebrate organisms. The first three human HDACs identified were HDAC1, HDAC2 and HDAC3 (termed class I human HDACs). Recently class II human HDACs, HDAC 4, HDAC 5, HDAC6 and HDAC7 (Kao, et al, 2000) have been cloned and identified (Grozinger et al., 1999, incorporated herein by reference). All share homology in a the catalytic region. HDACs 4 and 5 however, have a unique amino-terminal extension not found in other HDACs. This amino-terminal region contains the MEF2-binding domain. The present invention has identified HDACs 4 and 5 as being involved in the regulation of cardiac gene expression and in particular embodiments, repressing MEF2 transcriptional activity. The exact mechanism in which HDAC 4 and HDAC 5 repress MEF2 activity is not completely understood. One possibility is that HDAC 4 or 5 binding to MEF2 inhibits MEF2 transcriptional activity, either competitively or by destabilizing the native, transcriptionally active MEF2 conformation. It is possible also, that HDAC 4 or 5 require dimerization with MEF2 to localize or position HDAC in a proximity to histones for deacetylation to proceed.

5. Hypertrophic Genes

In response to hormonal, genetic and mechanical stimuli, the myocardium adapts to increased workloads through the hypertrophy of individual muscle cells (Morgan et al. 1987). Because the adult myocardial cell is terminally differentiated and has lost the ability to proliferate, cardiac growth during the hypertrophic process results primarily from an increase in protein content per individual myocardial cell, with little or no change in muscle cell number. Thus, the central features of the myocardial hypertrophic response are increase in contractile protein content, the induction of contractile protein isoforms and the expression of embryonic markers, which appear to depend largely on the activation of transcription of the corresponding cardiac gene that encode these proteins.

Up-regulation of contractile protein genes constituitively expressed in the myocardium, such as the rat cardiac myosin light chain-2 (MLC-2) gene, results in a quantitative increase in MLC-2 levels and a corresponding accumulation of this contractile protein in individual myocardial cells. Myocardial cell hypertrophy also is associated with qualitative changes in contractile protein composition, including the induction of contractile protein genes that are normally expressed in embryonic development, e.g., the reactivation of skeletal α-actin (Schwartz et al. 1986) and β-myosin heavy-chain (MHC) expression in rodent and rabbit models of cardiac hypertrophy. In addition to the induction of specific contractile protein components, ventricular hypertrophy is also characterized by alterations in the expression of noncontractile protein genes.

Of the known noncontractile protein genes that are up-regulated during ventricular hypertrophy, the reactivation of atrial natriuretic factor (ANF) expression may be the best characterized. ANF is a vasoregulatory peptide hormone which is secreted by atrial myocytes, is stored within secretory granules which undergo exocytosis in response to stretch of the tissue, or to hormones such as catecholamines or endothelin (ET). The β-type natriuretic peptide (BNP), which decrease blood pressure by vasodilation and natriuresis, also is rapidly upregulated in the heart in response to hypertrophic signals (reviewed in Komuro and Yazaki, 1993).

B. Treatment of Heart Disease

Though there have been reports that a $Ca^{2+}$ mediated pathway is involved in certain heart disease, the present invention provides evidence of MEF2 as a central mediator of the hypertrophic response. Essentially, the $Ca^{2+}$-dependent protein calcineurin and CaMKIV can activate MEF2-dependent gene expression. Further it is demonstrated by the inventors, that the histone deacetylases HDAC 4 and 5 are involved in regulating cardiac hypertrophy. It is contemplated in the present invention that HDAC 4 and 5 modulate MEF2 transcriptional activity via association with an identified HDAC 4 and 5 MEF2 binding domain.

1. Activation of HDAC 4 and 5

In a particular embodiment of the present invention, there are provided methods for the treatment of cardiac hypertrophy. These methods exploit the inventors' observation that HDAC 4 and 5 interact with MEF2, and down-regulate the expression of genes involved in the hypertrophic response. Thus, an increase in HDAC 4 and 5 protein concentration, or an agnostic that enhances HDAC 4 or 5 activity, expression or stability is contemplated to suppress hypertrophic cellular growth.

At its most basic, this embodiment will function in vivo by reducing expression of genes involved in hypertrophic signaling in individuals suspected of having undergone a hypertrophic response, currently undergoing a hypeitrophic response, or in danger of cardiac hypertrophy. This may be accomplished by one of several different mechanisms. First, one may a provide a HDAC 4 or 5 protein preparation or expression cassette encoding HDAC 4 or 5, wherein HDAC 4 or 5 down regulates the expression of hypertrophic genes. Second, one may directly stimulate or stabilize the function of the HDAC 4 or 5 protein by providing an agent or agonist that binds to a HDAC 4 or 5 protein. The screening for modulators of cardiac hypertrophy and more particularly, modulators of HDAC 4 and 5 activity are described in Section C.

The therapeutic compositions of the present invention may be administered in a manner similar to (and in conjunction with) the administration of current treatments for heart conditions, such as aspirin, nitrates and beta blockers. Thus, the therapeutic formulations can be for oral administration in a tablet form to be swallowed (such as with aspirin) or to be dissolved under the tongue (such as with nitrates). These medicaments also can be provided as a patch to be worn on the skin, or as a topical cream to be applied to the skin. In other instances, the therapeutic compositions of the present invention may be provided as an expression cassette and administered via methods of gene transfer.

2. Blocking the Function of MEF2

In another embodiment, it may be desirable to block the function of a MEF2 polypeptide alone or in combination with HDAC 4 and 5. This can be accomplished by use of organochemical compositions that interfere with the function of MEF2 or through the activation of an HDAC as described above. With respect to organochemical inhibitors MEF2 or activators of HDAC 4 and 5, such compounds may be identified in standard screening assays, as described in the following section. Once identified, such a compound may be used to inhibit MEF2 function or activate HDAC 4 and 5 function in a therapeutic context.

3. Blocking of HDAC Phosphorylation

As discussed below, the inventors have identified specific residues in HDAC that are phosphorylated. Depending on the phosphorylation state, HDAC is localized to the nucleus, binds MEF2, and inhibits cardiac hypertrophic signals (unphosphorylated), or instead binds to the chaperone protein 14-3-3, and is exported to the cytoplasm (phosphorylated). Thus, it is clear that the ability to inhibit phosphorylation of HDAC is an important step in blocking MEF2-dependent hypertrophic signals, and hence, impeding development of cardiac hypertrophy.

Thus, is one aspect of the present invention, there is provided a method of treating or preventing cardiac hypertrophy in an animal. The invention comprises providing to the animal an inhibitor of HDAC phosphorylation. KN62 is a known drug that inhibits Cam kinases. Other compositions may be useful in this endeavor and include, but are not limited to, phosphorylases, that counteract the action of kinases acting on HDACs, small portions of HDAC that mimic the phosphorylation site of HDAC, single chain antibodies that mimic HDAC, or other "mimetics."

4. Combined Therapy

In many clinical situations, it is advisable to use a combination of distinct therapies. Thus, it is envisioned that, in addition to the therapies described above, one would also wish to provide to the patient more "standard" pharmaceutical cardiac therapies. Examples of standard therapies include so-called "beta blockers", anti-hypertensives, cardiotonics, anti-thrombotics, vasodilators, hormone antagonists, endothelin antagonists, cytokine inhibitors/blockers, calcium channel blockers, phosphodiesterase inhibitors and angiotensin type 2 antagonists. Also envisioned are combinations with pharmaceuticals identified according to the screening methods described herein.

Combinations may be achieved by contacting cardiac cells with a single composition or pharmacological formulation that includes both agents, or by contacting the cell with two distinct compositions or formulations, at the same time, wherein one composition includes the expression construct and the other includes the agent. Alternatively, gene therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either (a) an HDAC agonsist, an MEF2 antagonist, or an inhibitor of HDAC phosphorylation, or (b) the other agent will be desired. Various combinations may be employed, where is an HDAC agonsist, an MEF2 antagonist, or an inhibitor of HDAC phosphorylation, "A" and the other agent is "B", as exemplified below:

1 A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations are contemplated as well.

C. Screening for Modulators of Cardiac Hypertrophy

The present invention also contemplates the screening of compounds for their ability to inhibit cardiac hypertrophy. The ability of the present inventors to create cellular, organ and organismal systems which mimic this disease provide an ideal setting in which to test various compounds for therapeutic activity. Particularly preferred compounds will be those useful in inhibiting cardiac hypertrophy and preventing or reversing heart disease. In the screening assays of the present invention, the candidate substance may first be screened for basic biochemical activity—e.g. binding to a target molecule—and then tested for its ability to inhibit a hypertrophic phenotype, at the cellular, tissue or whole animal level.

1. Screening Inhibitors of Cardiac Hypertrophy

The present invention provides methods of screening for inhibitors of cardiac hypertrophy. It is contemplated that this screening techniques will prove useful in the identification of compounds that will block cardiac hypertrophy and/or reduce cardiac hypertrophy once developed. In particular embodiments, screening assays may be performed in vitro, in cyto or in vivo. Suitable host cells include yeast, fibroblasts and cardiac cells.

In one embodiment, the present invention is directed to a method for determining the ability of a candidate substance to inhibit hypertrophy, generally including the steps of:

(a) providing a source of HDAC 4 or HDAC 5 enzyme;
(b) contacting the enzyme with a candidate substance;
(c) determining the enzyme function in step (b); and
(d) comparing the enzyme function in step (c) with the enzyme function of the enzyme in the absence of the candidate substance, wherein increased enzyme function in the presence of the candidate substance, as compared to enzyme function in the absence of the candidate substance, identifies the candidate substance as an inhibitor of cardiac hypertrophy.

In another embodiment, a method for identifying a modulator of gene expression in cardiac cells is provided, generally including the following steps:

(a) providing a MEF2 HDAC binding region;
(b) contacting the MEF2 HDAC binding region with an HDAC 4 or 5 MEF2 binding region and a candidate substance;
(c) determining the binding in step (b); and
(d) comparing the binding in step (c) with the binding of MEF2 HDAC binding region and HDAC 4 or 5 MEF2 binding region in the absence of the candidate substance, wherein a difference between binding in the presence and absence of the candidate substance identifies the candidate substances as a modulator of cardiac gene expression.

Upon identification of an effective candidate substance as an inhibitor of cardiac hypertrophy or as a modulator of cardiac gene expression, a further step such as producing the candidate substance could be implemented. The HDAC 4 or HDAC 5 enzyme in the present invention, may provided separately or as a mixture of the two. In addition, a particular screening system of candidate substances can be an in vitro or in vivo system, such as cardiac cells, cardiac tissue or in an experimental animal.

In a more specific embodiment, the present invention seeks to identify agents that inhibit phosphorylation of HDACs. The residues of interest include serines at 259, 498 and 661 of the HDAC 5 sequence (or comparable residues in other HDACs). Thus, one can use any method to examine the ability of a candidate substance to assess the phosphorylation state of these residues. In one particularly useful embodiment, there is provided a method utilizing a two-hybrid system. HDAC 5 and 14-3-3 each are fused to GAL4 transcription activation domain. In the presence of an active kinase that phosphorylates residues 259, 498 and/or 661, there will be association of the two hybrids and transcriptional activation of a marker (e.g., LacZ) gene. In the presence of an inhibitor of phosphorylation, transcriptional activation will be lost. In yeast, there is constitutive phosphorylation of 661.

The assay above can be used in a gene discovery mode as well. Yeast cells do not produce a kinase that is capable of phosphorylating residues 259 and 498. Thus, using a cDNA library, one can transfer different cDNA's into cells to determine which encode kinases capable of phosphorylating these residues. In the absence of phosphorylation, no transcription of the indicator will be observed. However, a cDNA that encodes a kinase that acts on these residues will result in binding of the HDAC 4 and 14-3-3 fusions and activation of transcription of the reporter gene. In this regard, it is preferred that the HDAC lack any constitutively phosphorylated residues such as Ser661.

Another screening method in the present invention can be used to identify subjects at risk of developing cardiac hypertrophy, generally including the following steps: obtaining a biological sample from said subject and assessing an HDAC 4 or 5 genotype in cells of said sample.

2. Assay Methods a. In Vitro Assays

A quick, inexpensive and easy assay to run is a binding assay. Binding of a molecule to a target may, in and of itself, be inhibitory, due to steric, allosteric or charge-charge interactions. This can be performed in solution or on a solid phase and can be utilized as a first round screen to rapidly eliminate certain compounds before moving into more sophisticated screening assays. In one embodiment of this kind, the screening of compounds that bind to the HDAC 4 or 5 molecule or fragment thereof is provided. In another embodiment, a MEF2 HDAC binding region is provided and the MEF2 HDAC binding region contacted with a HDAC 4 or HDAC 5 binding region in the presence or absence of a candidate substance.

The HDAC target protein or MEF2 HDAC target binding region may be either free in solution, fixed to a support, expressed in or on the surface of a cell. Either the target or the compound may be labeled, thereby permitting determining of binding. In another embodiment, the assay may measure the inhibition of binding of a target to a natural or artificial substrate or binding partner (such as HDAC 4 or 5). Competitive binding assays can be performed in which one of the agents is labeled. Usually, the target will be the labeled species, decreasing the chance that the labeling will interfere with the binding moiety's function. One may measure the amount of free label versus bound label to determine binding or inhibition of binding.

A technique for high throughput-screening of compounds is described in WO 84/03564. Large numbers of small peptide test compounds are synthesized on a solid substrate, such as plastic pins or some other surface. The peptide test compounds are reacted with, for example, HDAC 4 or 5 and washed. Bound polypeptide is detected by various methods.

Purified target, such as HDAC 4 or 5, can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link an active region (e.g., the C-terminus of MEF2) to a solid phase.

In other embodiments, it is necessary to determine the acetylated or deacetylated state of histone proteins to determine HDAC 4 or 5 enzymatic activity. This becomes particularly relevant when screening for candidate substances that inhibit cardiac hypertrophy.

The following techniques may be used to detect or assay acetylation or deacetylation. Such methods, when applicable, may be used for in vitro or in cyto assays. For example, a specific cell line may be treated with different concentrations of a candidate substance. Methods for measuring hyperacetylation of histones have been described in detail (Verdel and Khochbin, 1999; Fischle et al., 1999; Grozinger et al., 1999) and are known in the art. For example, the appearance of hyperacetylated H4 histone can be monitored using antibody raised against hyperacetylated histone H4 and detected by cytofluorimetric measurement of immunofluorescence (see, Van Lint et al., 1996). In another technique, cells are lysed, the histones purified and analyzed on a Triton/acid/urea gel. Analytical ultracentrifugation is often used also to detect histone acetylation.

Measuring the rate of deacetylation of [$^3$H]-labeled acetylated histones also is a useful assay in the present invention. For example, a candidate substance may be screened for agonistic effects on HDAC 4 or 5 activity using [$^3$H]-labeled acetylated histones. The released [$^3$H]acetate can be detected by methods of acetate extraction or the histones immunoprecipitated and the remaining [$^3$H]-labeled acetylated histone level measured.

b. In Cyto Assays

Various cell lines that exhibit cardiac hypertrophic characteristics can be utilized for screening of candidate substances. For example, cells containing engineered indicators, as discussed above, can be used to study various functional attributes of candidate compounds. In such assays, the compound would be formulated appropriately, given its biochemical nature, and contacted with a target cell.

Depending on the assay, culture may be required. As discussed above, the cell may then be examined by virtue of a number of different physiologic assays (growth, size, $Ca^{2+}$ effects). Alternatively, molecular analysis may be performed in which the function of MEF2, HDAC 4, HDAC 5 and related pathways may be explored. This involves assays such as those for protein expression, enzyme function, substrate utilization, mRNA expression (including differential display of whole cell or polyA RNA) and others.

In one aspect, the cells express an indicator gene under the control of various regulatory elements. These elements are regulated by MEF2 and provide a measure, through expression of the controlled indicator gene, of MEF2 transcriptional activator activity. Any regulatory element subject to MEF2 control may be utilized. Indicator genes include lacZ, GFP luciferase, β-galactosidase and other similar markers.

When assaying a subject for cardiac hypertrophy or one at risk for developing cardiac hypertrophy, a biological sample from the subject is obtaining and the HDAC 4 or 5 genotype in cells of the sample are assessed. The genetic analysis may comprise methods of sequencing the entire HDAC 4 or HDAC 5 polynucleotide sequence or the HDAC 4 or HDAC 5 polynucleotide coding sequence. Other assay methods that might be used for detecting HDAC gene sequences are RFLP patterns, determination of HDAC mRNA or gene size.

C. In Vivo Assays

The present invention particularly contemplates the use of various animal models. Here, transgenic animals have been created lacking one or more functional HDAC 4 or HDAC 5 alleles. In another embodiment, the animal further comprises a detectable marker gene under the control of a MEF2 regulated promoter.

Treatment of these animals with test compounds will involve the administration of the compound, in an appropriate form, to the animal. Administration will be by any route the could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply.

Determining the effectiveness of a compound in vivo involves examining the expression of the indicator gene.

2. Inhibitors of MEF2, Activators of HDAC 4 and 5, Inhibitors of HDAC Phosphorylation A MEF2 inhibitor according to the present invention may be one which exerts its inhibitory effect upstream or downstream of MEF2, or on MEF2 directly. Regardless of the type of inhibitor identified by the present screening methods, the effect of the inhibition by such a compound results in inhibition of the cardiac hypertrophy, or some related biochemical or physiologic aspect thereof, for example, growth, $Ca^{2+}$-dependent gene expression and the like in the absence of the added candidate substance. Similarly, a HDAC 4 or 5 activator according to the present is an agonist that exerts its effects on HDAC 4 or 5, wherein the result of activation is observed as an inhibition of cardiac hypertrophy. An inhibitor of HDAC phosphorylation may be specific or non-specific. It may directly impact the enzyme that is responsible for phosphorylation of HDAC, or it may induce a phosphorylase that removes phosphates from various (e.g., serine) residues on HDAC.

3. Candidate Substances

As used herein the term "candidate substance" refers to any molecule that may potentially inhibit cardiac hypertrophy. The candidate substance may be a protein or fragment thereof, a small molecule inhibitor, or even a nucleic acid molecule. It may prove to be the case that the most useful pharmacological compounds will be compounds that are structurally related to other known modulators of hypertrophy, such as cyclosporin A and FK506. Such an endeavor often is know as "rational drug design," and includes not only comparisons with know inhibitors, but predictions relating to the structure of target molecules.

The goal of rational drug design is to produce structural analogs of biologically active polypeptides or target compounds. By creating such analogs, it is possible to fashion drugs which are more active or stable than the natural molecules, which have different susceptibility to alteration or which may affect the function of various other molecules. In one approach, one would generate a three-dimensional structure for a molecule like HDAC 4 or 5, or a fragment thereof, thereby creating an agonist of HDAC 4 or 5, or an antagonist of HDAC 4 or 5 phosphorylation (i.e., a fragment of HDAC 4 or 5 containing one or more phosphorylation sites). Alternatively, one could generate a three-dimensional structure for a molecule like MEF2, or a fragment thereof, thereby creating an inhibitor of MEF2. This could be accomplished by x-ray crystallography, computer modeling or by a combination of both approaches.

It also is possible to use antibodies to ascertain the structure of a target compound or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds or may be found as active combinations of known compounds which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be polypeptide, polynucleotide, small molecule inhibitors or any other compounds that may be designed through rational drug design starting from known inhibitors of hypertrophic response.

"Effective amounts" in certain circumstances are those amounts effective to reproducibly decrease hypertrophy from the cell in comparison to their normal levels. Compounds that achieve significant appropriate changes in activity will be used.

It will, of course, be understood that all the screening methods of the present invention are useful in themselves notwithstanding the fact that effective candidates may not be found. The invention provides methods for screening for such candidates, not solely methods of finding them.

4. Production of Modulators/Inhibitors

In an extension of any of the previously described screening assays, the present invention also provide for method of producing modulators or inhibitors. The methods comprising any of the preceding screening steps followed by an additional step of "producing the candidate substance identified as a modulator of" the screened activity.

D. Pharmaceutical Compositions

In particular embodiments, where clinical application of an active ingredient (drugs, polypeptides, antibodies or liposomes containing oligo- or polynucleotides or expression vectors) is undertaken, it will be necessary to prepare a pharmaceutical composition appropriate for the intended application. Generally, this will entail preparing a pharmaceutical composition that is essentially free of pyrogens, as well as any other impurities that could be harmful to humans or animals. One also will generally desire to employ appropriate buffers to render the complex stable and allow for uptake by target cells.

Aqueous compositions of the present invention comprise an effective amount of the active ingredient, as discussed above, further dispersed in pharmaceutically acceptable carrier or aqueous medium. Such compositions also are referred to as inocula. The phrases "pharmaceutically or pharmacologically acceptable" refer to compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, a controlled release patch, salve or spray.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Alternatively, administration will be by orthotopic, intradermal subcutaneous, intramuscular, intraperitoneal or intravenous injection. Such compositions would normally be administered as pharmaceutically acceptable compositions that include physiologically acceptable carriers, buffers or other excipients. A preferred embodiment delivery route, for the treatment of a disseminated disease state is systemic, however, regional delivery is also contemplated.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration, the intended goal of treatment and the potency, stability and toxicity of the particular therapeutic substance.

E. Methods of Making Transgenic Animals and Cells

Particular embodiments of the present invention provide transgenic animals and cells lacking one or more functional HDAC 4 or 5 alleles. The inventors have created a MEF2 site dependent lacZ transgene and generated a line of transgenic mice. For example, to test whether the MEF2-lacZ transgene is responsive to hypertrophic signals in the heart, the inventors introduced the transgene by breeding into strains of mice bearing MHC-calcineurin and MHC-CAMKIV transgenes. It was observed in these studies, that lacZ expression was dramatically upregulated in response to calcineurin and CAMKIV, thus mirroring activation of the hypertrophic response. Similar studies with HDAC 4 and 5 mice are contemplated in the present invention. Transgenic animals expressing HDAC 4, HDAC 5, genetic knockout mice, recombinant cell lines and transgenic embryos derived or used to produce such animals, may be useful in methods for screening for and identifying agents that repress or enhance the function of MEF2 and thereby alleviate hypertrophic growth.

In a general aspect, a transgenic animal is produced by the integration of a given construct into the genome. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

Typically, a gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particular embodiment, transgenic mice are generated which express a mutant form of the HDAC 4 or 5 polypeptide which are truncated. Other embodiments include "knock out" HDAC 4 or 5; optionally with a selectable marker replacing all or part of the HDAC 4 or 5 sequence.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 3 µg/ml in 5 mM Tris, pH 7.4 and 0.1 mM EDTA.

Other methods for purification of DNA for microinjection are described in Hogan et al. *Manipulating the Mouse Embryo* (Cold Spring Harbor Laboratory, Cold Spring Harbor, N.Y., 1986), in Palmiter et al. Nature 300:611 (1982); in *The Qiagenologist, Application Protocols*, 3rd edition, published by Qiagen, Inc., Chatsworth, Calif.; and in Sambrook et al. *Molecular Cloning: A Laboratory Manual* (Cold Spring Harbor Laboratory, Cold Spring Harbor, N.Y., 1989).

In an exemplary microinjection procedure, female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG injection, the mated females are sacrificed by $CO_2$ asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection. Embryos can be implanted at the two-cell stage.

Randomly cycling adult female mice are paired with vasectomized males. C57BL/6 or Swiss mice or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures.

As noted above, transgenic animals and cell lines derived from such animals may find use in certain testing experiments. In this regard, transgenic animals and cell lines capable of expressing the mutant HDAC 4 or 5 may be exposed to test substances. These test substances can be screened for the ability to decrease HDAC 4 or 5 expression and/or function. Compounds identified by such procedures will be useful in the treatment of neurological disorders such as narcolepsy. Additionally, test substances can be screened for the ability to increase HDAC 4 or 5 expression and/or function. Compounds identified by such procedures will be useful in the treatment disorders related to lack of sleep, such as insomnia.

In certain embodiments, heterozygotic mice may be used. However, homozygotic mice may be more useful in the methods of the invention. Initial transgenic mice may be heterozygotic for a specific transgene. However, standard breeding techniques known to those of skill in the art may be used to produce homozygotic mice. Genotyping using methods described herein may be used to determine whether a particular animal is heterozygotic or homozygotic one or more transgenes.

1. Transgenic Mice and Their Use

The transgenic animals of the present invention include those which lack one or more HDAC 4 or 5 alleles and have a substantially increased probability of developing cardiac hypertrophy, when compared with non-transgenic littermates. A "substantially increased" probability of developing cardiac hypertrophy means that a statistically significant increase of measurable symptoms of cardiac hypertrophy is observed when comparing the transgenic animal with normal non-transgenic littermates.

Coding regions for use in constructing the transgenic mice include coding segments for the HDAC 4 or 5. The coding regions may encode a complete peptide or polypeptide, or a fragment thereof, as long as the desired function of the peptide or polypeptide is retained, i.e., the polypeptide can contribute to the modulation of the repression of MEF2 activity. The coding regions for use in constructing the transgenes of the present invention further include those containing mutations, including deletions, substitutions, truncations, mutations resulting in a more active protein, mutations that result in a constitutively active protein, and mutations resulting in a protein with reduced activity. Inasmuch as HDAC 4 or 5 mediate the hypertrophy in an animal as identified herein the following discussion is based on an HDAC 4 or 5 knockout transgenic mouse, however, it is understood that the teachings provided herein are equally applicable to other transgenes that also may affect cardiac hypertrophy upstream or downstream of the effect of HDAC 4 or 5.

Another use of the HDAC 4 or 5 transgenic mouse described herein provides a new disease model for cardiac hypertrophy. A HDAC 4 or 5 transgenic mouse provides a novel model for the study of cardiac hypertrophy. This model could help clinicians understand the disease state more fully.

2. Pathological Studies

The various F0, F1 and F2 animals that carry a transgene can be analyzed by any of a variety of techniques, including immunohistology, electron microscopy, electrocardiography and making determinations of total and regional heart weights, measuring cardiomyocyte cross-sectional areas and determining numbers of cardiomyocytes. Immunohistological analysis for the expression of a transgene by using an antibody of appropriate specificity can be performed using known methods. Morphometric analyses to determine regional weights, cardiomyocyte cross-sectional areas and numbers of cardiomyocyte nuclei can be performed using known methods. Hearts can be analyzed for function, histology and expression of fetal cardiac genes.

In immuno-based analyses, it may be necessary to rely on indicator binding antibodies. A general review of antibody production techniques is provided. As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

The immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and tittering is repeated until a suitable titer is achieved. When a desired level of immunogenicity is obtained, the immunized animal can be bled and the serum isolated and stored, and/or the animal can be used to generate mAbs.

A polyclonal antibody is prepared by immunizing an animal with an immunogen comprising a MEF2 or a HDAC 4 or HDAC 5 polypeptide, or fragment thereof, and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit may be a preferred choice for production of polyclonal antibodies.

To obtain monoclonal antibodies, one also would immunize an experimental animal, an antigenic composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to the desired target peptide.

It is proposed that the monoclonal antibodies of the present invention also will find useful application in standard immunochemical procedures, such as ELISA and Western blot methods, as well as other procedures which may utilize antibody specific to MEF2 or HDAC epitopes. Additionally, it is proposed that monoclonal antibodies specific to MEF2 HDAC may be utilized in other useful applications. For example, an anti-idiotype antibody to an anti-HDAC 4 or 5 antibody may well mimic an HDAC 4 or 5 binding site, thus providing a tool for the identification of HDAC 4 or 5 targets.

3. Analysis of Transgene Expression by Measuring mRNA Levels

Messenger RNA can be isolated by any method known in the art, including, but not limited to, the acid guanidinium thiocyanate-phenol:chloroform extraction method (Chomczynski and Sacchi 1987), from cell lines and tissues of transgenic animals to determine expression levels by Northern blots, RNAse and nuclease protection assays.

4. Analysis of Transgene Expression by Measuring Protein Levels

Protein levels can be measured by any means known in the art, including, but not limited to, western blot analysis, ELISA and radioimmunoassay, using one or more antibodies specific for the protein encoded by the transgene.

For Western blot analysis, protein fractions can be isolated from tissue homogenates and cell lysates and subjected to Western blot analysis as described by, for example, Harlow et al., *Antibodies: A Laboratory Manual*, (Cold Spring Harbor, N.Y., 1988); Brown et al., (1983); and Tate-Ostroff et al. (1989).

For example, the protein fractions can be denatured in Laemmli sample buffer and electrophoresed on SDS-Polyacrylamide gels. The proteins are then transferred to nitrocellulose filters by electroblotting. The filters are blocked, incubated with primary antibodies, and finally reacted with enzyme conjugated secondary antibodies. Subsequent incubation with the appropriate chromogenic substrate reveals the position of the transgene-encoded proteins.

ELISAs are preferably used in conjunction with the invention. For example, an ELISA assay may be performed where target protein from a sample is immobilized onto a selected surface, preferably a surface exhibiting a protein affinity such as the wells of a polystyrene microtiter plate. The plate is washed to remove incompletely adsorbed material and the plate is coated with a non-specific protein that is known to be antigenically neutral with regard to the test antibody, such as bovine serum albumin (BSA), casein or solutions of powdered milk. This allows for blocking of nonspecific adsorption sites on the immobilizing surface and thus reduces the background caused by nonspecific binding of antisera onto the surface.

Next, the antibody is added to the plate in a manner conducive to immune complex (antigen/antibody) formation. Such conditions preferably include diluting the antisera/antibody with diluents such as BSA, bovine gamma globulin (BGG) and phosphate buffered saline (PBS)/Tween®. These added agents also tend to assist in the reduction of nonspecific background. The plate is then allowed to incubate for from about 2 to about 4 hr, at temperatures preferably on the order of about 25° to about 27° C. Following incubation, the plate is washed so as to remove non-immunocomplexed material. A preferred washing procedure includes washing with a solution such as PBS/Tween®, or borate buffer.

Following formation of specific immunocomplexes between the sample and antibody, and subsequent washing, the occurrence and amount of immunocomplex formation may be determined by subjecting the plate to a second antibody probe, the second antibody having specificity for the first (usually the Fc portion of the first is the target). To provide a detecting means, the second antibody will preferably have an associated enzyme that will generate a color development upon incubating with an appropriate chromogenic substrate. Thus, for example, one will desire to contact and incubate the antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g. using a visible spectrum spectrophotometer. Variations on this assay, as well as completely different assays (radioimmunprecipitation, immunoaffinity chromatograph, Western blot) also are contemplated as part of the present invention.

A variant of ELISA is the enzyme-linked coagulation assay, or ELCA (U.S. Pat. No. 4,668,621), which uses the coagulation cascade combined with the labeling enzyme RVV-XA as a universal detection system. The advantage of this system for the current invention, is that the coagulation reactions can be performed at physiological pH in the presence of a wide variety of buffers. It is therefore possible to retain the integrity of complex analyses.

Other immunoassays encompassed by the present invention include, but are not limited to those described in U.S. Pat. No. 4,367,110 (double monoclonal antibody sandwich assay) and U.S. Pat. No. 4,452,901 (Western blot). Other assays include immunoprecipitation of labeled ligands and immunocytochemistry, both in vitro and in vivo.

F. Genetic Constructs and Gene Transfer

In particular aspects of the present invention, it is desirable to transfer a HDAC 4 or 5 expression cassette encoding HDAC 4 or HDAC 5 into an organism, tissue or cell. Expression constructs also are used in generating transgenic animals.

1. Genetic Constructs

Throughout this application, the term "expression cassette" is meant to include any type of genetic construct containing a nucleic acid coding for gene products in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding genes of interest.

a. General Promoters

The nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

In certain embodiments, when regulating the expression of genes involved in hypertrophic pathways, it may prove useful to use muscle specific promoters (e.g., human desmin gene promoter, the muscle-specific promoter of the aldolase A gene (pM), smooth muscle α-actin (SMalphaA) promoter, phosphoglycerate mutase gene (M-PGAM), α-myosin heavy chain promoter). Cardiac specific promoters include the myosin light chain-2 promoter (Franz et al., 1994; Kelly et al., 1995), the α actin promoter (Moss et al., 1996), the troponin 1 promoter (Bhavsar et al., 1996); the $Na^+/Ca^{2+}$ exchanger promoter (Barnes et al., 1997), the dystrophin promoter (Kimura et al., 1997), the creatine kinase promoter (Ritchie, M. E., 1996), the alpha7 integrin promoter (Ziober & Kramer, 1996), the brain natriuretic peptide promoter (LaPointe et al., 1996), the alpha B-crystallin/small heat shock protein promoter (Gopal-Srivastava, R., 1995), and alpha myosin heavy chain promoter (Yamauchi-Takihara et al., 1989) and the ANF promoter (LaPointe et al., 1988).

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it may be desirable to prohibit or reduce expression of one or more of the transgenes. Examples of transgenes that may be toxic to the producer cell line are pro-apoptotic and cytokine genes. Several inducible promoter systems are available for production of viral vectors where the transgene product may be toxic.

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of Drosophila, and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter which drives expression of the gene of interest is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristerone A.

Another inducible system that would be useful is the Tet-Off™ or Tet-On™ system (Clontech, Palo Alto, Calif.) originally developed by Gossen and Bujard (Gossen and Bujard, 1992; Gossen et al., 1995). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of *E. coli*. The tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled trans-activator, which is composed, in the Tet-Off™ system, of the VP16 domain from the herpes simplex virus and the wild-type tertracycline repressor. Thus in the absence of doxycycline, transcription is constitutively on. In the Tet-On™ system, the tetracycline repressor is not wild type and in the presence of doxycycline activates transcription. For gene transfer vector production, the Tet-Off™ system would be preferable so that the producer cells could be grown in the presence of tetracycline or doxycycline and prevent expression of a potentially toxic transgene, but when the vector is introduced to the patient, the gene expression would be constituitively on.

In some circumstances, it may be desirable to regulate expression of a transgene in a gene transfer vector. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoetic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Similarly tissue specific promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2)

may be used to target gene expression in the prostate. Similarly, the following promoters may be used to target gene expression in other tissues.

It is envisioned that any of the above promoters alone or in combination with another may be useful according to the present invention depending on the action desired. In addition, this list of promoters is should not be construed to be exhaustive or limiting, those of skill in the art will know of other promoters that may be used in conjunction with the promoters and methods disclosed herein.

b. Enhancers

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

In preferred embodiments of the invention, the expression construct comprises a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

C. Polyadenylation Signals

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human or bovine growth hormone and SV40 polyadenylation signals. Also contemplated as an element of the expression cassette is a terminator. These elements can serve to enhance message levels and to minimize read through from the cassette into other sequences.

2. Gene Transfer

Gene transfer is important both in the therapeutic context and in the generation of transgenic cells and animals. There are a number of ways in which expression vectors may introduced into cells. In certain embodiments of the invention, the expression construct comprises a virus or engineered construct derived from a viral genome. In other embodiments, non-viral delivery is contemplated. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). Delivery mechanisms are discussed in further detail herein below.

a. Non-Viral Transfer

The present section provides a discussion of methods and compositions of non-viral gene transfer. DNA constructs of the present invention are generally delivered to a cell, and in certain situations, the nucleic acid or the protein to be transferred may be transferred using non-viral methods.

Several non-viral methods for the transfer of expression constructs into cultured mammalian cells are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al, 1979), cell sonication (Fechheimer et al., 1987), gene bombardment using high velocity microprojectiles (Yang et al., 1990), and receptor-mediated transfection (Wu and Wu, 1987; Wu and Wu, 1988).

Once the construct has been delivered into the cell the nucleic acid encoding the particular gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In another particular embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). The addition of DNA to cationic liposomes causes a topological transition from liposomes to optically birefringent liquid-crystalline condensed globules (Radler et al., 1997). These DNA-lipid complexes are potential non-viral vectors for use in gene delivery.

Liposome-mediated nucleic acid delivery and expression of foreign DNA in vitro has been very successful. Using the β-lactamase gene, Wong et al. (1980) demonstrated the feasibility of liposome-mediated delivery and expression of foreign DNA in cultured chick embryo, HeLa, and hepatoma cells. Nicolau et al. (1987) accomplished successful liposome-mediated gene transfer in rats after intravenous injection. Also included are various commercial approaches involving "lipofection" technology.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear nonhistone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0 273 085).

In other embodiments, the delivery vehicle may comprise a ligand and a liposome. For example, Nicolau et al (1987) employed lactosyl-ceramide, a galactose-terminal asialganglioside, incorporated into liposomes and observed an increase in the uptake of the insulin gene by hepatocytes.

In another embodiment of the invention, the expression construct may simply consist of naked recombinant DNA or plasmids. Transfer of the construct may be performed by any of the methods mentioned above which physically or chemically permeabilize the cell membrane. This is applicable particularly for transfer in vitro, however, it may be applied for in vivo use as well. Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a CAM may also be transferred in a similar manner in vivo and express CAM.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

In certain embodiments, gene transfer may more easily be performed under ex vivo conditions. Ex vivo gene application refers to the isolation of cells from an animal, the delivery of a nucleic acid into the cells in vitro, and then the return of the modified cells back into an animal. This may involve the surgical removal of tissue/organs from an animal or the primary culture of cells and tissues.

b. Viral Transfer

Adenovirus. One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide, a protein, a polynucleotide (e.g., ribozyme, or an mRNA) that has been cloned therein. In this context, expression does not require that the gene product be synthesized.

The expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retroviruses, the adenoviral infection of host cells does not result in chromosomal integration because adenoviral DNA can replicate in an episomal manner without potential genotoxicity. As used herein, the term "genotoxicity" refers to permanent inheritable host cell genetic alteration. Also, adenoviruses are structurally stable, and no genome rearrangement has been detected after extensive amplification of normal derivatives. Adenovirus can infect virtually all epithelial cells regardless of their cell cycle stage. So far, adenoviral infection appears to be linked only to mild disease such as acute respiratory disease in non-immunosuppressed humans.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

The E3 region encodes proteins that appears to be necessary for efficient lysis of Ad infected cells as well as preventing TNF-mediated cytolysis and CTL mediated lysis of infected cells. In general, the E4 region encodes is believed to encode seven proteins, some of which activate the E2 promoter. It has been shown to block host mRNA transport and enhance transport of viral RNA to cytoplasm. Further the E4 product is in part responsible for the decrease in early gene expression seen late in infection. E4 also inhibits E1A and E4 (but not E1B) expression during lytic growth. Some E4 proteins are necessary for efficient DNA replication however the mechanism for this involvement is unknown. E4 is also involved in post-transcriptional events in viral late gene expression; i.e., alternative splicing of the tripartite leader in lytic growth. Nevertheless, E4 functions are not absolutely required for DNA replication but their lack will delay replication. Other functions include negative regulation of viral DNA synthesis, induction of sub-nuclear reorganization normally seen during adenovirus infection, and other functions that are necessary for viral replication, late viral mRNA accumulation, and host cell transcriptional shut off.

In a current system, recombinant adenovirus is generated from homologous recombination between shuttle vector and provirus vector. Possible recombination between the proviral vector and Ad sequences in 293 cells, or in the case of pJM17 plasmid spontaneous deletion of the inserted pBR322 sequences, may generate full length wild-type Ad5 adenovirus. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the E3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993; Shenk, 1978).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking is initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical, medical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986), or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$-$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression investigations (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene transfer (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993), intranasal inoculation (Ginsberg et al., 1991), aerosol administration to lung (Bellon, 1996) intraperitoneal administration (Song et al., 1997), Intrapleural injection (Elshami et al., 1996) administration to the bladder using intravesicular administration (Werthman, et al., 1996), Subcutaneous injection including intraperitoneal, intrapleural, intramuscular or subcutaneously) (Ogawa, 1989) ventricular injection into myocardium (heart, French et al., 1994), liver perfusion (hepatic artery or portal vein, Shiraishi et al., 1997) and stereotactic inoculation into the brain (Le Gal La Salle et al., 1993).

Retrovirus. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via asialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Herpesvirus. Because herpes simplex virus (HSV) is neurotropic, it has generated considerable interest in treating nervous system disorders. Moreover, the ability of HSV to establish latent infections in non-dividing neuronal cells without integrating in to the host cell chromosome or otherwise altering the host cell's metabolism, along with the existence of a promoter that is active during latency makes HSV an attractive vector. And though much attention has focused on the neurotropic applications of HSV, this vector also can be exploited for other tissues given its wide host range.

Another factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations.

HSV also is relatively easy to manipulate and can be grown to high titers. Thus, delivery is less of a problem, both in terms of volumes needed to attain sufficient MOI and in a lessened need for repeat dosings. For a review of HSV as a gene transfer vector, see Glorioso et al. (1995).

HSV, designated with subtypes 1 and 2, are enveloped viruses that are among the most common infectious agents encountered by humans, infecting millions of human subjects worldwide. The large, complex, double-stranded DNA genome encodes for dozens of different gene products, some of which derive from spliced transcripts. In addition to virion and envelope structural components, the virus encodes numerous other proteins including a protease, a ribonucleotides reductase, a DNA polymerase, a ssDNA binding protein, a helicase/primase, a DNA dependent ATPase, a dUTPase and others.

HSV genes form several groups whose expression is coordinately regulated and sequentially ordered in a cascade fashion (Honess and Roizman, 1974; Honess and Roizman 1975; Roizman and Sears, 1995). The expression of α genes, the first set of genes to be expressed after infection, is enhanced by the virion protein number 16, or α-transducing factor (Post et al., 1981; Batterson and Roizman, 1983). The expression of β genes requires functional a gene products, most notably ICP4, which is encoded by the α4 gene (DeLuca et al., 1985). γ genes, a heterogeneous group of genes encoding largely virion structural proteins, require the onset of viral DNA synthesis for optimal expression (Holland et al., 1980).

In line with the complexity of the genome, the life cycle of HSV is quite involved. In addition to the lytic cycle, which results in synthesis of virus particles and, eventually, cell death, the virus has the capability to enter a latent state in which the genome is maintained in neural ganglia until some as of yet undefined signal triggers a recurrence of the lytic cycle. A virulent variants of HSV have been developed and are readily available for use in gene transfer contexts (U.S. Pat. No. 5,672,344).

Adeno-Associated Virus. Recently, adeno-associated virus (AAV) has emerged as a potential alternative to the more commonly used retroviral and adenoviral vectors. While studies with retroviral and adenoviral mediated gene transfer raise concerns over potential oncogenic properties of the former, and immunogenic problems associated with the latter, AAV has not been associated with any such pathological indications.

In addition, AAV possesses several unique features that make it more desirable than the other vectors. Unlike retroviruses, AAV can infect non-dividing cells; wild-type AAV has been characterized by integration, in a site-specific manner, into chromosome 19 of human cells (Kotin and Berns, 1989; Kotin et al., 1990; Kotin et al., 1991; Samulski et al., 1991); and AAV also possesses anti-oncogenic properties (Ostrove et al., 1981; Berns and Giraud, 1996). Recombinant AAV genomes are constructed by molecularly cloning DNA sequences of interest between the AAV ITRs, eliminating the entire coding sequences of the wild-type AAV genome. The AAV vectors thus produced lack any of the coding sequences of wild-type AAV, yet retain the property of stable chromosomal integration and expression of the recombinant genes upon transduction both in vitro and in vivo (Berns, 1990; Berns and Bohensky, 1987; Bertran et al., 1996; Kearns et al., 1996; Ponnazhagan et al, 1997a). Until recently, AAV was believed to infect almost all cell types, and even cross species barriers. However, it now has been determined that AAV infection is receptor-mediated (Ponnazhagan et al., 1996; Mizukami et al., 1996).

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription. The sequence of AAV is provided by Srivastava et al (1983), and in U.S. Pat. No. 5,252,479 (entire text of which is specifically incorporated herein by reference).

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42-46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

Vaccinia Virus. Vaccinia virus vectors have been used extensively because of the ease of their construction, relatively high levels of expression obtained, wide host range and large capacity for carrying DNA. Vaccinia contains a linear, double-stranded DNA genome of about 186 kb that exhibits a marked "A-T" preference. Inverted terminal repeats of about 10.5 kb flank the genome. The majority of essential genes appear to map within the central region, which is most highly conserved among poxviruses. Estimated open reading frames in vaccinia virus number from 150 to 200. Although both strands are coding, extensive overlap of reading frames is not common.

At least 25 kb can be inserted into the vaccinia virus genome (Smith and Moss, 1983). Prototypical vaccinia vectors contain transgenes inserted into the viral thymidine kinase gene via homologous recombination. Vectors are selected on the basis of a tk-phenotype. Inclusion of the untranslated leader sequence of encephalomyocarditis virus, the level of expression is higher than that of conventional vectors, with the transgenes accumulating at 10% or more of the infected cell's protein in 24 h (Elroy-Stein et al., 1989).

C. Selection Methods

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

Thus, following introduction of the expression construct into the cells, expression of the reporter gene can be determined by conventional means. Any assay which detects a product of the reporter gene, either by directly detecting the protein encoded by the reporter gene or by detecting an enzymatic product of a reporter gene-encoded enzyme, is suitable for use in the present invention. Assays include colorimetric, fluorimetric, or luminescent assays or even, in the case of protein tags, radioimmunoassays or other immunological assays. Transfection efficiency can be monitored by co-transfecting an expression construct comprising a constitutively active promoter operably linked to a reporter gene.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

G. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Preparation of primary rat cardiomyocytes. Cardiomyocyte cultures are prepared by dissociation of 1-day old neonatal rat hearts and were differentially plated to remove fibroblasts. To induce the hypertrophic response, AngII and PE are added to cardiomyocyte cultures at 10 nM and 10 µM, respectively, in serum-free M199 media. The culture media containing either agonist is changed every 12 hours for a period of 72 hours.

Immunocytochemistry. To visualize sarcomeric organization in primary cardiomyocytes, anti-α-actinin mouse monoclonal antibody is used (Sigma). Cells are washed in 1×PBS, fixed in 3.7% paraformaldehyde for 5 minutes, washed three times with 1×PBS and then pre-blocked in 1×PBS containing 2% horse serum, 2% BSA, and 0.1% NP40 for 30 minutes. Anti-α-actinin antibody is added at a dilution of 1:800 in fresh pre-block solution and incubated for an additional 30 minutes. Subsequently, cells are washed three times in 1×PBS with 0.1% NP40. Anti-mouse TRITC-conjugated secondary antibody is then added at a dilution of 1:400 for 30 minutes in pre-block solution and the cells are again washed three times in 1×PBS containing 0.1% NP40. Nuclear staining for DNA is performed with 0.5 µg/ml of bis-benzimide in PBS for 15 min followed by three rinses with PBS.

RNA analysis. Total RNA was collected and purified with Triazol reagent (Gibco BRL) as recommended. RNA from wild-type and transgenic hearts, as well as from cultured cardiomyocytes, was subjected to dot blot hybridization against a panel of oligonucleotide probes as described previously (Jones et al., 1996).

Histology. Hearts from wild-type and transgenic mice were subjected to histological analysis. Briefly, hearts were collected, fixed overnight in 10% formalin buffered with PBS, dehydrated in ethanol, transferred to xlyene then into paraffin. Paraffin-embedded hearts were sectioned at 4 µM and subsequently stained with hematoxylin and eosin for routine histologic examination or with Masson trichrome for collagen (Woods and Ellis, 1994).

Example 2

The Role of MEF2 in Cardiac Gene Expression

Figure 1:
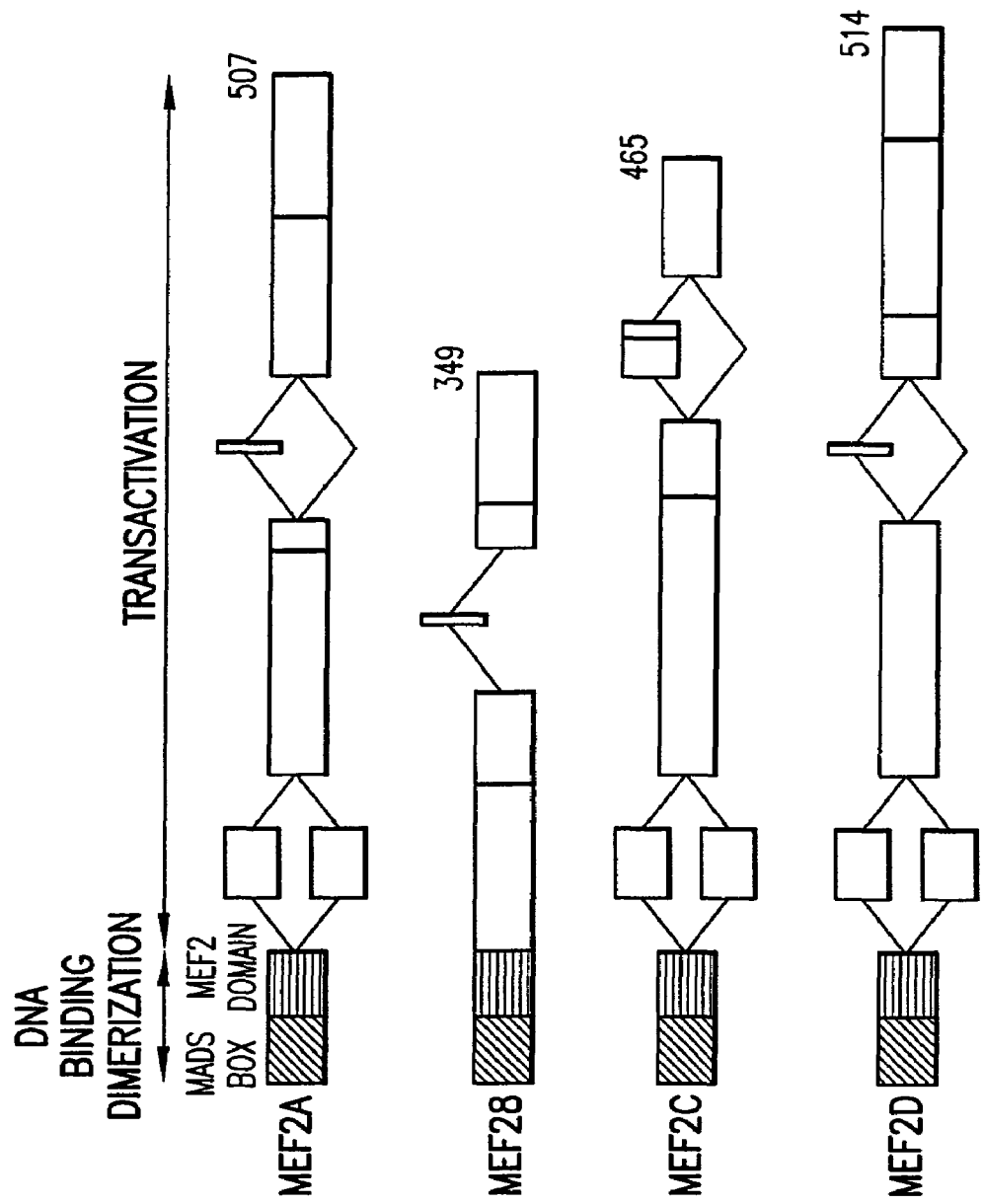
FIG. 1. Schematic diagrams of the MEF2 isoforms.
Figure 2:
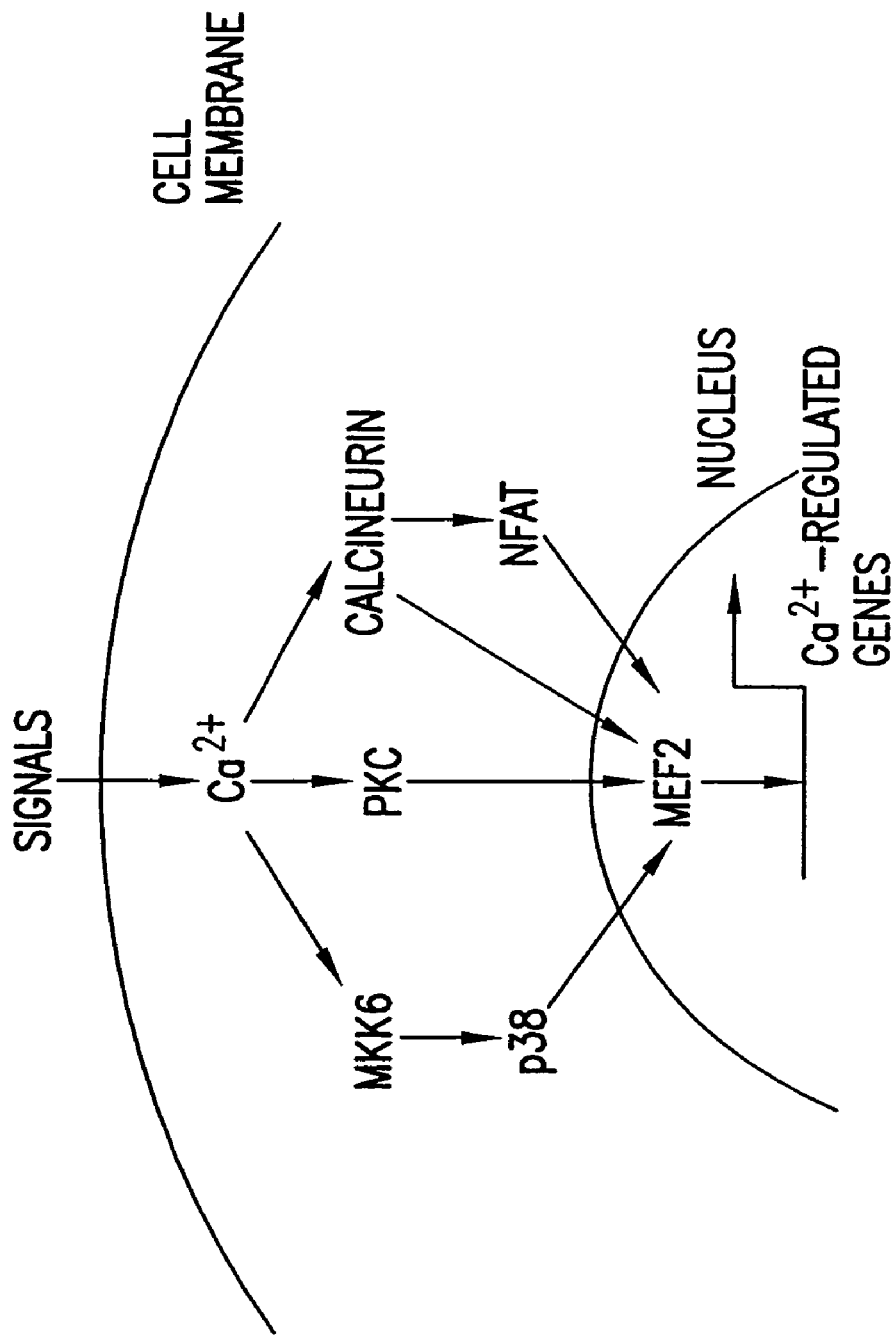
FIG. 2. Calcium-dependent signaling systems that regulate MEF2 activity. A variety of extracellular stimuli result in elevation of intracellular calcium, which activates multiple intracellular signaling systems, including calcineurin, CAM kinases, PKC, and MAP kinases. All of these signals activate MEF2 and result in cardiac hypertrophy.

Structure-function studies. There are four vertebrate MEF2 genes, whose products are schematized in FIG. 1. Through extensive mutational analyses, the functional domains of the MEF2 proteins have been characterized (Molkentin et al., 1995; Martin et al., 1993; Molkentin et al., 1996a; 1996b). These studies demonstrate that the N-terminal MADS-box mediates DNA binding and dimerization. The adjacent MEF2 domain influences DNA binding affinity and interactions with myogenic bHLH proteins, and the C-terminal regions of the MEF2 factors contain multiple independent transcriptional activation domains.

Cooperative activation of muscle transcription by MEF2 and myogenic bHLH factors. In the skeletal muscle lineage, MEF2 acts combinatorially with members of the MyoD family of bHLH transcription factors to activate muscle gene transcription. It has been demonstrated that the MADS-box of the MEF2 proteins interacts directly with the bHLH regions of the myogenic factors (Molkentin et al., 1995). This biochemical model for combinatorial control of muscle gene expression by MEF2 factors is supported by genetic studies in Drosophila, which have shown that MEF2 is an essential cofactor for differentiation of all types of myoblasts, skeletal, cardiac and visceral (Lilly et al., 1995; Bour et al., 1995).

Figure 3:
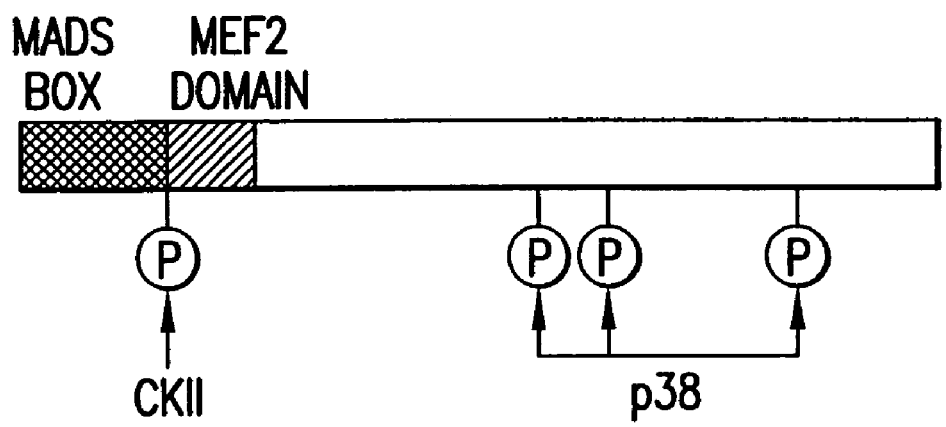
FIG. 3. Locations of known phosphorylation sites in MEF2C.

MEF2 phosphorylation. Phosphopeptide mapping studies demonstrate that MEF2 factors contain multiple phosphorylation sites. It is shown that a casein kinase-II (CKII) site in the MADS-box enhances the affinity of MEF2C for DNA (Molkentin et al. 1996c). This site is conserved in all known MEF2 proteins in organisms ranging from Drosophila and C. elegans to humans, consistent with its importance for MEF2 function. It has not yet been determined whether this site is subject to regulated phosphorylation. A schematic diagram of MEF2C and the phosphorylation sites that have been defined to date are shown in FIG. 3.

Also it is shown that the transcriptional activity of MEF2C is dramatically enhanced in the presence of activated PKC. Transfection of fibroblasts with a MEF2-dependent reporter gene, along with expression vectors for MEF2C and an activated form of PKC, results in a greater than 10-fold increase in transcriptional activity with no apparent increase in DNA binding. These results suggest that may MEF2C mediate certain transcriptional effects of PKC.

MEF2 gene knockouts. By gene targeting, the four MEF2 genes in ES cells and transgenic mice are inactivated. Mice lacking MEF2C die at E9.5 from severe cardiovascular defects that include the absence of a right ventricle and the failure of the vascular system to form (Lin et al., 1997). In addition, a subset of cardiac contractile protein genes, including α-MHC, α-cardiac actin, and ANF, fail to be expressed in the developing heart. In contrast, several other cardiac genes, such as myosin light chains 2A and −2V, are expressed at normal levels in the hearts of MEF2C mutant embryos, indicating that they were MEF2C-independent. Since these genes also contain essential MEF2 binding sites in their promoters, it is likely that another member of the MEF2 family can support their expression in the absence of MEF2C. MEF2B is coexpressed with MEF2C in the early heart and is upregulated in MEF2C mutant embryos, making it a likely candidate for playing a partially overlapping role with MEF2C. The finding that a subset of cardiac genes is dependent on MEF2C indicates that muscle genes can discriminate between different members of the MEF2 family.

Example 3

Induction of MEF2 Activity In Vitro by Hypertrophic Signaling

Figure 4:
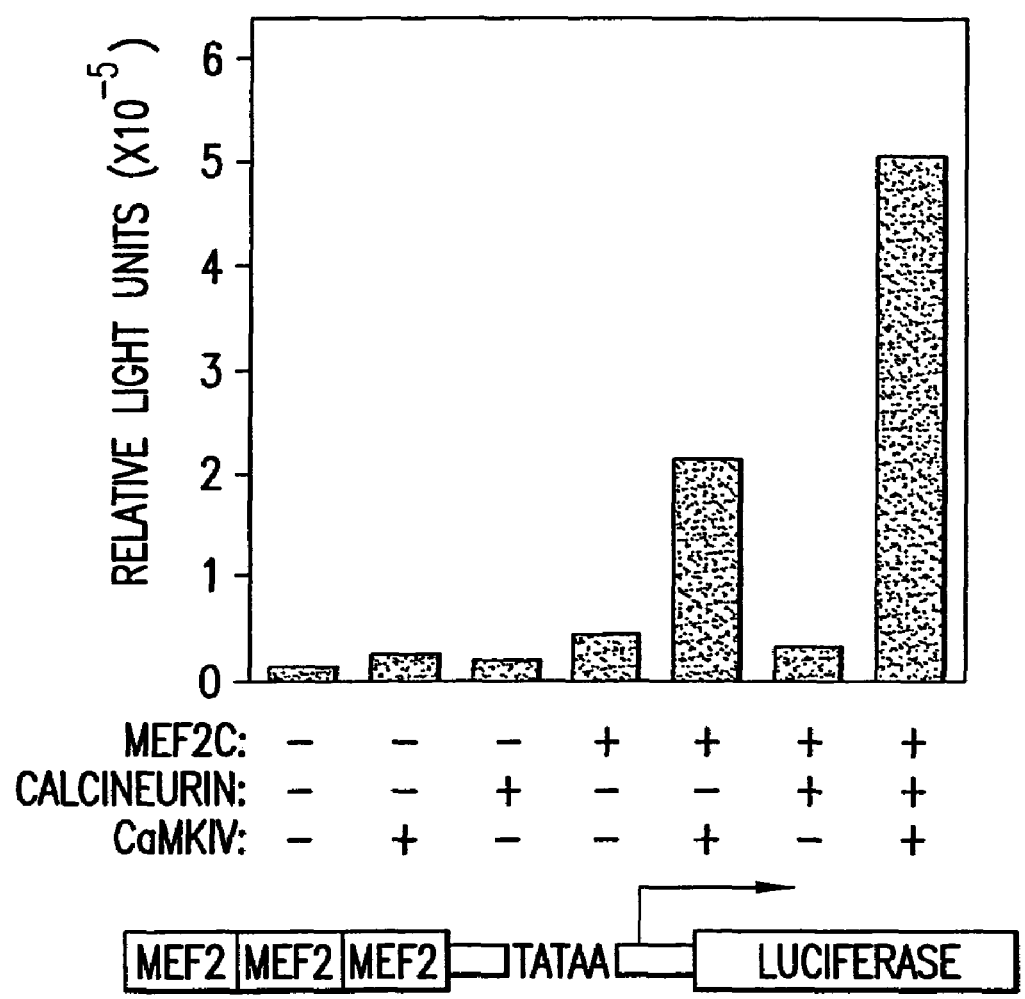
FIG. 4. CaMKIV and calcineurin synergize to activate a MEF2-dependent reporter gene.

In light of the ability of MEF2 to respond to calcium-dependent signal transduction pathways in T cells, the inventors have investigated whether the same pathways also activate MEF2 in cardiomyocytes. As shown in FIG. 4, activated calcineurin or CaMKIV can upregulate a MEF2-dependent luciferase reporter gene in transfected cardiomyocytes and together these calcium-sensitive signaling enzymes synergistically activate MEF2-dependent gene expression. In DNA binding assays, an increase in MEF2 DNA binding activity in response to activated calcineurin and CaMKIV is not observed suggesting that the increase in MEF2 transcriptional activity reflects a post-translational mechanism. When the C-terminus of MEF2C, which contains the transcription activation domains (TADs), but lacks the MADS and MEF2 domains required for DNA binding and dimerization, is fused to the DNA binding domain of the yeast transcription factor GAL4, the resulting GAL4-MEF2C fusion protein retains sensitivity to calcineurin and CaMKIV. This GAL4-MEF2C fusion protein is also activated by stimulation of cardiomyocytes with the hypertrophic agonist phenylephrine (PE). Together, these results demonstrate that the transcription activation domain of MEF2C is a nuclear target for hypertrophic signaling pathways.

Example 4

Creation of MEF2 Indicator Mice

Figure 5:
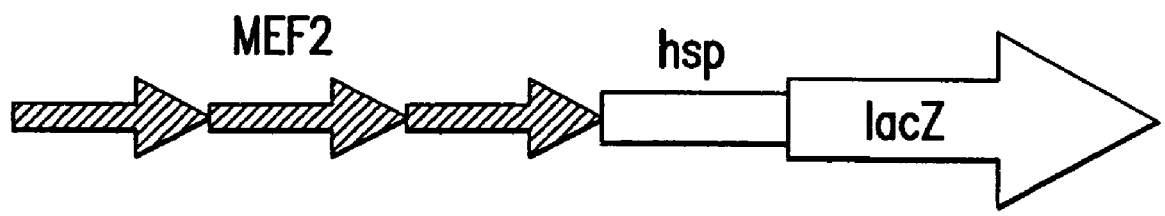
FIG. 5. Diagram of MEF2-dependent lacZ reporter gene. Three tandem copies of the MEF2 binding site from the desmin gene were cloned upstream of a lacZ reporter under control of the hsp68 promoter.

The in vitro assays support the conclusion that MEF2 is an important downstream target for hypertrophic signaling pathways in cardiomyocytes. To extend these observations to an in vivo setting, in which the time course for hypertrophic stimulation is prolonged and the physiology of an intact heart is distinct from cultured cardiomyocytes, a sensitive and specific strain of mice that faithfully reveal MEF2 activation in the heart by activation of a lacZ transgene has been developed. These mice were created using a transgene in which three tandem copies of the MEF2 site from the desmin gene were cloned upstream of the heat shock protein (hsp)-68 promoter, which is expressed at a basal level in all cells, and a lacZ reporter (FIG. 5). The sequence of the MEF2 site used to create this construct is:

(SEQ ID NO:1)
GGCCTTTCCTTCTCCT<u>CTATAAATAC</u>CAGCTCTGGTATTTCA

Figure 6:
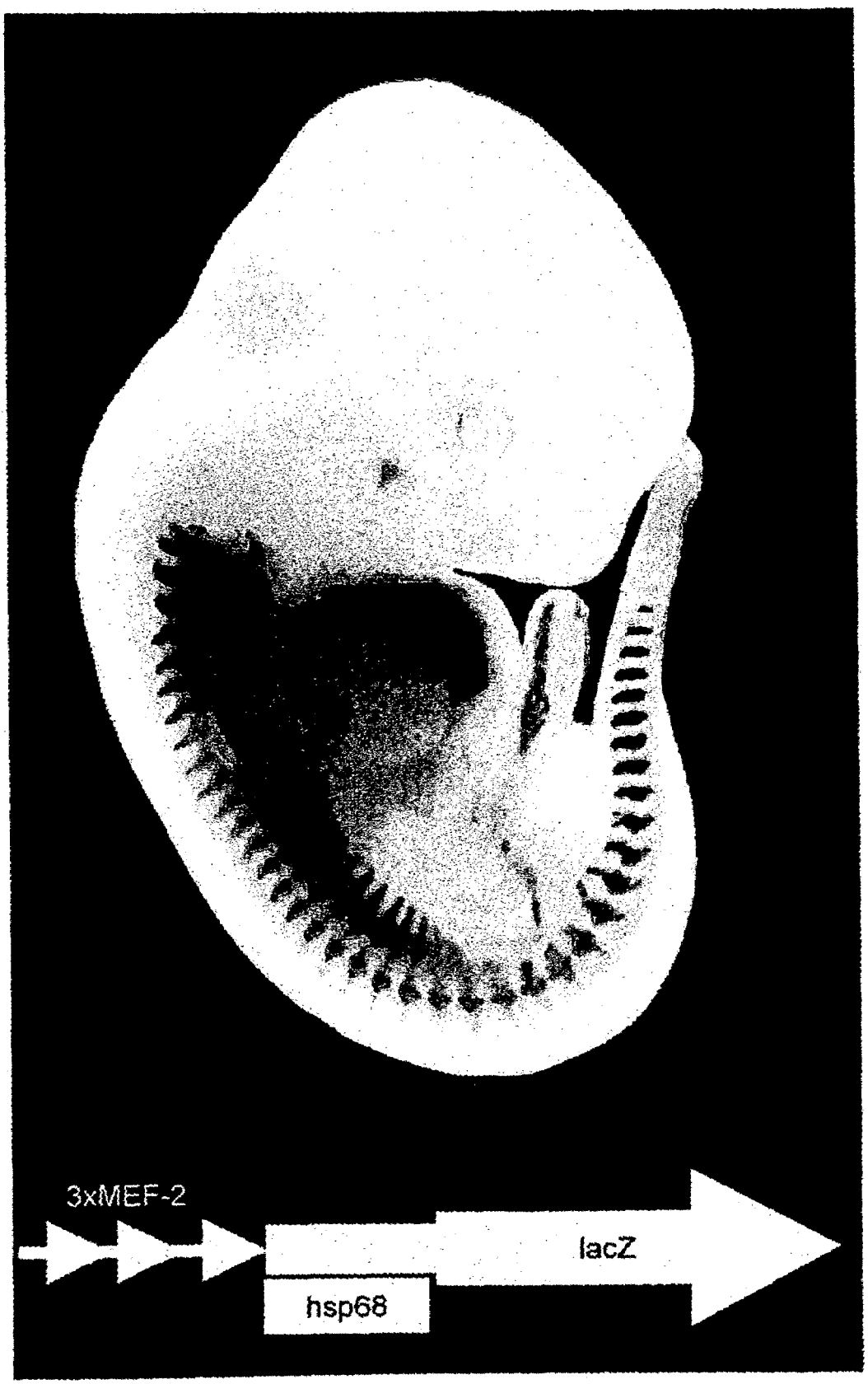
FIG. 6. LacZ staining of a transgenic mouse embryo harboring a MEF2 site-dependent lacZ transgene. The MEF2-lacZ transgene was used to generate a line of transgenic mice. A transgenic mouse embryo at E10.5 stained for lacZ expression is shown.
Figure 11:
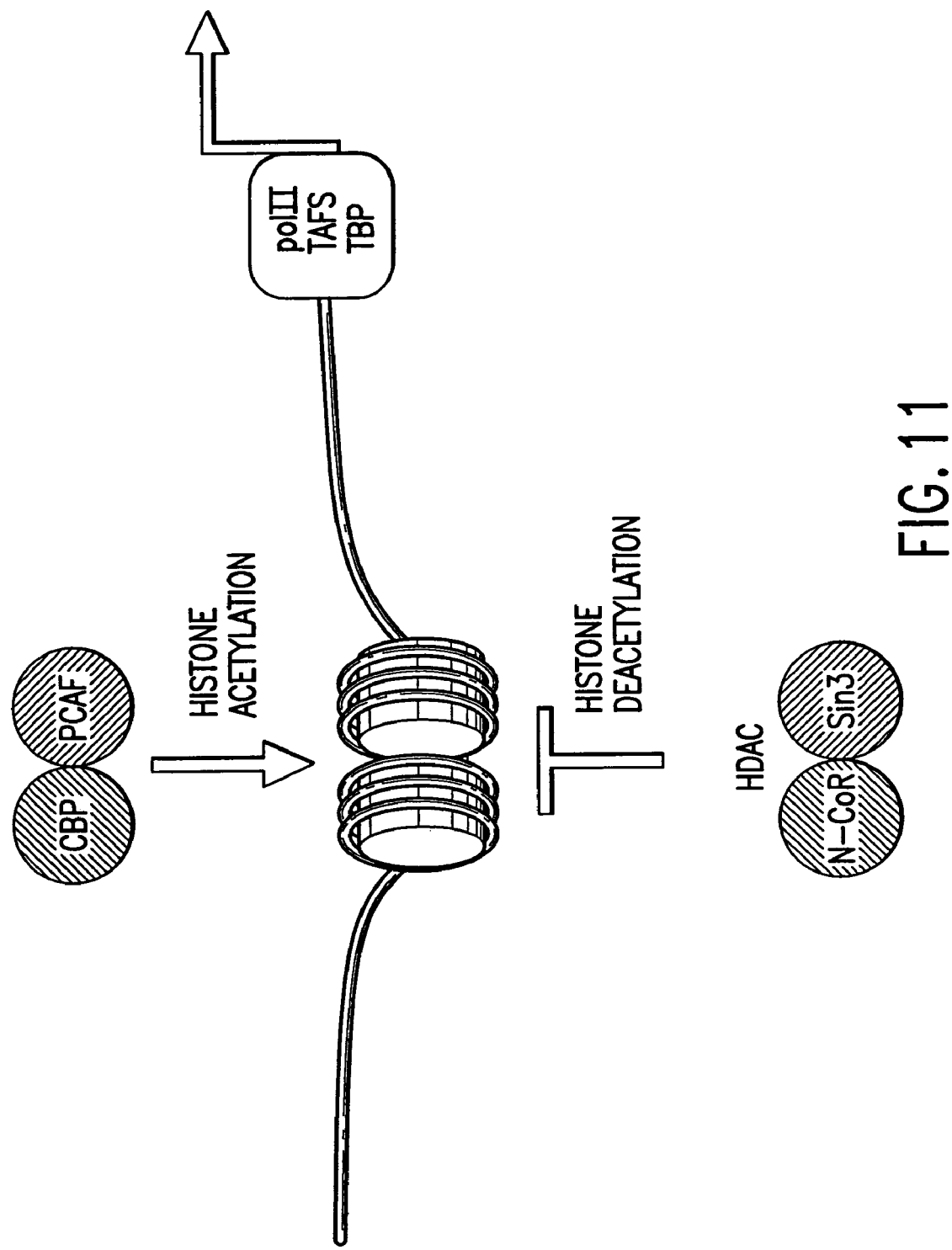
FIG. 11. Schematic diagram of the roles of histone acetylases and deacetylases in the control of gene expression. The balance between activities of histone acetylases (HA) and deacetylases (HDAC) determines the level of histone acetylation. Acetylated histones cause relaxation of chromatin and activation of gene transcription, whereas deacetylated chromatin is generally transcriptionally inactive. Different protein components of HA and HDAC complexes are shown.
Figure 14A:
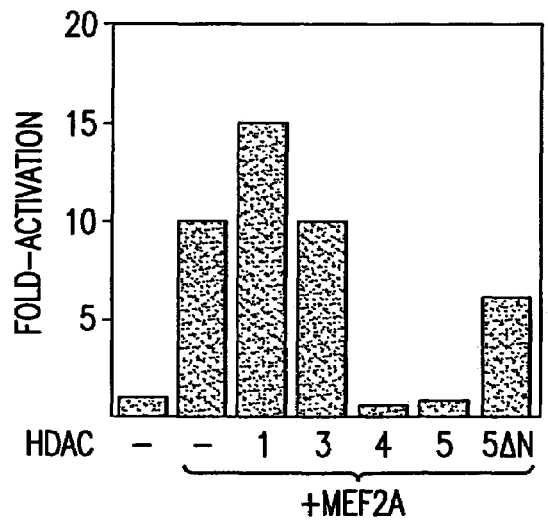
FIG. 14A, FIG. 14B, FIG. 14C and FIG. 14D. Repression of MEF2 activity by HDACs 4 and 5. Cos cells were transiently transfected with the MEF2 reporter plasmid, MEF2× 2-luciferase, along with expression vectors encoding the indicated MEF2 factor, HDAC isoform or HDAC 5 lacking the amino-terminal MEF2 binding domain. HDACs 4 and 5 repress transcriptional activity of MEF2A, MEF2C, and MEF2D. Replacement of the MEF2 transcription activation domain with VP16 reduces the ability of HDAC to repress. HDAC 5 lacking the amino-terminus (HDAC 5ΔN) cannot repress.
Figure 14B:
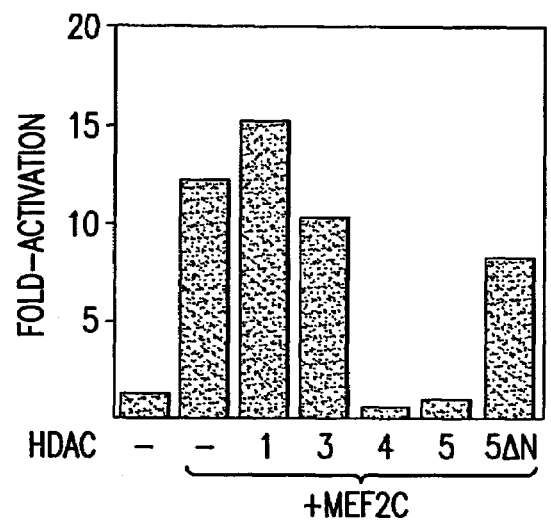
Figure 14C:
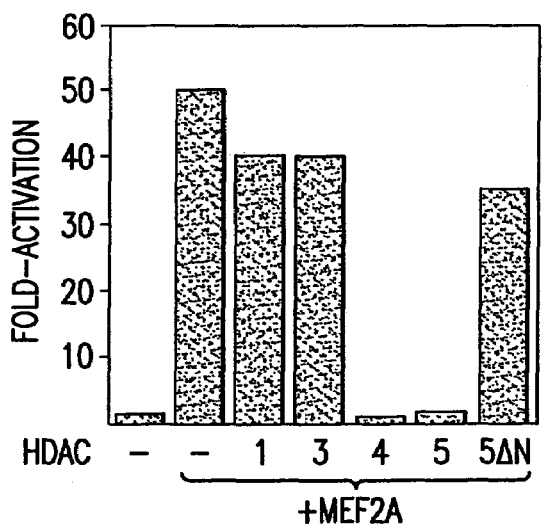
Figure 14D:
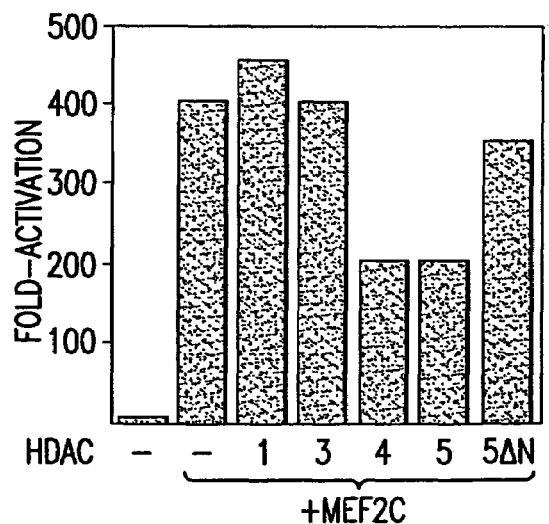

The MEF2 site is underlined in the above sequence. The inventors have characterized the expression pattern of this transgene throughout pre- and postnatal life. During embryogenesis, the MEF2 site-dependent transgene is expressed in developing muscle cell lineages (FIG. 6), consistent with the importance of MEF2 factors for activation of cardiac, skeletal, and smooth muscle gene expression. However, after birth, expression of the transgene is downregulated to levels that are undetectable by colorimetric lacZ staining of tissues.

Example 5

Cardiac Hypertrophy In Vivo in Response to Activated CaMKIV Expression

In light of the ability of CaM kinases I and IV to induce hypertrophic-responsive promoters in primary cardiomyocytes, studies were extended to investigate whether CaM kinase signaling could also induce cardiac hypertrophy in vivo. Transgenic mice were generated with a transgene encoding activated CaMKIV under control of the A-MHC promoter.

Four independent mouse lines bearing the α-MHC-CaMKIV transgene were obtained. Three lines had a single copy of the transgene and one line had 3 copies. Founder transgenic mice were bred to C57BL/6 mice to generate F1 offspring. Transgene expression was determined by Northern analysis using a probe specific to the 3' untranslated region of exogenous CaMKIV. Each of the transgenic lines expressed the CaMKIV transgene in the heart.

Examination of the hearts of these mice beginning at 1 month of age revealed dramatic enlargement. The heart weight-to-body weight ratios of the transgenics were reproducibly 2-fold greater than wild-type at one month of age and the rate of progression of cardiac disease was similar in all four transgenic lines. An additional transgenic mouse with an estimated 50 copies of the transgene died at 3 weeks of age and showed extreme dilated cardiomyopathy. The early lethality in this animal and the fact that viable transgenic lines had only 1 to 3 copies of the transgene may indicate that activated CaMKIV is a highly potent hypertrophic stimulus that can only be tolerated at relatively low levels.

Histological analysis of transgenic hearts showed obvious cardiomyocyte enlargement and disorganization (FIG. 7). By 2 months of age, extensive interstitial fibrosis was observed by Masson-trichrome staining. In contrast to mice that express activated calcineurin in the heart, and develop dilated cardiomyopathy by 8 weeks of age and then become highly prone to sudden death, α-MHC-CaMKIV did not progress to a dilated cardiac phenotype and exhibited a normal lifespan. The extent of hypertrophic growth was also less and the time course delayed in CaMKIV compared to calcineurin transgenic mice.

Example 6

Upregulation of Fetal Cardiac Genes in Hearts of α-MHC-CaMKIV Transgenic Mice

The inventors examined expression of several hypertrophic-responsive cardiac genes in CaMKIV transgenic mice by Northern analysis of RNA from heart. ANF transcripts were upregulated, whereas α-MHC transcripts were downregulated in hypertrophic transgenic hearts, consistent with the changes in gene expression known to occur in hypertrophic hearts. GAPDH transcripts were measured to confirm equivalent RNA loading of samples.

Example 7

Altered Cardiac Function in α-MHC-CaMKIV Transgenic Mice

Using transthoracic echocardiography, cardiac function was characterized in aMHC-CaMKIV transgenic mice. As summarized in Table 1, there was a dramatic and statistically significant increase in left ventricular mass and an accompanying decrease in fractional shortening in transgenic compared to control littermates. These changes are indicative of hypertrophy progressing to heart failure.

TABLE 1

| | Echocardiographic Analysis | |
| --- | --- | --- |
| | LV Mass | Fractional Shortening |
| Nontransgenic | 0.089 +/− 0.005 | 46.80 +/− 1.38 |
| CaMKIV Transgenic | 0.127 +/− 0.01 | 29.38 +/− 4.04 |

$p > 0.005$ for LV mass
$p > 0.001$ for FS

Example 8

CaMKIV Enhances the Transcriptional Activity of MEF2 In Vivo

The inventors have found previously that CaMKIV stimulates transcriptional activity of MEF2 factors in transfected cardiomyocytes. To determine whether activation of CaMKIV in the intact heart in vivo also leads to an increase in transcriptional activity of MEF2, a line of transgenic mice bearing a lacZ reporter gene under control of three tandem copies of a high-affinity MEF2 site was used. The expression of this MEF2-dependent reporter gene mirrors that of transcriptionally active MEF2 proteins throughout embryogenesis, but after birth, expression of the transgene is reduced to low levels, presumably because MEF2 proteins are also less active at this stage (Naya et al., 1999).

In the adult heart, the MEF2-dependent lacZ transgene is expressed at a basal level. However, when the transgene was introduced into the transgenic line bearing the aMHC-CaMKIV transgene, lacZ expression was dramatically upregulated with hypertrophy (FIG. 8). Quantitative b-galactosidase assays showed a greater than 100-fold increase in transcriptional activity of MEF2 in the hypertrophic heart.

To determine whether upregulation of MEF2-lacZ expression was a specific response to CaMKIV signaling or, alternatively, a general response to hypertrophy, the MEF2 indicator mice were bred with a line of mice harboring an aMHC-calcineurin transgene. The degree of hypertrophy in these mice is much more pronounced than in CaMKIV transgenics, with hearts becoming enlarged to about 3 times greater than normal by two months of age. In contrast to the dramatic and homogeneous activation of the lacZ transgene throughout the hearts of CaMKIV transgenic mice, lacZ expression was observed only in scattered clusters of cardiomyocytes in calcineurin transgenic mice. Thus, despite the fact that calcineurin was a much more potent inducer of hypertrophy than CaMKIV, it was a much weaker inducer of the MEF2-lacZ transgene. The inventors conclude that MEF2 responds specifically to CaMKIV signaling in the intact heart.

Example 9

CaMKIV Stimulates Transcriptional Activity of MEF2 without Affecting DNA Binding Activity The increase in expression of the MEF2-dependent lacZ transgene in response to CaMKIV could reflect an increase in MEF2 protein or an increase in transcriptional activity of preexisting MEF2 protein. To distinguish between these possibilities, western blots and gel mobility shift assays were performed with nuclear extracts from hearts of wild-type and CaMKIV transgenic littermates. The level of MEF2 DNA binding activity was comparable in cardiac extracts from wild-type, CaMKIV transgenics, and calcineurin transgenics. These results are consistent with those from primary cardioof MEF2. Thus, MEF2 receives hypertrophic signals through two distinct domains and subsequently activates downstream hypertrophic genes.

EXAMPLE 10

Localization of the MEF2-Interaction Region of HDAC 4 and 5 with the Yeast Two-Hybrid System Using the yeast two-hybrid system, inventors localized the MEF2/HDAC 4 and 5 binding region. MEF2 baits used in the two-hybrid screens were GAL4-MEF2(1-86) and MEF2(1-117)-GAL4 (FIG. 9A). FIG. 9A shows HDACs 4 and 5 and the different regions of the proteins encoded by cDNAs rescued as "prey" in the two-hybrid screens. An 18 amino acid region in the N-terminal domains of both HDAC 4 and 5 comprises the MEF2-binding domain. This domain is absent in HDAC1, 2, 3 and 6 (FIG. 10).

EXAMPLE 11

HDAC 4 and HDAC 5 Bind to MEF2 and Repress MEF2 Activity

Cos cells were transiently transfected with expression vectors encoding HDACs with a Flag epitope, as indicated, and MEF2 A, C, or D. Cells were then lysed and extracts immunoprecipitated with anti-Flag antibody, followed by anti-MEF2 or anti-Flag western blot (FIG. 12). The top panel shows the results of anti-MEF2 western blots. HDACs 4 and 5, but not HDACs 1 or 3, interact with each MEF2 factor. The bottom panel shows the results of anti-Flag western blots and demonstrates the presence of comparable amounts of exogenous HDAC protein in each extract. These results indicate that both HDAC 4 and HDAC 5 interact with MEF2. A schematic diagram of the experiment is shown at the bottom.

Similarly, Cos cells were transiently transfected with expression vectors encoding HDAC 4, HDAC 5 or a deletion mutant lacking the N-terminus (HDAC 5-ΔN) with a Flag epitope and MEF2C. Cells were then lysed and extracts immunoprecipitated with anti-Flag antibody, followed by anti-MEF2 western blot (FIG. 13). The top panel shows the results of anti-Flag immunoprecipitation followed by anti-MEF2 western blot. The bottom panel shows the results of anti-MEF2 western blot without an immunoprecipitation reaction and demonstrates the presence of comparable amounts of exogenous HDAC protein in each extract. These data demonstrate that the N-terminus of HDAC 5 is required for an interaction between HDAC 5 and MEF2. A schematic diagram of the experiment is shown at the bottom.

In another example, Cos cells were transiently transfected with the MEF2 reporter plasmid, MEF2×2-luciferase, along with expression vectors encoding the indicated MEF2 factor, HDAC isoform or HDAC 5 lacking the amino-terminal MEF2 binding domain (FIG. 14). These data demonstrate that HDACs 4 and 5 repress transcriptional activity of MEF2A, MEF2C, and MEF2D. Replacement of the MEF2 transcription activation domain with VP16 reduces the ability of HDAC to repress. Also, HDAC 5 lacking the amino-terminus (HDAC 5ΔN) cannot repress.

Figure 15:
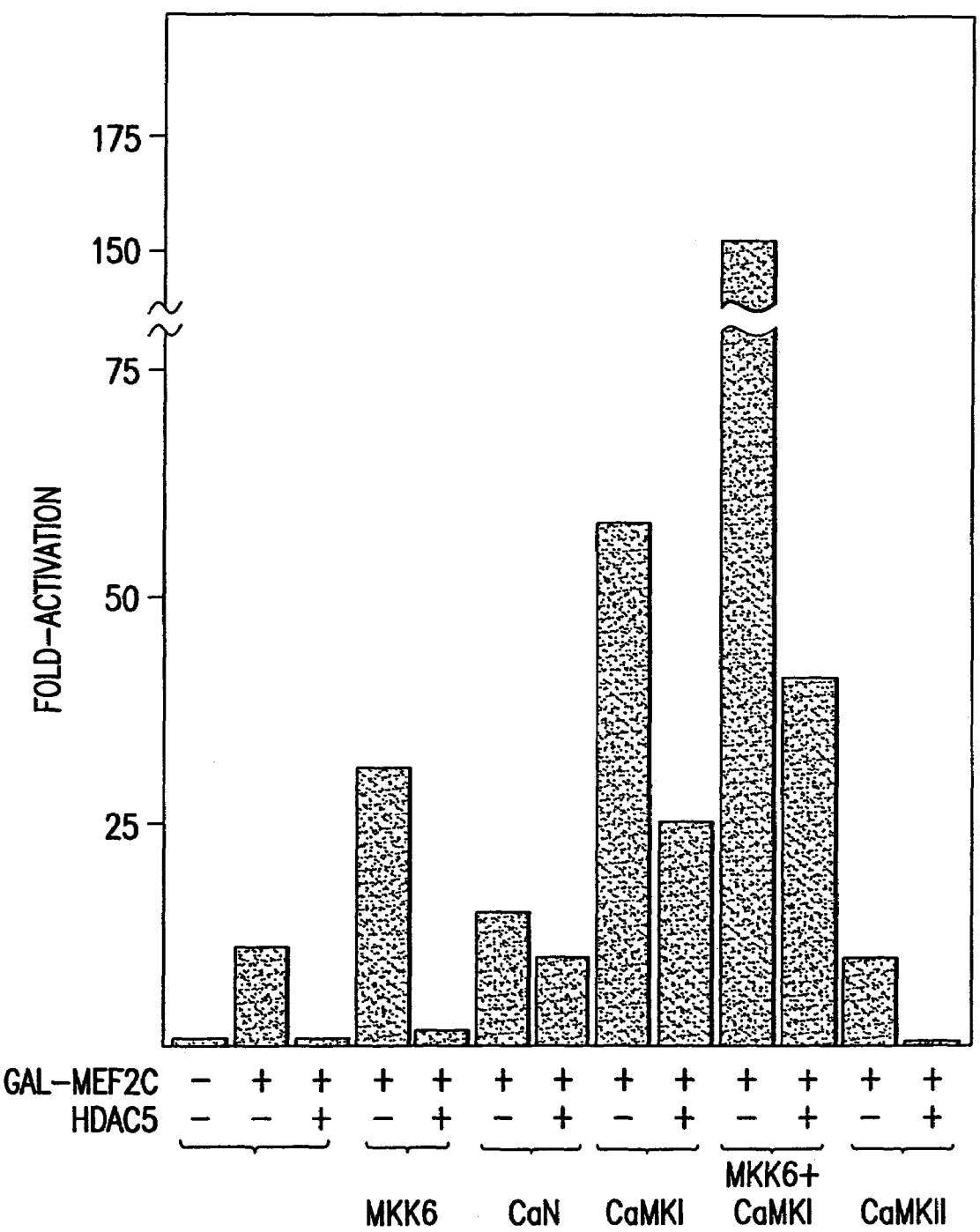
FIG. 15. Effects of HDAC 5 on activation of MEF2 by different signaling pathways. 10T1/2 fibroblasts were transiently transfected with a GAL4-dependent luciferase reporter (G5-luc) along with expression vectors encoding full length MEF2C fused to the GAL4 DNA binding domain (GAL-MEF2C) and vectors encoding the indicated signaling molecules. Two days later, cells were harvested and luciferase activity was measured. HDAC 5 blocks MEF2 activation in response to MKK6, calcineurin (CN) and CaM kinases.

The effects of HDAC 5 on activation of MEF2 by different signaling pathways were investigated. 10T1/2 fibroblasts were transiently transfected with a GAL4-dependent luciferase reporter (G5-luc) along with expression vectors encoding full length MEF2C fused to the GAL4 DNA binding domain (GAL-MEF2C) and vectors encoding the indicated signaling molecules. Two days later, cells were harvested and luciferase activity was measured (FIG. 15). It was observed, that HDAC 5 blocks MEF2 activation in response to MKK6, calcineurin (CN) and CaM kinases.

Figure 16:
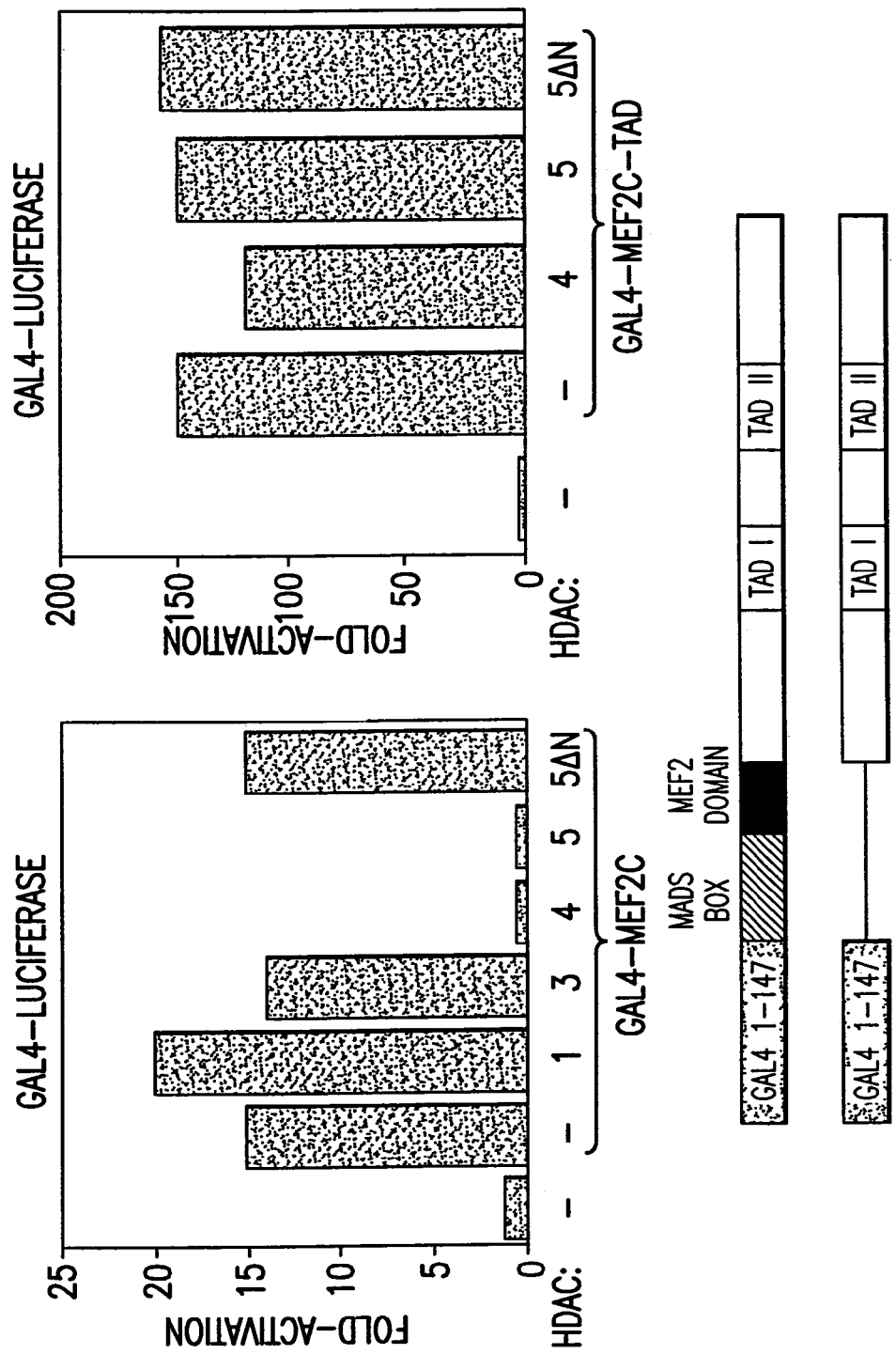
FIG. 16. Activated CaMKIV and MAP kinase MKK6 activate different domains of MEF2C. 10T1/2 cells were transiently transfected with a GAL4-dependent luciferase reporter and full length MEF2C fused to GAL4 (GAL4-MEF2C) or the carboxyl-terminal transactivation domain fused to GAL4 (GAL4-MEF2C-TAD) in the presence of the indicated HDACs. HDACs 4 and 5 repress full length MEF2C, but not the MEF2C transcription activation domain because it lacks the HDAC binding motif.

It was demonstrated also that activated CaMKIV and MAP kinase MKK6 activate different domains of MEF2C. 10T1/2 cells were transiently transfected with a GAL4-dependent luciferase reporter and full length MEF2C fused to GAL4 (GAL4-MEF2C) or the carboxyl-terminal transactivation domain fused to GALA (GAL4-MEF2C-TAD) in the presence of the indicated HDACs (FIG. 16). HDAC 4 and HDAC 5 repress full length MEF2C, but not the MEF2C transcription activation domain because it lacks the HDAC binding motif.

Figure 17:
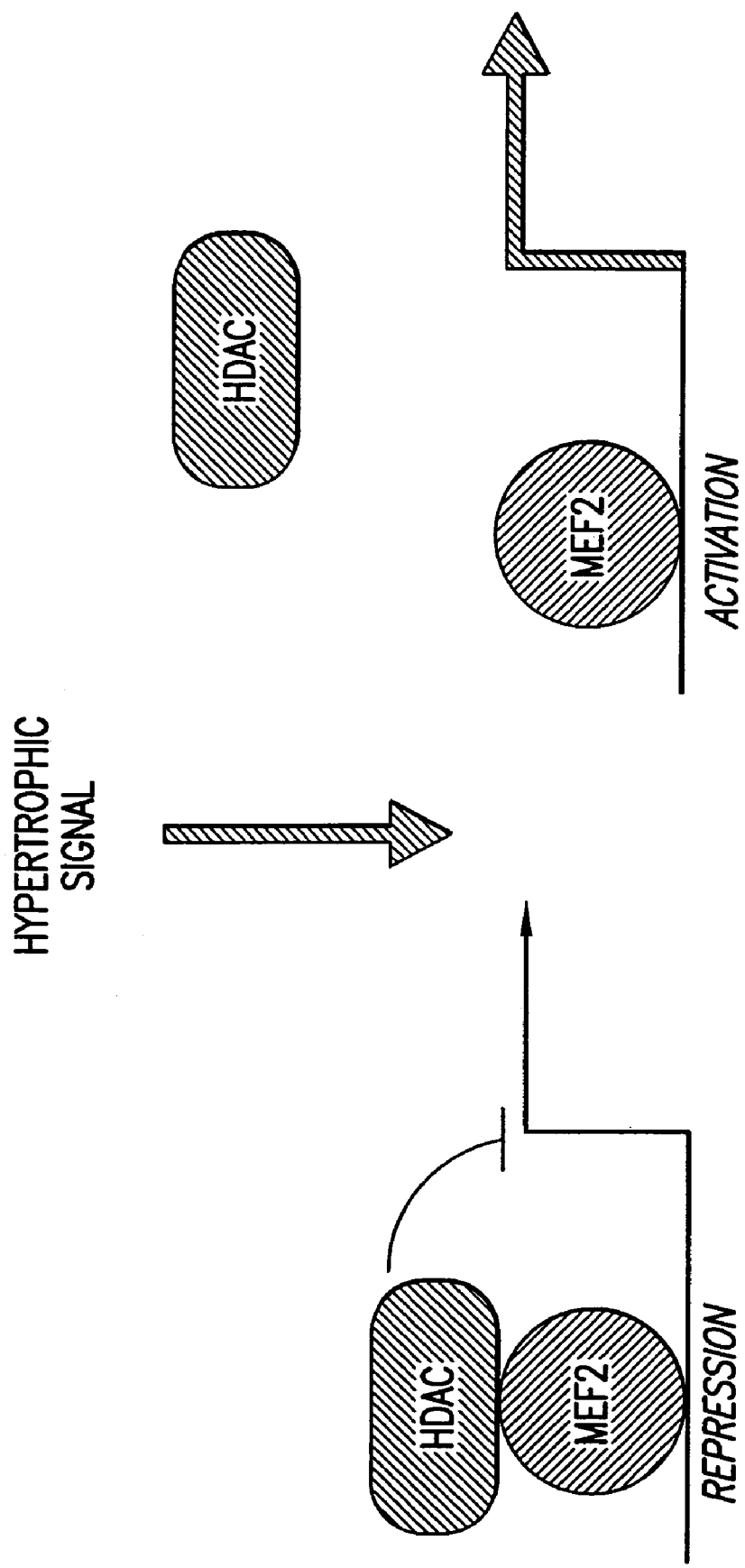
FIG. 17. Schematic diagram showing the disruption of MEF2-HDAC interaction by hypertrophic signals. Binding of HDAC 4 or 5 to MEF2 results in repression of MEF2-dependent genes in cardiomyocytes. Upon stimulation of cardiomyocytes with hypertrophic signals that activate CaM kinases, HDACs 4 and 5 are dissociated from MEF2 and downstream genes are activated, leading to hypertrophy.
Figure 18:
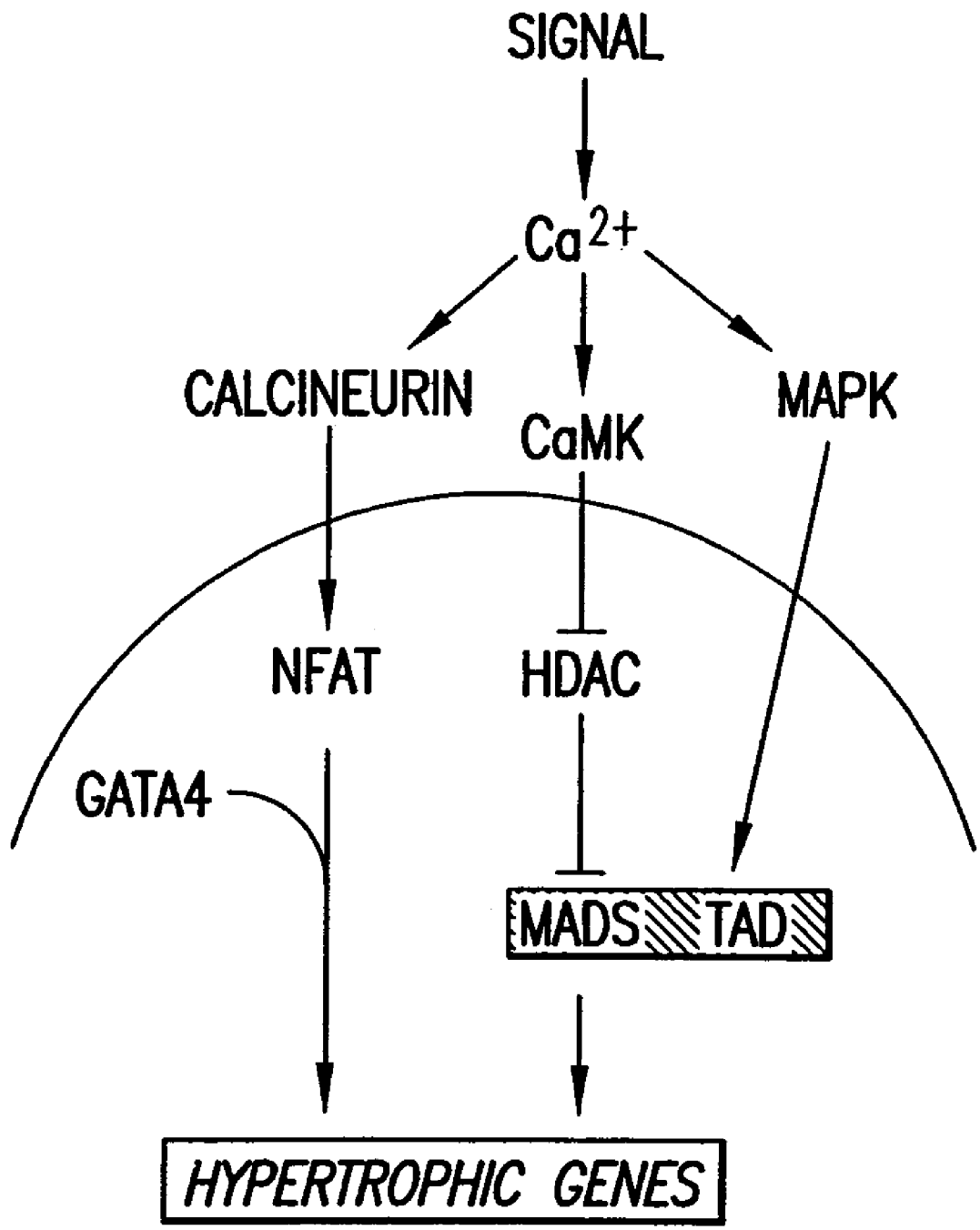
FIG. 18. Schematic diagram of parallel hypertrophic signaling pathways leading to NFAT and MEF2 activation.

A schematic diagram showing the disruption of MEF2-HDAC interaction by hypertrophic signals is depicted in FIG. 17. Binding of HDAC 4 or 5 to MEF2 results in repression of MEF2-dependent genes in cardiomyocytes. Upon stimulation of cardiomyocytes with hypertrophic signals that activate CaM kinases, HDACs 4 and 5 are dissociated from MEF2 and downstream genes are activated, leading to hypertrophy.

Example 12

Subcellular Localization of HDACS

Figure 19:
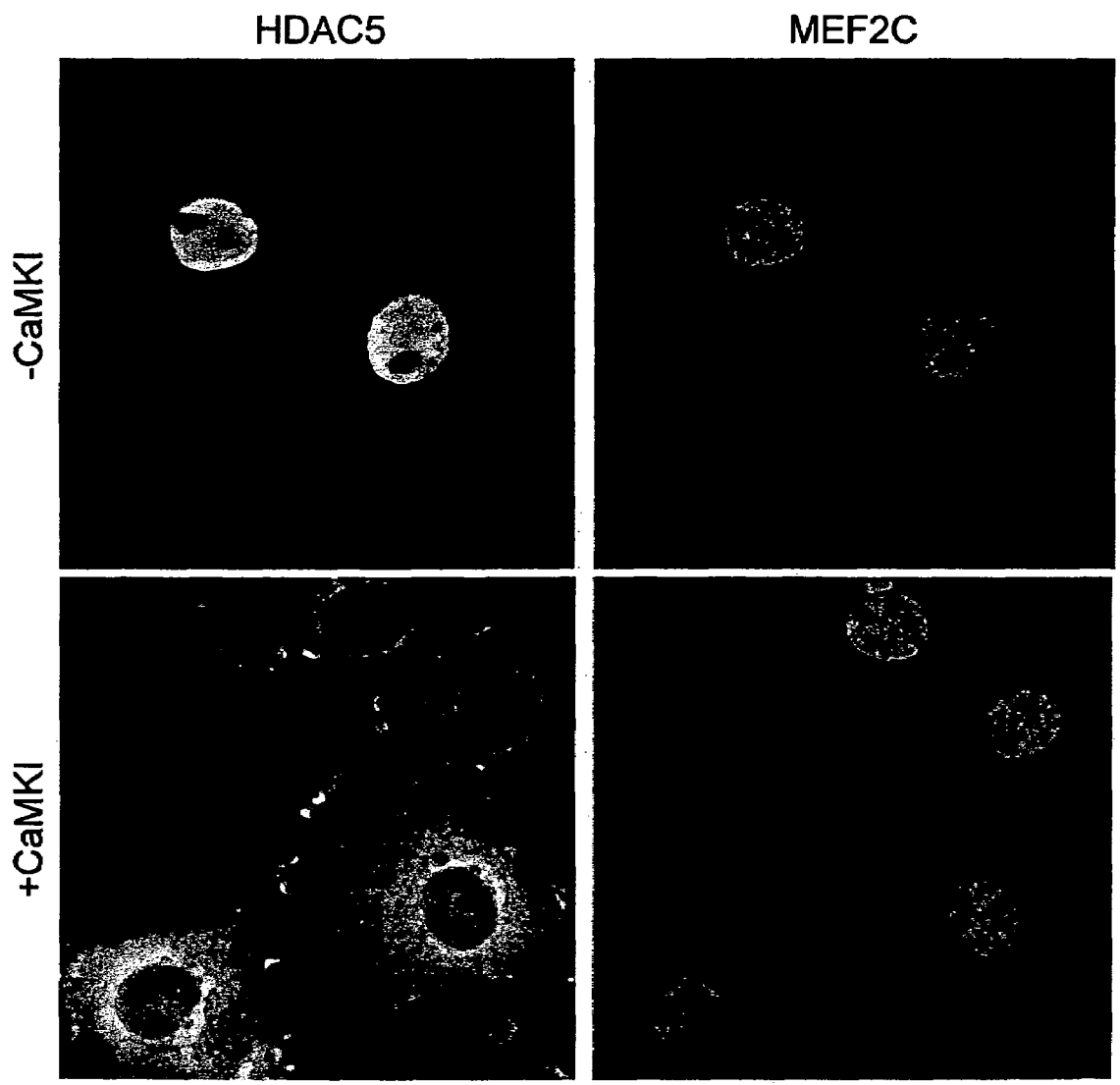
FIG. 19. Nuclear export of HDAC 5 in response to CaMK signaling. Cells expressing epitope-tagged HDAC 5 and MEF2C were analyzed by immunofluoroscence. In the absence of CaMK, HDAC 5 and MEF2 are associated in the nucleus. However, in cells in which CaMKI has been activated, HDAC 5 is excluded from the nucleus and MEF2 remains nuclear-localized.

The present inventors have shown that activation of CaM kinase signaling stimulates MEF2 activity and overcomes the inhibitory effects of HDACs. By immunoprecipitation experiments, they also have shown that activated CaM kinase acts by dissociating HDAC from MEF2, thereby enabling MEF2 to switch on its target genes involved in growth and hypertrophy. Deletion mapping experiments showed that HDACs are the target for the CaM kinase signal. In light of the ability of activated CaMK to overcome HDAC-mediated repression of MEF2 and dissociate the HDAC-MEF2 complex, the inventors chose to further investigae whether CaMK signaling also altered the subcellular distribution of HDAC 5 (FIG. 19).

In the absence of activated CaMK, MEF2C and HDAC 5 were coexpressed exclusively in the nucleus. In the contrast, HDAC 5 was cytoplasmic in cells expressing a constitutively active form of CaMKI or CaMKIV. MEF2C remained nuclear in CaMK-expressing cells, consistent with the finding that CaMK signaling disrupts MEF2-HDAC complexes and stimulates MEF2 dependent transcription.

In principle, nuclear exclusion of HDAC 5 could result from inhibition of nuclear import or stimulation of nuclear export. To distinguish between these possibilities, the subcellular distribution of an HDAC 5-green fluorescent protein (GFP) chimeric molecule was monitored in cells exposed to leptomycinB, a fungal toxin that blocks nuclear export. In CaMK1 expressing cells, HDAC 5 is localized to the cytoplasm. Treatment of CaMKI-expressing cells with leptomycinB resulted in translocation of HDAC 5 from the cytoplasm to the nucleus with a time course of 4 hours. These results demonstrate that nuclear import is unaffected by CaMK signaling and show that CaMK signaling stimulates nuclear export of HDAC 5.

Figure 20:
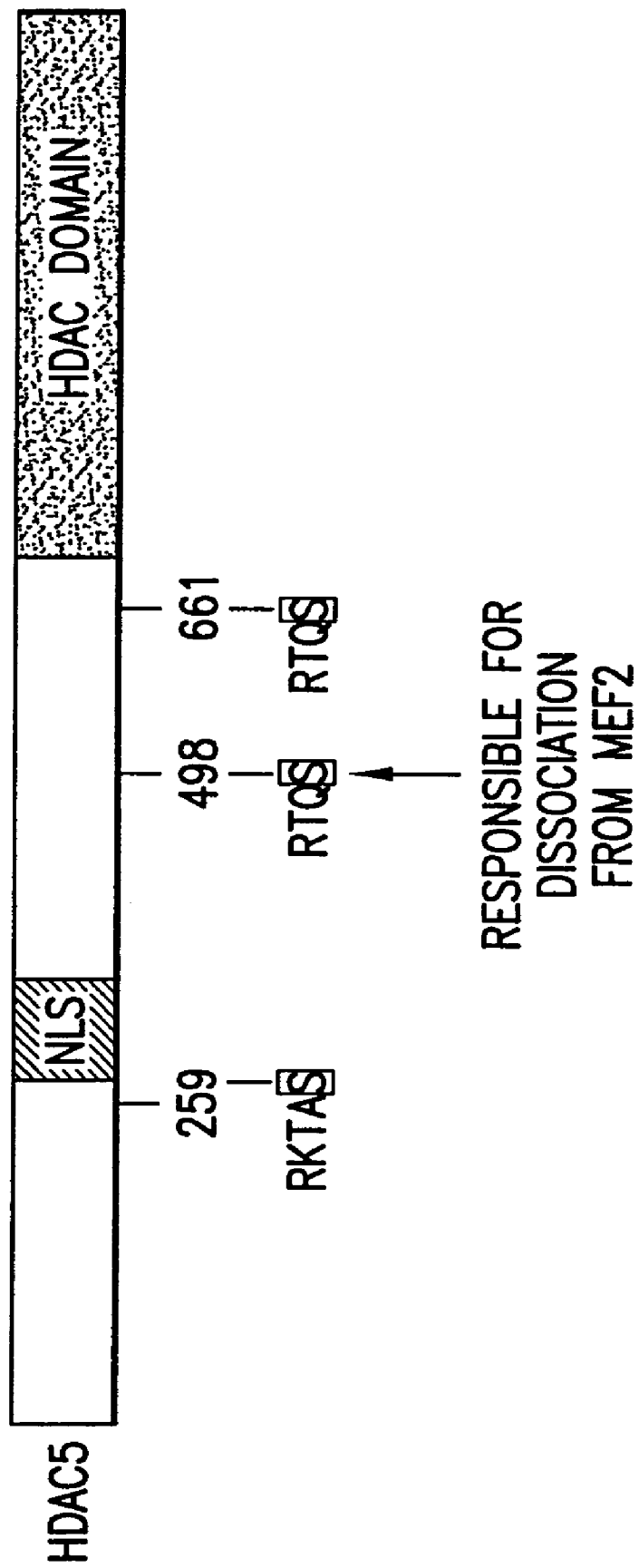
FIG. 20. Schematic diagram of HDAC 5 with positions of key phosphorylation sites. A diagram of HDAC 5 is shown with the position of the nuclear localization sequence (NLS) and carboxyl-terminal HDAC domains. Serines 259, 498, and 661 can each be phosphorylated and will recruit 14-3-3. Serine 498 is responsible for dissociation of MEF2 from HDAC following phosphorylation.

To identify sequences in HDAC 5 that control nuclear localization and responses to CaMK signaling, the inventors created a series of carboxyl-terminal truncation mutants of HDAC 5 and examined their subcellular distribution by indirect immunofluorescence. An analysis of approximately 18 mutants localized a specific region between residues 259 and 661 responsible for CaMK-dependent nuclear export. Phosphorylation mapping experiments, combined with extensive mutagenesis, identified three key phosphorylation sites in HDAC 5 (serines 259, 498, and 661), which can be phosphorylated in response to CaMK activation. Subsequent mutagenesis experiments demonstrated that serine 498 is the key amino acid responsible for detachment of HDAC from MEF2 following CaMK-dependent phosphorylation (FIG. 20).

To investigate the mechanisms that regulate CaMK-dependent phosphorylation and dissociation of HDAC 5 from MEF2, the inventors used amino-terminal portions of HDACs 4 and 5 as "baits" in two-hybrid screens of cDNA libraries in yeast to find interacting regulatory proteins. These studies resulted in the identification of over 100 cDNAs encoding different isoforms of the chaperone protein 14-3-3. Previous studies have demonstrated that 14-3-3 proteins bind to phosphoserine residues, and thus serve as intracellular phosphorylation-dependent chaperone proteins. Additional mutational analyses have shown that 14-3-3 binds HDAC 5 when phosphorylated at serines 259 and 498. 14-3-3 will also recognize phosphorylated residue 661, which appears to be constitutively phosphorylated in yeast and was therefore responsible for the initial detection of this interaction.

Figure 21:
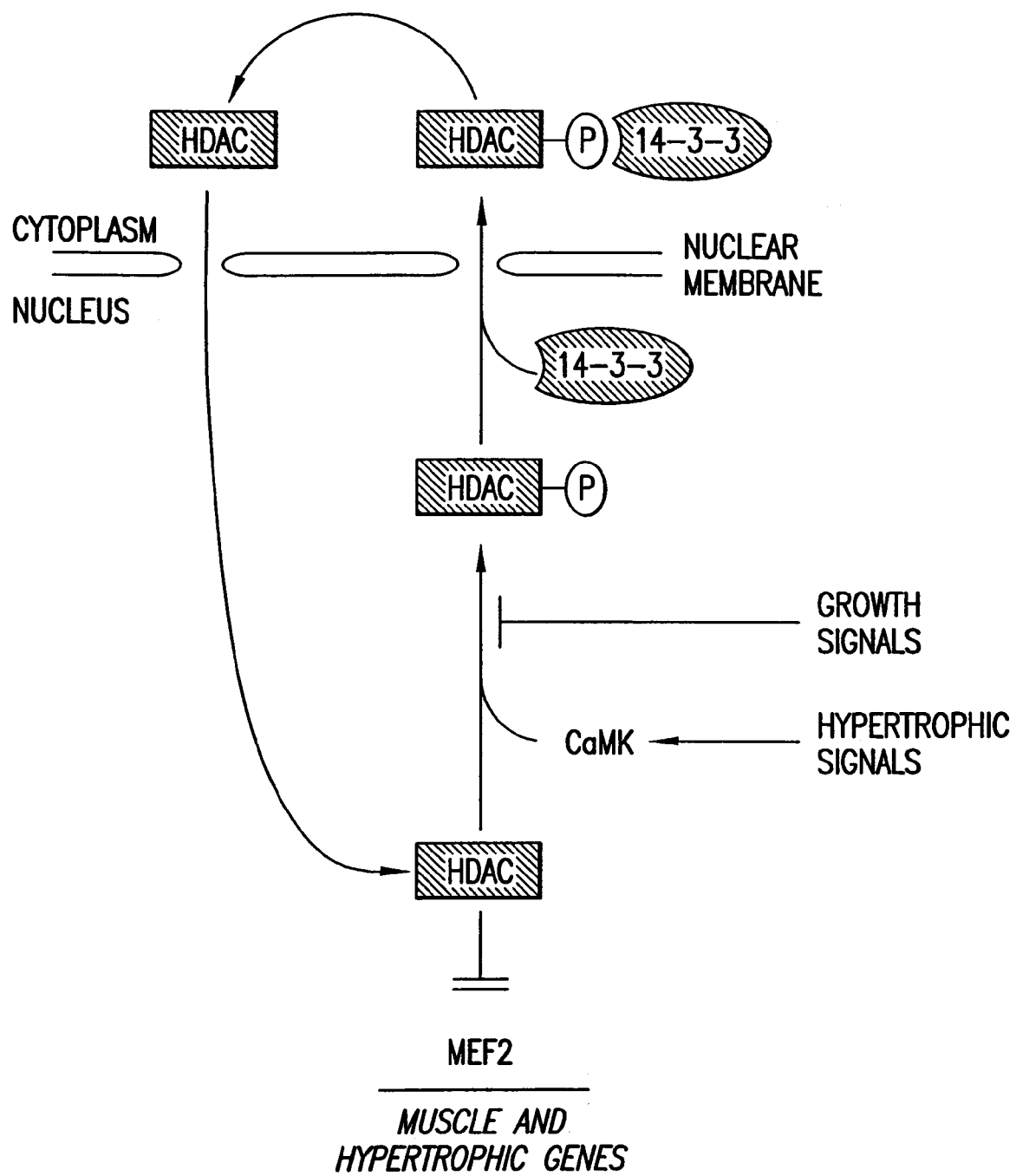
FIG. 21. Diagram of events involved in CaMK signaling and regulation of MEF2 activity by HDACs. Association of HDAC 5 with MEF2 results in repression of fetal muscle genes and other hypertrophic genes. CaMK signaling phosphorylates HDAC 5, preventing its association with MEF2.

According to the inventors current model, HDAC 5 exists in the nucleus as a complex with MEF2 to repress MEF2-dependent genes. Upon receipt of a CAMK signal, HDAC 5 is phosphorylated at residue 498 preventing its association with MEF2 and enabling its association with 14-3-3. Binding to 14-3-3 is then essential for escorting HDAC 5 from the nucleus to the cytoplasm (FIG. 21).

These experiments have pinpointed the precise molecular details of the mechanism through which hypertrophic signals involving CaMK can activate MEF2. They also suggest an assay for HDAC 5 kinases and for high throughput chemical screens to identify inhibitors of such kinases that are antihypertrophic. A schematic diagram of this type of assay is shown in FIG. 22. According to this assay, the region of HDAC 5 containing serine residues at 259 and 498 is fused to the GAL4 DNA binding domain and used as bait. This construct can then be expressed in yeast screens in which the GAL4 binding site is used to drive the expression of a LacZ reporter as well as positive or negative selectable markers. Plasmids containing 14-3-3 fused to the GAL4 transcription activation domain would also be introduced into the yeast strain, but they could not associate with HDAC 5 "bait" because serine 259 and 498 within HDAC 5 do not appear to be phosphorylated in yeast. Thus, interaction between the 14-3-3 "prey" and HDAC "bait" would require phosphorylation. Introduction of cDNA libraries from human hearts into yeast will identify kinases that phosphorylate HDAC on the basis of the ability to reconstitute the interaction between 14-3-3 and HDAC. In addition, this same system can be used for high throughput drug screens to identify antihypertrophic compounds that perturb this same interaction.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,359,046
U.S. Pat. No. 4,367,110
U.S. Pat. No. 4,452,901
U.S. Pat. No. 4,668,621
U.S. Pat. No. 4,873,191
U.S. Pat. No. 5,708,158
U.S. Pat. No. 5,252,479
U.S. Pat. No. 5,672,344
WO 84/03564
Adolph et al., "Role of myocyte-specific enhancer-binder factor (MEF-2) in transcriptional regulation of the acardiac myosin heavy chain gene," *J. Biol. Chem.*, 268:5349-5352, 1993.
Baichwal and Sugden, In: *Gene Transfer*, Kucherlapati R, ed., New York, Plenum Press, 117-148, 1986.
Batterson and Roizman, *J. Virol.*, 46:371-377, 1983.
Bedzyk et al., *J. Biol. Chem.*, 265:18615, 1990.
Bellon et al., *de Ses Filiales*, 190(1):109-142, 1996.
Benvenisty and Neshif, *Proc. Nat'l Acad. Sci. USA*, 83:9551-9555, 1986.
Berns and Bohenzky, *Adv. Virus Res.*, 32:243-307, 1987.
Berns and Giraud, *Curr. Top. Microbiol. Immunol.*, 218:1-23, 1996.
Berns, *Microbiol Rev.*, 54:316-329, 1990.
Bertran et al., *J. Virol.*, 70(10):6759-6766, 1996.
Bito et al., "CREB Phosphorylation and Dephosphorylation: Aca2+− and Stimulus Duration-Dependent Switch for Hippocampal Gene Expression," *Cell*, 87:1203-1214, 1996.
Botinelli et al., *Circ. Res.* 82:106-115, 1997.

Bour et al., "Drosophila MEF2, a transcription factor that is essential for myogenesis," *Genes and Dev.*, 9:730-741, 1995.

Bowman et al., "Expression of Protein Kinase C B in the Heart Causes Hypertrophy in Adult Mice and Sudden Death in Neonates," *J. Clin. Invest.*, 100:2189-2195, 1997.

Brand, "Myocyte enhancer factor 2 (MEF2)," *Int J. Biochem. Cell Biol*, 29:1467-1470; 1997.

Brinster et al., *Proc. Nat'l Acad. Sci. USA*, 82: 4438-4442, 1985.

Brown et al., *J. Neurochem.* 40:299-308, 1983.

Bustamante et al., *J. Cardiovasc. Pharmacol*, 17:S110-113, 1991.

Chaudhary et al., *Proc. Nat'l Acad. Sci*, 87:9491, 1990.

Chen and Okayama, *Mol. Cell Biol.*, 7:2745-2752, 1987.

Chien et al., *Ann. Rev. Physiol.* 55, 77-95, 1993.

Chien et al., "Regulation of cardiac gene expression during myocardial growth and hypertrophy: Molecular studies of an adaptive physiologic response," *FASEB J.*, 5:3037-3046, 1991.

Chomczynski and Sacchi, *Anal. Biochem.*, 162:156-159, 1987.

Clarke et al., "Epidermal Growth Factor Induction of the c-jun Promoter by a Rac Pathway," *Mol. Cell Biol.*, 18:1065-1073, 1998.

Coffin, In: Fields B N, Knipe D M, ed. VIROLOGY. New York: Raven Press, pp. 1437-1500,1990.

Colbert et al., "Cardiac Compartment-specific Overexpression of a Modified Retinoic Acid Receptor Produces Dilated Cardiomyopathy and Congestive Heart Failure in Transgenic Mice," *J. Clin. Invest.*, 100:1958-1968, 1997.

Coso et al., "Signaling from G Protein-coupled Receptors to the c-jun promoter Involves the MEF2 Transcription Factor," *J. Biol. Chem.*, 272:20691-20697, 1997.

Couch et al., *Am. Rev. Resp. Dis.*, 88:394-403, 1963.

DeLuca et al., *J. Virol.*, 56:558-570, 1985.

Dolmetsch et al., "Differential activation of transcription factors induced by Ca2+ response amplitude and duration," *Nature*, 386:855-858, 1997.

Dubensky et al., *Proc. Nat'l Acad. Sci. USA*, 81:7529-7533, 1984.

Edmondson et al., "MEF2 gene expression marks the cardiac and skeletal muscle lineages during mouse embryogenesis," *Development*, 120:1251-1263, 1994.

Ellis et al., "Replacement of insulin receptor tyrosine residues 1162 and 1163 compromises insulin-stimulated kinase activity," 1986.

Elroy-Stein et al., *Proc. Nat'l Acad. Sci. USA*, 1989.

Elshami et al., *Gene Therapy*, 7(2):141-148, 1996.

Emmel et al., "Cyclosporin A specifically inhibits function of nuclear proteins involved in T cell activation," *Science*, 246:1617-1620, 1989.

Evans, "Regulation of Cardiac Gene Expression by GATA-4/5/6," *Trends in Cardiovascular Medicine*, 7:75-83, 1997.

Fechheimer et al., *Proc. Nat'l. Acad. Sci. USA*, 84:8463-8467, 1987.

Feldman et al., "Selective Gene Expression in Failing Human Heart," *Circulation*, 83:1866-1872, 1991.

Ferkol et al., *FASEB J.*, 7:1081-1091, 1993.

Fischele et al., *J. Biol. Chem.*, 274:11713-11720, 1999.

Flanagan et al., "Nuclear association of a T-cell transcription factor blocked by FK-506 and cyclosporin A," *Nature*, 352:803-807, 1991.

Fraley et al., *Proc. Nat'l Acad. Sci. USA*, 76:3348-3352, 1979.

French et al., *Circulation*, 90(5):2414-2424, 1994.

Freshner, In *Animal Cell Culture: a Practical Approach* Second Edition, Oxford/New York, IRL Press, Oxford University Press, 1992.

Ghosh-Choudhury et al., *EMBO J.*, 6:1733-1739, 1987.

Ghosh and Bachhawat, (Wu G, Wu C ed.), New York: Marcel Dekker, pp. 87-104, 1991.

Ginsberg et al., *Proc. Nat'l Acad. of Sci. USA*, 88(5)1651-1655, 1991.

Glorioso et al., *Ann. Rev. Microbiol.* 49:675-710, 1995.

Gomez-Foix et al., *J. Biol. Chem.*, 267:25129-25134, 1992.

Gopal, *Mol. Cell Biol.*, 5:1188-1190, 1985.

Gossen and Bujard, "Tight control of gene expression in mammalian cells by tetracycline-responsive promoters," *Proc. Nat'l Acad. Sci.*, 89:5547-5551, 1992.

Gossen et al., *Science*, 268:1766-1769, 1995.

Graham and Prevec, *Biotechnology*, 20:363-390, 1992.

Graham and Prevec, In: E. J. Murray (ed.), Methods in Molecular Biology: Gene Transfer and Expression Protocol, Clifton, N.J.: Humana Press, 7:109-128, 1991.

Graham and Van Der Eb, *Virology*, 52:456-467, 1973.

Graham et al, *J. Gen. Virol.*, 36:59-72, 1977.

Grepin et al., *Mol. Cell. Biol.*, 14:3115-3129, 1994.

Grozinger et al., *Proc. Nat'l. Acad. Sci.*, 96:4868-4873, 1999.

Grunhaus and Horwitz, *Seminar in Virology*, 3:237-252, 1992.

Gruver et al, "Targeted developmental overexpression of calmodulin induces proliferative and hypertrophic growth of cardiomyocytes in transgenic mice," *Endocrinology*, 133:376-388, 1993.

Han et al, "Activation of the transcription factor MEF2C by the MAP kinase p38 in inflammation," *Nature*, 386:296-299, 1997.

Harland and Weintraub, *J. Cell Biol.*, 101:1094-1099, 1985.

Harlow et al, *Antibodies: A Laboratory Manual*, Cold Spring Harbor, N.Y., 1988.

Hasegawa et al, "Cis-acting sequences that mediate induction of the -myosin heavy chain gene expression during left ventricular hypertrophy due to aortic constriction," *Circulation*, 96:3943-3953, 1997.

Haverich et al., *Transplant Proc.*, 26:2713-2715, 1994.

Hersdorffer et al, *DNA Cell Biol.*, 9:713-723, 1990.

Herz and Gerard, *Proc. Nat'l Acad. Sci. USA*, 90:2812-2816, 1993.

Herzig et al, "Angiotensin II type 1a receptor gene expression in the heart: AP-1 and GATA-4 mediate the response to pressure overload," *Proc. Nat'l Acad. Sci. USA*, 94:7543-7548, 1997.

Ho et al, *J. Biol. Chem.*, 270:19898-19907, 1995.

Ho et al, "Activation of protein I-dependent transcriptional activation of interleukin 2 gene by $Ca^{++}$/calmodulin kinase type IV/Gr," *J. Exp. Med.*, 184:101-112, 1996.

Hoey et al, "Isolation of two new members of the NF-AT gene family and functional characterization of the NF-AT proteins," *Immunity*, 2:461-472, 1995.

Hogan et al., "*Manipulating the Mouse Embryo*" Cold Spring Harbor Laboratory, Cold Spring Harbor, N.Y., 1986.

Holland et al., *Virology*, 101:10-18, 1980.

Honess and Roizman, *J. Virol.*, 14:8-19, 1974.

Honess and Roizman, *J. Virol.*, 16:1308-1326, 1975.

Hongo et al., *Am. J. Physiol.*, 269:C690-C697, 1995.

James and Olson, "Deletion of the regulatory domain of protein kinase C exposes regions in the hinge and catalytic domains that mediate nuclear targeting," *J. Cell Biol.*, 116: 863-874, 1992.

Johnson et al., *BIOTECHNOLOGY AND PHARMACY*, Pezzuto et al., eds., Chapman and Hall, New York, 1993.

Jones and Shenk, *Cell*, 13:181-188, 1978.

Jones et al., *J. Clin. Invest.*, 98:1906-1917, 1996.

Jones, Sanchez, Robbins, "Murine pulmonary myocardium: developmental analysis of cardiac gene expression," *Dev. Dyn.*, 200:117-128, 1994.

Kaneda et al., *Science*, 243:375-378, 1989.

Kao et al., "Isolation of a novel histone deacetylase reveals that class I and class II deacetylases promote SMRT-mediated repression," *Genes Dev.*, 14(1):55-66, 2000

Kariya et al., "An enhancer core element mediates stimulation of the rat-myosin heavy chain promoter by an $_1$-adrenergic agonist and activated -protein kinas C in hypertrophy of cardiac myocytes," *J. Biol. Chem.*, 269:3775-3782, 1994.

Karliner et al., "Effects of pertussis toxin on 1-agonist-mediated phosphatidylinositide turnover anh myocardial cell hypertrophy in neonatal rat myocytes," *Experientia.*, 46:81-84, 1990.

Karlsson et al., *EMBO J.*, 5:2377-2385, 1986.

Karns et al., "M-CAT, CarG, and Sp1 elements are required for $_1$-adrenergic induction of the skeletal-actin promoter during cardiac myocyte hypertrophy," *J. Biol. Chem.*, 270:410-417, 1995.

Kato et al., *J. Biol. Chem.*, 266:3361-3364, 1991.

Kato et al., "BMK1/ERK5 regulates serum-induced early gene expression through transcription factor MEF2C," *EMBO J.*, 16:054-066, 1997.

Kearns et al., *Gene Ther.*, 3:748-755, 1996.

Kincaid et al., "Cloning and characterization of molecular isoforms of the catalytic subunit of calcineurin using nonisotopic methods," *J. Biol. Chem.*, 265:11312-11319, 1990.

Klein et al, *Nature*, 327:70-73, 1987.

Komuro and Yazaky, "Control of cardiac gene expression of mechanical stress," *Annu. Rev. Physiol.*, 55:55-75, 1993.

Kotin and Berns, *Virol.*, 170:460-467, 1989.

Kotin et al., *Genomics*, 10:831-834, 1991.

Kotin et al., *Proc. Nat'l Acad. Sci. USA*, 87:2211-2215, 1990.

Kovacic-Milivojevic et al, *Endocrin*, 137:1108-1117, 1996.

Kovacic-Milivojevic et al, "Selective regulation of the atrial natriuretic peptide gene by individual components of the activator protein-1 complex," *Endocrinology*, 137:1008-1117, 1996.

Kudoh et al, *Circ. Res.*, 80:139-146, 1997.

LaPointe et al., *Hypertension*, 27:715-722, 1996.

Le Gal La Salle et al, *Science*, 259:988-990, 1993.

Le Guennec et al, *Exp. Physiol.*, 6:975-978, 1991.

Lee et al., "Myocyte-Specific Enhancer Factor 2 and Thyroid Hormone Receptor Associate and Synergistically Activate the α-Cardiac Myosin Heavy-Chain Gene," *Mol. Cell Biol.*, 17:2745-2755, 1997.

Leite et al, "Regulation of ANP secretion by endothelin-1 in cultured atrial myocytes: desensitization and receptor subtype," *Am. J. Physiol.*, 267:H2193-2203, 1994.

Levrero et al, *Gene*, 101:195-202, 1991.

Li et al, "FGF inactivates myogenic helix-loop-helix proteins through phosphorylation of a conserved protein kinase C site in their DNA binding domains," *Cell*, 71:1181-1194, 1992.

Lilly et al, "Requirement of MADS domain transcription factor D-MEF2 for muscle formation in Drosophila," *Science*, 267:688-693, 1995.

Lin et al., *J. Clin. Invest.*, 97:2842-2848, 1996.

Lin et al, "Control of cardiac morphogenesis and myogenesis by the myogenic transcription factor MEF2C," *Science*, 276:1404-1407, 1997.

Liu et al, "Cyclosporin A-sensitive induction of the Epstein-Barr virus lytic switch is mediated via a novel pathway involving a MEF2 family member," *EMBO J.*, 16:143-153, 1997.

Loh et al, *J. Biol. Chem.*, 271:10884-10891, 1996b.

Loh et al, *Mol Cell. Biol.*, 16:3945-3954, 1996a.

Lyakh et al, *Mol Cell. Biol.*, 17:2475-2482, 1997.

Mann et al, *Cell*, 33:153-159, 1983.

Marban et al, *Proc. Nat'l Acad. Sci. USA*, 84:6005-6009, 1987.

Markowitz et al, *J. Virol.*, 62:1120-1124, 1988.

Martin et al, "Myocyte enhancer factor (MEF) 2C: A tissue-restricted member of the MEF-2 family of transcription factors," *Proc. Nat'l Acad. Sci. USA*, 90:5282-5286, 1993.

Masuda et al, *Mol. Cell. Biol.*, 15:2697-2706, 1995.

Masuda et al, "NF-ATx, a novel member of the nuclear factor of activated T cells family that is expressed predominately in the thymus," *Mol. Cell. Biol.*, 15:2697-2706, 1995.

McCaffery et al, *Science*, 262:750-754, 1993.

Mercadier et al, "Altered sarcoplasmic reticulum $Ca^{++}$-ATPase gene expression in the human ventricle during end-stage heart failure," *J. Clin. Invest.*, 85:305-309, 1995.

Mizukami et al, *Virology*, 217:124-130, 1996.

Molkentin and Olson, "Combinational Control of Muscle Development by bHLH and MADS-box Transcription Factors," *Proc. Nat'l Acad. Sci. USA*, 93:9366-9373, 1996.

Molkentin and Olson, *Circulation*, 96:3833-3835, 1997.

Molkentin et al, *Mol Cell Biol.*, 16:2627-2536, 1996.

Molkentin et al, *Mol Cell. Biol.*, 14:4947-4957, 1994.

Molkentin, et al., "Cooperative activation of muscle gene expression by MEF2 and myogenic bHLH proteins," *Cell*, 83:1125-1136, 1995.

Molkentin et al., "Mutational analysis of the DNA binding, dimerization, and transcriptional activation of MEF2C," *Mol. Cell. Biol.*, 16:2627-2636, 1996a.

Molkentin et al., "MEF2B is a potent transactivator expressed in early myogenic lineages," *Mol. Cell. Biol.*, 16:3814-3824, 1996b.

Molkentin et al., "Phosphorylation of the MADS-box transcription factor MEF2C enhances its DNA binding activity," *J. Biol. Chem.*, 271:17199-17204, 1996c.

Molkentin et al., "Requirement of the GATA4 Transcription factor for heart tube formation and ventral morphogenesis," *Genes and Dev.*, 11:1061-1072, 1997.

Morgan et al., *Annu. Rev. Physiol.*, 49:533-543, 1987.

Mulligan, *Science*, 260:926-932, 1993.

Myers, EPO 0273085.

Nicolas and Rubenstein, In: *Vectors: A survey of molecular cloning vectors and their uses*. Rodriguez and Denhardt (eds.), Stoneham: Butterworth, pp. 494-513, 1988.

Nicolau and Sene, *Biochem. Biophys. Acta*, 721:185-190, 1982.

Nicolau et al., *Methods Enzymol.*, 149:157-176, 1987.

Northrop et al., *Nature*, 369:497-502, 1994.

Northrop et al., "NF-AT components define a family of transcription factors targeted in T-cell activation," *Nature*, 369:497-502, 1994.

O'Keefe, Tamura, Kincaid, Tocci, O'Neill, "FK506- and CsA-sensitive activation of the interleukin-2 promoter by calcineurin," *Nature*, 357:692-694, 1992.

Ogawa et al., *J. Mol. Med.*, 73:457-463, 1995.

Ogawa, *Neuropathologica*, 77(3):244-253, 1989.

Olson et al., "Regulation of muscle differentiation by the MEF2 family of MADS box transcription factors," *Developmental Biology*, 172:2-14, 1995.

Ostrove et al., *Virology*, 113:532-533, 1981.

Palmiter and Solaro, *Basic. Res. Cardiol.*, 92:63-74, 1997.

Palmiter et al., *Nature*, 300:611, 1982.

Paradis et al., "Serum response factor mediates AP-1 dependent induction of the skeletal α-actin promoter in ventricular myocytes" *J. Biol. Chem.*, 271:10827-10833, 1996.

Park et al., "Characterization of a new isoform of the NF-AT (nuclear family of activated T cells) gene family member NF-ATc," *J. Biol. Chem.*, 271:20914-20921, 1996.

Paskind et al., *Virology*, 67:242-248, 1975.

Perales et al., *Proc. Nat'l Acad. Sci.*, 91:4086-4090, 1994.

Perreault et al., *Am. J. Physiol.*, 266:H2436-H2442, 1994.

Ponnazhagan et al., *Hum. Gene Ther.*, 8:275-284, 1997a.

Ponnazhagan et al., *J. Gen. Virol.*, 77:1111-1122, 1996.

Post et al., *Cell*, 24:555-565, 1981.

Potter et al., *Proc. Nat'l Acad. Sci. USA*, 81:7161-7165, 1984.

Racher et al., *Biotechnology Techniques*, 9:169-174, 1995.

Radler et al., *Science*, 275:810-814, 1997.

Ragot et al., *Nature*, 361:647-650, 1993.

Ramirez et al., "The Nuclear ob isoform of Ca2+/Calmodulin-dependent Protein Kinase Ii Regulates Atrial Natriuretic Factor Gene Expression in Ventricular Myocytes," *J. Biol. Chem.*, 272:31203-31208, 1997.

Rao et al., *Ann. Rev. Immunol*, 15:707-747, 1997.

Rao et al., "Transcription factors of the NF-AT family: Regulation and function," *Ann. Rev. Immunol.*, 15:707-747, 1997.

Reid and Yacoub, "Determinants of left ventricular function one year after cardiac transplantation," *Br. Heart J.*, 59:397-402, 1988.

Reid and Yancoub, *Br. Heart J.*, 59:397-402, 1988.

Renan, *Radiother. Oncol.*, 19:197-218, 1990.

Rich et al., Hum. Gene Ther., 4:461-476, 1993.

Ridgeway, In: Rodriguez R L, Denhardt D T, ed. Vectors: A survey of molecular cloning vectors and their uses. Stoneham: Butterworth, pp. 467-492, 1988.

Rippe et al., *Mol. Cell Biol.*, 10:689-695, 1990.

Roizman and Sears, In Fields' Virology, 3rd Edition, eds. Fields et al. (Raven Press, New York, N.Y.), pp. 2231-2295, 1995.

Rooney et al., "A common factor regulates both Th1- and The-specific cytokine gene expression," *EMBO J.*, 13:625-633, 1994.

Rosenfeld et al., *Cell*, 68:143-155, 1992.

Rosenfeld et al., *Science*, 252:431-434, 1991.

Roux et al., *Proc. Nat'l Acad. Sci. USA*, 86:9079-9083, 1989.

Sadoshima and Izumo, "Signal transduction pathways of angiotensin 1-induced c-fos gene expression in cardiac myocytes in vitro," *Circ. Res.*, 73:424-438, 1993b.

Sadoshima and Izumo, "The cellular and molecular response of cardiac myocytes to mechanical stress," *Ann. Rev. Physiol.*, 59:551-571, 1997.

Sadoshima et al., "Autocrine release of angiotensin II mediates stretch-induced hypertrophy of cardiac myocytes in vitro," *Cell*, 75:977-984, 1993a.

Saeki et al., *Adv. Exp. Med. Biol.*, 332:639-647, 1993. Sambrook et al., Molecular Cloning: A Laboratory Manual Cold Spring Harbor Laboratory, Cold Spring Harbor, N.Y., 1989.

Samulski et al., *EMBO J.*, 10:3941-3950, 1991.

Schwartz et al., *Circ. Res.* 59:551-555, 1986.

Schwinger et al., "Unchanged protein levels of SERCA II and phospholamban but reduced $Ca^{2+}$-ATPase activity of cardiac sarcoplasmic reticulum from dilated cardiomyopathy patients compared with patients with nonfailing hearts," *Circulation*, 92:3220-3228, 1995.

Shiraishi et al., *Transplant International*, 10(3):202-206, 1997.

Smith and Moss, *Gene*, 25:21-28, 1983.

Song et al., *Science*, 275:536-540, 1997.

Srivastava et al., *J. Virol.*, 45:555-564, 1983.

Stemmer and Klee, "Dual calcium ion regulation of calcineurin by calmodulin and calcineurin B," *Biochemistry*, 33:6859-6866, 1994.

Stratford-Perricaudet and Perricaudet, In: Human Gene Transfer, Eds. O. Cohen-Haguenauer and M. Boiron, Editions John Libbey Eurotext, France, pp. 51-61, 1991.

Su et al., "Distribution and activity of calcineurin in rat tissues. Evidence for post-transcriptional regulation of testis-specific calcineurin B," *Eur. J. Biochem.* 230:469-474, 1995.

Tate-Ostroffet al., *Proc. Nat'l Acad. Sci USA.*, 86:745-749, 1989.

Temin, In: Gene Transfer, Kucherlapati (ed.), New York: Plenum Press, pp. 149-188, 1986.

Terzic et al., "Cardiac α-1 adrenoceptors: an overview," *Pharm. Rev.*, 45:147-175, 1993.

The Qiagenologist, Application Protocols, 3rd edition, published by Qiagen, Inc., Chatsworth, Calif.

Thorburn et al., "HRas dependent pathways can activate morphological and genetic markers of cardiac muscle cell hypertrophy," *J. Biol. Chem.*, 268:2344-2349, 1993.

Thuerauf and Glembotski, *J. Biol. Chem.*, 272:7464-7472, 1997.

Thuerauf and Glembotski, "Differential effects of protein kinase C, Ras, and Raf-1 kinase on the induction of the cardiac B-type natriuretic peptide gene through a critical promoter-proximal M-CAT element," *J. Biol. Chem.*, 272:7464-7472, 1997.

Top et al., *J. Infect. Dis.*, 124:155-160, 1971.

Tur-Kaspa et al., *Mol. Cell Biol.*, 6:716-718, 1986.

Van Lint et al., *Gene Exp.*, 5:245-253, 1996.

Verdel and Khochbin, *J. Biol. Chem.*, 274:2440-2445, 1999.

Varmus et al., *Cell*, 25:23-36, 1981.

Vikstrom and Leinwand, *Curr. Opin. Cell Biol.*, 8:97-105, 1996.

Wagner et al., *Proc. Nat'l Acad. Sci.*, 87(9):3410-3414, 1990.

Watkins et al., *Hum. Mol. Genet.*, 4:1721-1727, 1995.

Werthman et al., *J. of Urology*, 155(2):753-756, 1996.

Wolfe et al., "Unusual Rel-like architecture in the DNA-binding domain of the transcription factor NFATc," *Nature*, 385:172-176, 1997.

Wong et al., *Gene*, 10:87-94, 1980.

Woods and Ellis, In: Laboratory Histopathology: A Complete Reference. p 7.1-13. Churchill Livingstone Publishers, New York, 1994.

Workman and Kingston, "Alteration of nucleosome structure as a mechanism of transcriptional regulation," *Annu. Rev. Biochem.*, 67:545-579, 1998.

Woronicz et al., "Regulation of the Nur77 Orphan Steroid Receptor in Activation-Induced Apoptosis," *Mol. Cell. Biol.*, 6364-6376, 1995.

Wu & Wu, *Biochemistry*, 27:887-892, 1988.

Wu & Wu, *J. Biol. Chem.*, 262:4429-4432, 1987.

Wu and Wu, *Adv. Drug Delivery Rev.*, 12:159-167, 1993.

Yamazaki et al., *J. Biol. Chem.*, 271:3221-3228, 1996.

Yamazaki et al., *Circulation*, 95:1260-1268, 1997.

Yang et al., *Proc. Nat'l Acad. Sci USA*, 87:9568-9572, 1990.

Yu et al., "Conditional transgene expression in the heart," *Circ. Res.*, 75:691-697, 1996.

Zou et al., *J. Biol. Chem.*, 271:33592-33597, 1996.

What is claimed is:

1. A transgenic mouse lacking one or more functional alleles of histone deacetylase (HDAC) 5, wherein said transgenic mouse exhibits a substantially increased probability of developing cardiac hypertrophy as compared to a littermate that does not lack one or more functional alleles of HDAC5.

2. The transgenic mouse of claim 1, further comprising a detectable marker gene under the control of a myocyte enhancer factor-2 (MEF2) regulated promoter.

3. The transgenic mouse of claim 2, wherein said MEF2 regulated promoter is a Nur77 gene (NGFI-B) promoter.

4. The transgenic mouse of claim 2, wherein said detectable marker gene is selected from the group consisting of β-galactosidase, luciferase and GFP.

5. The transgenic mouse of claim 1, wherein said transgenic mouse lacks both functional alleles of HDAC5.

* * * * *

```
                           SEQUENCE LISTING

<160> NUMBER OF SEQ ID NOS: 1

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
ggcctttcct tctcctctat aaataccagc tctggtattt ca                         42
```